US007211398B2

(12) United States Patent
Astle et al.

(10) Patent No.: US 7,211,398 B2
(45) Date of Patent: May 1, 2007

(54) HUMAN GENES AND GENE EXPRESSION PRODUCTS: II

(75) Inventors: Jon H. Astle, Taunton, MA (US); Christopher C. Burgess, Westwood, MA (US); Theodore J. Catino, Attleboro, MA (US); Poornima Dwivedi, Alamo, CA (US); Marcia E. Lewis, Cohasset, MA (US); Gary A. Molino, Norfolk, MA (US); Susan H. Myerow, Lexington, MA (US); Arunthathi Thiagalingam, Lexington, MA (US); Stephen Thibodeau, Rochester, MN (US); Lawrence J. Burgart, Rochester, MN (US); Lisa Allyn Boardman, Rochester, MN (US)

(73) Assignees: Bayer Corporation, Tarrytown, NY (US); Mayo Foundation for Medical Education and Research, Rochester, MN (US)

( * ) Notice: Subject to any disclaimer, the term of this patent is extended or adjusted under 35 U.S.C. 154(b) by 546 days.

(21) Appl. No.: 10/280,403

(22) Filed: Oct. 25, 2002

(65) Prior Publication Data

US 2003/0082620 A1 May 1, 2003

Related U.S. Application Data

(60) Division of application No. 09/907,479, filed on Jul. 17, 2001, which is a continuation-in-part of application No. 09/385,982, filed on Aug. 30, 1999, now Pat. No. 6,262,334, which is a continuation-in-part of application No. 09/328,111, filed on Jun. 8, 1999, now Pat. No. 6,262,333.

(60) Provisional application No. 60/117,393, filed on Jan. 27, 1999, provisional application No. 60/098,639, filed on Aug. 31, 1998.

(51) Int. Cl.
*G01N 33/53* (2006.01)

(52) U.S. Cl. ........................................ 435/7.1
(58) Field of Classification Search .................. None
See application file for complete search history.

(56) References Cited

U.S. PATENT DOCUMENTS

| 4,824,776 A | 4/1989 | Heller ........................... 435/6 |
| 5,648,478 A | 7/1997 | Henderson ................. 536/24.1 |
| 5,686,240 A | 11/1997 | Schuchman et al. ........... 435/6 |
| 5,916,751 A | 6/1999 | Tabibzadeh et al. ........... 435/6 |

FOREIGN PATENT DOCUMENTS

| EP | 0 284 362 A | 9/1988 |
| EP | 1 277 843 A2 | 1/2003 |
| WO | WO 95 11923 A | 5/1995 |
| WO | WO 00/58473 | 10/2000 |
| WO | WO 01/11047 A2 | 2/2001 |
| WO | WO 02/29086 A2 | 4/2002 |

OTHER PUBLICATIONS

Zhang et al, GenBank® Accession No. BG661044 (Apr. 26, 2001).*
XP002089887, Schweinfest, C.W., et al.; "Subtraction hybridization cDNA libraries from colon carcinoma and hepatic cancer", Gene Analysis Techniques, vol. 7, Jan. 1, 1990, pp. 64-70.
XP002104685, Vider, B., et al.: "Human colorectal carcinogenesis is associated with deregulation of homeobox gene expression", Biochemical and Biophysical Research Communications, vol. 232, No. 3, Mar. 1997, pp. 742-748.
XP002024627, Jau Min Wong, et al.; "Ubiquitin-Ribosomal protein S27A gene overexpresses in human colorectal carcinoma is an early growth response gene", Cancer Research, vol. 53, No. 8, Apr. 15, 1993, pp. 1916-1920.
XP002089891, Van Belzen, N., et al.; "A novel gene which is up-regulated during colon epithelial cell differentiation and down-regulated in colorectal neoplasms", Laboratory Investigation, vol. 77, No. 1, Jul. 1, 1997, pp. 85-92.
Abe, et al., LST-2, A Human Liver Specific Organic Anion Transporter, Determines Methotrexate Sensitivity in Gastrointestinal Cancers, *Gastroenterology*, 2001; 120: pp. 1689-1699.
Konig et al., Localization and Genomic Organization of a New Hepatocellular Organic Anion Transporting Polypeptide, *The Journal of Biological Chemistry*, 2000; vol. 275, No. 30, pp. 23161-23168.
European Search Report 02255032.1.
Huch, et al.; "Identification of Differentially Expressed Genes in Human Trophoblast Cells by Differential-display RT-PCR"; *Placenta*; (1998); 19: 557-567. Database EMBL XP002272544.
Zhang, et al.; "Cloning and Functional Analysis of CDNAs with Open Reading Frames for 300 Previously Undefined Genes Expressed in CD34+ Hematopoietic Stem/Progenitor Cells"; *Genome Research*; (2000); 10: 1546-1560. Database EMBL XP002272545.
Zhang, et al.; "Database EMBL" XP-002272807; (2001).
Lai, et al.; "Identification of Novel Human Genes Evolutionarily Conserved in Caenorhabditis elegans by Comparative Proteomics"; *Genomic Research*; (2000); 10: 703-713, Database EMBL XP002272543.
European Search Report dated Mar. 9, 2004, Appl. No. 02 25 5032.

* cited by examiner

*Primary Examiner*—James Martinell
(74) *Attorney, Agent, or Firm*—Edwards Angell Palmer & Dodge LLP

(57) ABSTRACT

This invention relates to novel human genes, to proteins expressed by the genes, and to variants of the proteins. The invention also relates to diagnostic assays and therapeutic agents related to the genes and proteins, including probes, antisense constructs, and antibodies. The subject nucleic acids have been found to be differentially regulated in tumor cells, particularly in colon cancer tissue.

3 Claims, 8 Drawing Sheets

Figure 1. SEQ ID NO: 1

```
   1 atcagcaaca attaaaatat tcacgtggta tctgtagttt aataatggac caacatcaac
  61 atttgaataa aacagcagag tcagcatctt cagagaaaaa gaaaacaaga cgctgcaatg
 121 gattcaagat gttcttggca gccctgtcat tcagctatat tgctaaagca ctaggtggaa
 181 tcattatgaa aatttccatc actcaaatag aaaggagatt tgacatatcc tcttctcttg
 241 ctggtttaat tgatggaagc tttgaaattg gaaatttgct tgtgattgta tttgtaagtt
 301 actttggatc taaactacac agaccgaagt taattggaat tggttgtctc cttatgggaa
 361 ctggaagtat tttgacatct ttaccacatt tcttcatggg atattatagg tattctaaag
 421 aaacccatat taatccatca gaaaattcaa catcaagttt atcaacctgt ttaattaatc
 481 aaaccttatc attcaatgga acatcacctg agatagtaga aaaagattgt gtaaaggaat
 541 ctgggtcaca catgtggatc tatgtcttca tggggaatat gcttcgtggc atagggggaa
 601 cccccatagt accattgggg atttcataca ttgatgattt tgcaaaagaa ggacattctt
 661 ccttgtattt aggtagtttg aatgcaatag gaatgattgg tccagtcatt ggctttgcac
 721 tgggatctct gtttgctaaa atgtacgtgg atattggata tgtagatctg agcactatca
 781 gaataactcc taaggactct cgttgggttg gagcttggtg gcttggtttc cttgtgtctg
 841 gactattttc cattatttct tccataccat ttttttttct gccgaaaaat ccaaataaac
 901 cacaaaaaga aagaaaaatt tcactatcat tgcatgtgct gaaaacaaat gatgatagaa
 961 atcaaacagc taatttgacc aaccaaggaa aaaatgttac caaaaatgtg actggtttt
1021 tccagtcttt gaaaagcatc cttaccaatc ccctgtatgt tatatttctg cttttgacat
1081 tgttacaagt aagcagcttt attggttctt ttacttacgt ctttaaatat atggagcaac
1141 agtacggtca gtctgcatct catgctaact ttttgttggg aatcataacc attcctacgg
1201 ttgcaactgg aatgttttta ggaggattta tcattaaaaa attcaaattg tctttagttg
1261 gaattgccaa attttcattt cttacttcga tgatatcctt cttgtttcaa cttctatatt
1321 tccctctaat ctgcgaaagc aaatcagttc ccggcctaac cttgacctat gatggaaata
1381 attcagtggc atctcatgta gatgtaccac tttcttattg caactcagag tgcaattgtg
1441 atgaaagtca gtgggaacca gtctgtggga caatggaat aacttacctg tcaccttgtc
1501 tagcaggatg caaatcctca agtggtatta aaaagcatac agtgttttat aactgtagtt
1561 gtgtggaagt aactggtctc cagaacagaa attactcagc acacttgggt gaatgcccaa
1621 gagataatac ttgtacaagg aaattttca tctatgttgc aattcaagtc ataaactctt
1681 tgttctctgc aacaggaggt accacattta tcttgttgac tgtgaagatt gttcaacctg
1741 aattgaaagc acttgcaatg ggtttccagt caatggttat aagaacacta ggaggaattc
1801 tagctccaat atattttggg gctctgattg ataaaacatg tatgaagtgg tccaccaaca
1861 gctgtggagc acaaggagct tgtaggatat ataattccgt atttttgga agggtctact
1921 tgggcttatc tatagcttta agattcccag cacttgtttt atatattgtt tcatttttg
1981 ctatgaagaa aaaatttcaa ggaaaagata ccaaggcatc ggacaatgaa agaaaagtaa
2041 tggatgaagc aaacttagaa ttcttaaata tggtgaaca ttttgtacct tctgctggaa
2101 cagatagtaa aacatgtaat ttggacatgc aagacaatgc tgctgccaac taacattgca
2161 ttgattcatt aagatgttat ttttgaggtg ttcctggtct ttcactgaca attccaacat
2221 tctttactta cagtggacca atggataagt ctatgcatct ataataaact ataaaaaatg
2281 ggagtaccca tggttaggat atagctatgc ctttatggtt aagattagaa tatatgatcc
2341 ataaaattta aagtgagagg catggttagt gtgtgataca ataaaaagta attgtttggt
2401 agttgtaact gctaataaaa ccagtgacta gaatataagg gaggtaaaaa ggacaagata
2461 gattaatagc ctaaataaag agaaagcct gatgccttta aaaaatgaaa cacttggat
2521 gtattactta ggccaaaatc tggcctggat ttatgctata atatatattt tcatgttaag
2581 ttgtatattt ttcagaaatt ataatatta ttaatttaaa attcgaaaaa aaaaaaaaaa
2641 aaaaaa
```

Figure 2. SEQ ID NO: 2

```
MDQHQHLNKTAESASSEKKKTRRCNGFKMFLAALSFSYIAKALG
GIIMKISITQIERRFDISSSLAGLIDGSFEIGNLLVIVFVSYFGSKLHRPKLIGIGCL
LMGTGSILTSLPHFFMGYYRYSKETHINPSENSTSSLSTCLINQTLSFNGTSPEIVEK
DCVKESGSHMWIYVFMGNMLRGIGETPIVPLGISYIDDFAKEGHSSLYLGSLNAIGMI
GPVIGFALGSLFAKMYVDIGYVDLSTIRITPKDSRWVGAWWLGFLVSGLFSIISSIPF
FFLPKNPNKPQKERKISLSLHVLKTNDDRNQTANLTNQGKNVTKNVTGFFQSLKSILT
NPLYVIFLLLTLLQVSSFIGSFTYVFKYMEQQYGQSASHANFLLGIITIPTVATGMFL
GGFIIKKFKLSLVGIAKFSFLTSMISFLFQLLYFPLICESKSVAGLTLTYDGNNSVAS
HVDVPLSYCNSECNCDESQWEPVCGNNGITYLSPCLAGCKSSSGIKKHTVFYNCSCVE
VTGLQNRNYSAHLGECPRDNTCTRKFFIYVAIQVINSLFSATGGTTFILLTVKIVQPE
LKALAMGFQSMVIRTLGGILAPIYFGALIDKTCMKWSTNSCGAQGACRIYNSVFFGRV
YLGLSIALRFPALVLYIVFIFAMKKKFQGKDTKASDNERKVMDEANLEFLNNGEHFVP
SAGTDSKTCNLDMQDNAAAN
```

Figure 3. SEQ ID NO: 3

```
   1 acaggaggag acagcctccc ggcccgggga ggacaagtcg ctgccacctt tggctgccga
  61 cgtgattccc tgggacggtc cgtttcctgc cgtcaactgc cggccgagtt gggtctccgt
 121 ggttcaggcc ggctccccct tcctggtctc ccttctcccg ctgggccggt ttatcgggag
 181 gagattgtct tccagggcta gcaattggac ttttgatgat gtttgaccca gcggcaggaa
 241 tagcaggcaa cgtgatttca aagctgggct cagctcatgt ttcttctctc gtgtaatcgc
 301 aaaacccatt ttggagcagg aattccaatc atgtctgtga tggtggtgag aaagaaggtg
 361 acacggaaat gggagaaact cccaggcagg aacacctttt gctgtgatgg ccgcgtcatg
 421 atggcccggc aaaagggcat tttctacctg acccttttcc tcatcctggg gacatgtaca
 481 ctcttcttcg cctttgagtg ccgctacctg gctgttcagc tgtctcctgc catccctgta
 541 tttgctgcca tgctcttcct tttctccatg gctacactgt tgaggaccag cttcagtgac
 601 cctggagtga ttcctcgggc gctaccagat gaagcagctt tcatagaaat ggagatagaa
 661 gctaccaatg gtgcggtgcc gggctaccag cgaccaccgc ctcgtatcaa gaatttccag
 721 ataaacaacc agattgtgaa actgaaatac tgttacacat gcaagatctt ccggcctccc
 781 cgggcctccc attgcagcat ctgtgacaac tgtgtggagc gcttcgacca tcactgcccc
 841 tgggtgggga attgtgttgg aaagaggaac taccgctact tctacctctt catcctttct
 901 ctctccctcc tcacaatcta tgtcttcgcc ttcaacatcg tctatgtggc cctcaaatct
 961 ttgaaaattg gcttcttgga gacattgaaa gaaactcctg gaactgttct agaagtcctc
1021 atttgcttct ttacactctg gtccgtcgtg ggactgactg gatttcatac tttcctcgtg
1081 gctctcaacc agacaaccaa tgaagacatc aaaggatcat ggacagggaa gaatcgcgtc
1141 cagaatccct acagccatgg caatattgtg aagaactgct gtgaagtgct gtgtggcccc
1201 ttgcccccca gtgtgctgga tcgaaggggt attttgccac tggaggaaag tggaagtcga
1261 cctcccagta ctcaagagac cagtagcagc ctcttgccac agagcccagc ccccacagaa
1321 cacctgaact caaatgagat gccggaggac agcagcactc ccgaagagat gccacctcca
1381 gagcccccag agccaccaca ggaggcagct gaagctgaga agtagcctat ctatggaaga
1441 gacttttgtt tgtgtttaat tagggctatg agagatttca ggtgagaagt taaacctgag
1501 acagagagca agtaagctgt ccctttaat tgttttcctt tggtctttag tcacccagtt
1561 gcacactggg cattttcttg gctggcaagc tttttttaaa atttgctgaa acttcaaggg
1621 cagtggccag gaaggatgtt cagttcacct ctggataaac tgggaaaaat ggggtctctt
1681 ggggccgggc actggttt
```

Figure 4. SEQ ID NO: 4

```
MFLLSCNRKTHFGAGIPIMSVMVVRKKVTRKWEKLPGRNTFCCD
GRVMMARQKGIFYLTLFLILGTCTLFFAFECRYLAVQLSPAIPVFAAMLFLFSMATLL
RTSFSDPGVIPRALPDEAAFIEMEIEATNGAVPGYQRPPPRIKNFQINNQIVKLKYCY
TCKIFRPPRASHCSICDNCVERFDHHCPWVGNCVGKRNYRYFYLFILSLSLLTIYVFA
FNIVYVALKSLKIGFLETLKETPGTVLEVLICFFTLWSVVGLTGFHTFLVALNQTTNE
DIKGSWTGKNRVQNPYSHGNIVKNCCEVLCGPLPPSVLDRRGILPLEESGSRPPSTQE
TSSSLLPQSPAPTEHLNSNEMPEDSSTPEEMPPPEPPEPPQEAAEAEK
```

Figure 5. SEQ ID NO: 5

```
   1 acaagatgga ggattcggcc tcggcctcgc tgtcttctgc agccgctact ggaacctcca
  61 cctcgactcc agcggccccg acagcacgga agcagctgga taaagaacag gttagaaagg
 121 cagtggacgc tctcttgacg cattgcaagt ccaggaaaaa caattatggg ttgcttttga
 181 atgagaatga aagtttattt ttaatggtgg tattatggaa aattccaagt aaagaactga
 241 gggtcagatt gaccttgcct catagtattc gatcagattc agaagatatc tgtttattta
 301 cgaaggatga acccaattca actcctgaaa agacagaaca gttttataga aagcttttaa
 361 acaagcatgg aattaaaacc gtttctcaga ttatctccct ccaaactcta agaaggaat
 421 ataaatccta tgaagccaag ctccgccttc tgagcagttt tgatttcttc cttactgatg
 481 ccagaattag gcggctctta ccctcactca ttgggagaca tttctatcaa agaaagaaag
 541 ttccagtatc tgtaaacctt ctgtccaaga atttatcaag agagatcaat gactgtatag
 601 gtggaacggt cttaaacatt tctaaaagtg gttcttgcag tgctatacgt attggtcacg
 661 ttggaatgca aattgagcac atcattgaaa acattgttgc tgtcaccaaa ggactttcag
 721 aaaaattgcc agagaagtgg gagagcgtga actcctgtt tgtgaaaact gagaaatcgg
 781 ctgcacttcc catcttttcc tcgtttgtca gcaattggga tgaagccacc aaaagatctt
 841 tgcttaataa gaagaaaaaa gaggcaagga gaaacgaag agaaagaaat tttgaaaaac
 901 aaaaggagag gaagaagaag aggcagcagg ctaggaagac tgcatcagtt cttagtaaag
 961 atgatgtggc acctgaaagt ggtgatacta cagtgaagaa acctgaatca aagaaggaac
1021 agaccccaga gcatgggaag aaaaaacgtg gcagaggaaa agcccaagtt aaagcaacaa
1081 atgaatccga agacgaaatc ccacagctgg taccaatagg aaagaagact ccagctaatg
1141 aaaaagtaga gattcaaaaa catgccacag gaaagaagtc tccagcaaag agtcctaatc
1201 ccagcacacc tcgtgggaag aaaagaaagg ctttgccagc atctgagacc ccaaaagctg
1261 cagagtctga gaccccaggg aaaagcccag agaagaagcc aaaaatcaaa gaagaggcag
1321 tgaaggaaaa aagtccttcg ctggggaaaa aagatgcgag acagactcca aaaagccag
1381 aggccaagtt tttcaccact cctagtaaat ctgtgagaaa agcttcccac accccaaaa
1441 aatggcccaa aaacccaaa taccccagtc gacctaaagt cagtgattca actggaagga
1501 aacctcaatg ctgcctccag agctttttgg aaatactcag atcctggccg cctttgtaac
1561 cttctctaaa cgtcaggcct ggacttaaaa gatttttaa aacctccata agtagtccag
1621 ggcggtggc tcacgcctgt aatcccagca ctttgggagg ccgaggcagg cggatcacaa
1681 ggtcaacgag atcgagacca tcctggccaa catggtgaaa ccctgtctgt accaaaaata
1741 caaaaattaa ttgggcatgg tggtggacac ctgtaatccc agctactagg gaggctgagg
1801 caggagaatt gcttgaacct ggggaggcgga ggttgcagtg agccactgca ctccagcctg
1861 atgacagagc aagactcagt caaaaataaa taaaaataat aaaacctc
```

Figure 6. SEQ ID NO: 6

MEDSASASLSSAAATGTSTSTPAAPTARKQLDKEQVRKAVDALL
THCKSRKNNYGLLLNENESLFLMVVLWKIPSKELRVRLTLPHSIRSDSEDICLFTKDE
PNSTPEKTEQFYRKLLNKHGIKTVSQIISLQTLKKEYKSYEAKLRLLSSFDFFLTDAR
IRRLLPSLIGRHFYQRKKVPVSVNLLSKNLSREINDCIGGTVLNISKSGSCSAIRIGH
VGMQIEHIIENIVAVTKGLSEKLPEKWESVKLLFVKTEKSAALPIFSSFVSNWDEATK
RSLLNKKKKEARRKRRERNFEKQKERKKKRQQARKTASVLSKDDVAPESGDTTVKKPE
SKKEQTPEHGKKKRGRGKAQVKATNESEDEIPQLVPIGKKTPANEKVEIQKHATGKKS
PAKSPNPSTPRGKKRKALPASETPKAAESETPGKSPEKKPKIKEEAVKEKSPSLGKKD
ARQTPKKPEAKFFTTPSKSVRKASHTPKKWPKKPKYPSRPKVSDSTGRKPQCCLQSFL
EILRSWPPL

Figure 7. SEQ ID NO: 7

```
  1 gccagccctc ggaaacgcga agtgagcggc ggggtcgact gacggtaacg gggcagagag
 61 gctgttcgca gagctgcgga agatgaatgc cagaggactt ggatctgagc taaaggacag
121 tattccagtt actgaacttt cagcaagtgg acctttgaa agtcatgatc ttcttcggaa
181 aggtttttct tgtgtgaaaa atgaactttt gcctagtcat ccccttgaat tatcagaaaa
241 aaatttccag ctcaaccaag ataaaatgaa ttttccaca ctgagaaaca ttcagggtct
301 atttgctccg ctaaaattac agatggaatt caaggcagtg cagcaggttc agcgtcttcc
361 atttctttca agctcaaatc tttcactgga tgttttgagg ggtaatgatg agactattgg
421 atttgaggat attcttaatg atccatcaca aagcgaagtc atgggagagc cacacttgat
481 ggtggaatat aaacttggtt tactgtaata gtgtgctgtt catggaaacc gagggctgca
541 tcttgtttat agtcatcttt gtactgtaat ttgatgtaca caacattaaa agtactgaca
601 cctgaaaaaa aaaaaaaaaa aaaaaaaaaa aaaa
```

Figure 8. SEQ ID NO: 8

MNARGLGSELKDSIPVTELSASGPFESHDLLRKGFSCVKNELLP
SHPLELSEKNFQLNQDKMNFSTLRNIQGLFAPLKLQMEFKAVQQVQRLPFLSSSNLSL
DVLRGNDETIGFEDILNDPSQSEVMGEPHLMVEYKLGLL

SEQUENCE LISTING

<160> NUMBER OF SEQ ID NOS: 8

<210> SEQ ID NO 1
<211> LENGTH: 2646
<212> TYPE: DNA
<213> ORGANISM: Homo sapiens

<400> SEQUENCE: 1

```
atcagcaaca attaaaatat tcacgtggta tctgtagttt aataatggac caacatcaac      60
atttgaataa aacagcagag tcagcatctt cagagaaaaa gaaaacaaga cgctgcaatg     120
gattcaagat gttcttggca gccctgtcat tcagctatat tgctaaagca ctaggtggaa     180
tcattatgaa aatttccatc actcaaatag aaaggagatt tgacatatcc tcttctcttg     240
ctggtttaat tgatggaagc tttgaaattg gaaatttgct tgtgattgta tttgtaagtt     300
actttggatc taaactacac agaccgaagt taattggaat tggttgtctc cttatgggaa     360
ctggaagtat tttgacatct ttaccacatt tcttcatggg atattatagg tattctaaag     420
aaacccatat taatccatca gaaaattcaa catcaagttt atcaacctgt ttaattaatc     480
aaaccttatc attcaatgga acatcacctg agatagtaga aaaagattgt gtaaaggaat     540
ctgggtcaca catgtggatc tatgtcttca tggggaatat gcttcgtggc ataggggaaa     600
cccccatagt accattgggg atttcataca ttgatgattt tgcaaaagaa ggacattctt     660
ccttgtattt aggtagtttg aatgcaatag gaatgattgg tccagtcatt ggctttgcac     720
tgggatctct gtttgctaaa atgtacgtgg atattggata tgtagatctg agcactatca     780
gaataactcc taaggactct cgttgggttg gagcttggtg gcttggtttc cttgtgtctg     840
gactattttc cattatttct tccataccat tttttttctt gccgaaaaat ccaaataaac     900
cacaaaaaga aagaaaaatt tcactatcat tgcatgtgct gaaaacaaat gatgatagaa     960
atcaaacagc taatttgacc aaccaaggaa aaaatgttac caaaaatgtg actggttttt    1020
tccagtcttt gaaaagcatc cttaccaatc ccctgtatgt tatatttctg cttttgacat    1080
tgttacaagt aagcagcttt attggttctt ttacttacgt ctttaaatat atggagcaac    1140
agtacggtca gtctgcatct catgctaact ttttgttggg aatcataacc attcctacgg    1200
ttgcaactgg aatgtttta ggaggattta tcattaaaaa attcaaattg tctttagttg    1260
```

-continued

```
gaattgccaa attttcattt cttacttcga tgatatcctt cttgtttcaa cttctatatt    1320
tccctctaat ctgcgaaagc aaatcagttg ccggcctaac cttgacctat gatggaaata    1380
attcagtggc atctcatgta gatgtaccac tttcttattg caactcagag tgcaattgtg    1440
atgaaagtca gtgggaacca gtctgtggga acaatggaat aacttacctg tcaccttgtc    1500
tagcaggatg caaatcctca agtggtatta aaaagcatac agtgttttat aactgtagtt    1560
gtgtggaagt aactggtctc cagaacagaa attactcagc acacttgggt gaatgcccaa    1620
gagataatac ttgtacaagg aaatttttca tctatgttgc aattcaagtc ataaactctt    1680
tgttctctgc aacaggaggt accacattta tcttgttgac tgtgaagatt gttcaacctg    1740
aattgaaagc acttgcaatg ggtttccagt caatggttat aagaacacta ggaggaattc    1800
tagctccaat atattttggg gctctgattg ataaaacatg tatgaagtgg tccaccaaca    1860
gctgtggagc acaaggagct tgtaggatat ataattccgt atttttttgga agggtctact    1920 tgggcttatc tatagcttta agattcccag cacttgtttt atatattgtt ttcattttttg    1980 ctatgaagaa aaaatttcaa ggaaaagata ccaaggcatc ggacaatgaa agaaaagtaa    2040
tggatgaagc aaacttagaa ttcttaaata atggtgaaca ttttgtacct tctgctggaa    2100
cagatagtaa aacatgtaat ttggacatgc aagacaatgc tgctgccaac taacattgca    2160
ttgattcatt aagatgttat ttttgaggtg ttcctggtct ttcactgaca attccaacat    2220
tctttactta cagtggacca atggataagt ctatgcatct ataataaact ataaaaaatg    2280
ggagtaccca tggttaggat atagctatgc ctttatggtt aagattagaa tatatgatcc    2340
ataaaattta aagtgagagg catggttagt gtgtgataca ataaaaagta attgtttggt    2400
agttgtaact gctaataaaa ccagtgacta gaatataagg gaggtaaaaa ggacaagata    2460
gattaatagc ctaaataaag agaaaagcct gatgccttta aaaaatgaaa cactttggat    2520
gtattactta ggccaaaatc tggcctggat ttatgctata atatatattt tcatgttaag    2580
ttgtatattt ttcagaaatt ataaatatta ttaatttaaa attcgaaaaa aaaaaaaaaa    2640
aaaaaa                                                              2646
```

<210> SEQ ID NO 2
<211> LENGTH: 702
<212> TYPE: PRT
<213> ORGANISM: Homo sapiens

<400> SEQUENCE: 2

```
Met Asp Gln His Gln His Leu Asn Lys Thr Ala Glu Ser Ala Ser Ser
1               5                   10                  15

Glu Lys Lys Lys Thr Arg Arg Cys Asn Gly Phe Lys Met Phe Leu Ala
            20                  25                  30

Ala Leu Ser Phe Ser Tyr Ile Ala Lys Ala Leu Gly Gly Ile Ile Met
        35                  40                  45

Lys Ile Ser Ile Thr Gln Ile Glu Arg Arg Phe Asp Ile Ser Ser Ser
    50                  55                  60

Leu Ala Gly Leu Ile Asp Gly Ser Phe Glu Ile Gly Asn Leu Leu Val
65                  70                  75                  80

Ile Val Phe Val Ser Tyr Phe Gly Ser Lys Leu His Arg Pro Lys Leu
                85                  90                  95

Ile Gly Ile Gly Cys Leu Leu Met Gly Thr Gly Ser Ile Leu Thr Ser
            100                 105                 110

Leu Pro His Phe Phe Met Gly Tyr Tyr Arg Tyr Ser Lys Glu Thr His
        115                 120                 125
```

```
Ile Asn Pro Ser Glu Asn Ser Thr Ser Ser Leu Ser Thr Cys Leu Ile
    130                 135                 140

Asn Gln Thr Leu Ser Phe Asn Gly Thr Ser Pro Glu Ile Val Glu Lys
145                 150                 155                 160

Asp Cys Val Lys Glu Ser Gly Ser His Met Trp Ile Tyr Val Phe Met
                165                 170                 175

Gly Asn Met Leu Arg Gly Ile Gly Glu Thr Pro Ile Val Pro Leu Gly
            180                 185                 190

Ile Ser Tyr Ile Asp Asp Phe Ala Lys Glu Gly His Ser Ser Leu Tyr
        195                 200                 205

Leu Gly Ser Leu Asn Ala Ile Gly Met Ile Gly Pro Val Ile Gly Phe
    210                 215                 220

Ala Leu Gly Ser Leu Phe Ala Lys Met Tyr Val Asp Ile Gly Tyr Val
225                 230                 235                 240

Asp Leu Ser Thr Ile Arg Ile Thr Pro Lys Asp Ser Arg Trp Val Gly
                245                 250                 255

Ala Trp Trp Leu Gly Phe Leu Val Ser Gly Leu Phe Ser Ile Ile Ser
            260                 265                 270

Ser Ile Pro Phe Phe Phe Leu Pro Lys Asn Pro Asn Lys Pro Gln Lys
        275                 280                 285

Glu Arg Lys Ile Ser Leu Ser Leu His Val Leu Lys Thr Asn Asp Asp
    290                 295                 300

Arg Asn Gln Thr Ala Asn Leu Thr Asn Gln Gly Lys Asn Val Thr Lys
305                 310                 315                 320

Asn Val Thr Gly Phe Phe Gln Ser Leu Lys Ser Ile Leu Thr Asn Pro
                325                 330                 335

Leu Tyr Val Ile Phe Leu Leu Leu Thr Leu Leu Gln Val Ser Ser Phe
            340                 345                 350

Ile Gly Ser Phe Thr Tyr Val Phe Lys Tyr Met Glu Gln Gln Tyr Gly
        355                 360                 365

Gln Ser Ala Ser His Ala Asn Phe Leu Leu Gly Ile Ile Thr Ile Pro
    370                 375                 380

Thr Val Ala Thr Gly Met Phe Leu Gly Gly Phe Ile Ile Lys Lys Phe
385                 390                 395                 400

Lys Leu Ser Leu Val Gly Ile Ala Lys Phe Ser Phe Leu Thr Ser Met
                405                 410                 415

Ile Ser Phe Leu Phe Gln Leu Leu Tyr Phe Pro Leu Ile Cys Glu Ser
            420                 425                 430

Lys Ser Val Ala Gly Leu Thr Leu Thr Tyr Asp Gly Asn Asn Ser Val
        435                 440                 445

Ala Ser His Val Asp Val Pro Leu Ser Tyr Cys Asn Ser Glu Cys Asn
    450                 455                 460

Cys Asp Glu Ser Gln Trp Glu Pro Val Cys Gly Asn Asn Gly Ile Thr
465                 470                 475                 480

Tyr Leu Ser Pro Cys Leu Ala Gly Cys Lys Ser Ser Gly Ile Lys
                485                 490                 495

Lys His Thr Val Phe Tyr Asn Cys Ser Cys Val Glu Val Thr Gly Leu
            500                 505                 510

Gln Asn Arg Asn Tyr Ser Ala His Leu Gly Glu Cys Pro Arg Asp Asn
        515                 520                 525

Thr Cys Thr Arg Lys Phe Phe Ile Tyr Val Ala Ile Gln Val Ile Asn
    530                 535                 540
```

-continued

```
Ser Leu Phe Ser Ala Thr Gly Gly Thr Thr Phe Ile Leu Leu Thr Val
545                 550                 555                 560

Lys Ile Val Gln Pro Glu Leu Lys Ala Leu Ala Met Gly Phe Gln Ser
                565                 570                 575

Met Val Ile Arg Thr Leu Gly Gly Ile Leu Ala Pro Ile Tyr Phe Gly
            580                 585                 590

Ala Leu Ile Asp Lys Thr Cys Met Lys Trp Ser Thr Asn Ser Cys Gly
        595                 600                 605

Ala Gln Gly Ala Cys Arg Ile Tyr Asn Ser Val Phe Phe Gly Arg Val
    610                 615                 620

Tyr Leu Gly Leu Ser Ile Ala Leu Arg Phe Pro Ala Leu Val Leu Tyr
625                 630                 635                 640

Ile Val Phe Ile Phe Ala Met Lys Lys Lys Phe Gln Gly Lys Asp Thr
                645                 650                 655

Lys Ala Ser Asp Asn Glu Arg Lys Val Met Asp Glu Ala Asn Leu Glu
                660                 665                 670

Phe Leu Asn Asn Gly Glu His Phe Val Pro Ser Ala Gly Thr Asp Ser
            675                 680                 685

Lys Thr Cys Asn Leu Asp Met Gln Asp Asn Ala Ala Ala Asn
        690                 695                 700

<210> SEQ ID NO 3
<211> LENGTH: 1698
<212> TYPE: DNA
<213> ORGANISM: Homo sapiens

<400> SEQUENCE: 3
acaggaggag acagcctccc ggcccgggga ggacaagtcg ctgccacctt tggctgccga      60
cgtgattccc tgggacggtc cgtttcctgc cgtcaactgc cggccgagtt gggtctccgt     120
ggttcaggcc ggctccccct tcctggtctc ccttctcccg ctgggccggt ttatcgggag     180
gagattgtct tccagggcta gcaattggac ttttgatgat gtttgaccca gcggcaggaa     240
tagcaggcaa cgtgatttca agctgggct cagctcatgt ttcttctctc gtgtaatcgc      300
aaaacccatt ttggagcagg aattccaatc atgtctgtga tggtggtgag aaagaaggtg     360
acacggaaat gggagaaact cccaggcagg aacacctttt gctgtgatgg ccgcgtcatg     420
atggcccggc aaaagggcat tttctacctg acccttttcc tcatcctggg acatgtaca     480
ctcttcttcg cctttgagtg ccgctacctg gctgttcagc tgtctcctgc catccctgta     540
tttgctgcca tgctcttcct tttctccatg gctacactgt tgaggaccag cttcagtgac     600
cctggagtga ttcctcgggc gctaccagat gaagcagctt catagaaat ggagatagaa      660
gctaccaatg gtgcggtgcc gggctaccag cgaccaccgc ctcgtatcaa gaatttccag     720
ataaacaacc agattgtgaa actgaaatac tgttacacat gcaagatctt ccggcctccc     780
cgggcctccc cattgcagcat ctgtgacaac tgtgtgagc gcttcgacca tcactgcccc     840
tgggtgggga attgtgttgg aaagaggaac taccgctact ctacctctt catcctttct     900
ctctcccctcc tcacaatcta tgtcttcgcc ttcaacatcg tctatgtggc cctcaaatct     960
ttgaaaattg gcttcttgga acattgaaa gaaactcctg aactgttct agaagtcctc     1020
atttgcttct ttacactctg gtccgtcgtg ggactgactg gatttcatac tttcctcgtg     1080
gctctcaacc agacaaccaa tgaagacatc aaaggatcat ggacagggaa gaatcgcgtc     1140
cagaatccct acagccatgg caatattgtg aagaactgct gtgaagtgct gtgtggcccc     1200
ttgcccccca gtgtgctgga tcgaaggggt attttgccac tggaggaaag tggaagtcga     1260
```

-continued

```
cctcccagta ctcaagagac cagtagcagc ctcttgccac agagcccagc ccccacagaa   1320
cacctgaact caaatgagat gccggaggac agcagcactc ccgaagagat gccacctcca   1380
gagcccccag agccaccaca ggaggcagct gaagctgaga gtagcctat ctatggaaga    1440 gacttttgtt tgtgtttaat tagggctatg agagatttca ggtgagaagt taaacctgag   1500
acagagagca agtaagctgt ccctttaat tgttttcct tggtctttag tcacccagtt     1560
gcacactggg cattttcttg ctggcaagc tttttaaaa atttgctgaa acttcaaggg     1620
cagtggccag gaaggatgtt cagttcacct ctggataaac tgggaaaaat ggggtctctt   1680
ggggccgggc actggttt                                                1698
```

<210> SEQ ID NO 4
<211> LENGTH: 382
<212> TYPE: PRT
<213> ORGANISM: Homo sapiens

<400> SEQUENCE: 4

```
Met Phe Leu Leu Ser Cys Asn Arg Lys Thr His Phe Gly Ala Gly Ile
1               5                   10                  15

Pro Ile Met Ser Val Met Val Arg Lys Lys Val Thr Arg Lys Trp
            20                  25                  30

Glu Lys Leu Pro Gly Arg Asn Thr Phe Cys Cys Asp Gly Arg Val Met
        35                  40                  45

Met Ala Arg Gln Lys Gly Ile Phe Tyr Leu Thr Leu Phe Leu Ile Leu
    50                  55                  60

Gly Thr Cys Thr Leu Phe Phe Ala Phe Glu Cys Arg Tyr Leu Ala Val
65                  70                  75                  80

Gln Leu Ser Pro Ala Ile Pro Val Phe Ala Ala Met Leu Phe Leu Phe
                85                  90                  95

Ser Met Ala Thr Leu Leu Arg Thr Ser Phe Ser Asp Pro Gly Val Ile
                100                 105                 110

Pro Arg Ala Leu Pro Asp Glu Ala Ala Phe Ile Glu Met Glu Ile Glu
            115                 120                 125

Ala Thr Asn Gly Ala Val Pro Gly Tyr Gln Arg Pro Pro Arg Ile
        130                 135                 140

Lys Asn Phe Gln Ile Asn Asn Gln Ile Val Lys Leu Lys Tyr Cys Tyr
145                 150                 155                 160

Thr Cys Lys Ile Phe Arg Pro Pro Arg Ala Ser His Cys Ser Ile Cys
                165                 170                 175

Asp Asn Cys Val Glu Arg Phe Asp His His Cys Pro Trp Val Gly Asn
                180                 185                 190

Cys Val Gly Lys Arg Asn Tyr Arg Tyr Phe Tyr Leu Phe Ile Leu Ser
            195                 200                 205

Leu Ser Leu Leu Thr Ile Tyr Val Phe Ala Phe Asn Ile Val Tyr Val
        210                 215                 220

Ala Leu Lys Ser Leu Lys Ile Gly Phe Leu Glu Thr Leu Lys Glu Thr
225                 230                 235                 240

Pro Gly Thr Val Leu Glu Val Leu Ile Cys Phe Phe Thr Leu Trp Ser
                245                 250                 255

Val Val Gly Leu Thr Gly Phe His Thr Phe Leu Val Ala Leu Asn Gln
                260                 265                 270

Thr Thr Asn Glu Asp Ile Lys Gly Ser Trp Thr Gly Lys Asn Arg Val
            275                 280                 285
```

```
Gln Asn Pro Tyr Ser His Gly Asn Ile Val Lys Asn Cys Cys Glu Val
    290                 295                 300

Leu Cys Gly Pro Leu Pro Pro Ser Val Leu Asp Arg Arg Gly Ile Leu
305                 310                 315                 320

Pro Leu Glu Glu Ser Gly Ser Arg Pro Pro Ser Thr Gln Glu Thr Ser
                325                 330                 335

Ser Ser Leu Leu Pro Gln Ser Pro Ala Pro Thr Glu His Leu Asn Ser
            340                 345                 350

Asn Glu Met Pro Glu Asp Ser Ser Thr Pro Glu Glu Met Pro Pro Pro
        355                 360                 365

Glu Pro Pro Glu Pro Pro Gln Glu Ala Ala Glu Ala Glu Lys
    370                 375                 380

<210> SEQ ID NO 5
<211> LENGTH: 1908
<212> TYPE: DNA
<213> ORGANISM: Homo sapiens

<400> SEQUENCE: 5
```

| | | | | | |
|---|---|---|---|---|---|
| acaagatgga | ggattcggcc | tcggcctcgc | tgtcttctgc | agccgctact | ggaacctcca | 60 |
| cctcgactcc | agcggccccg | acagcacgga | agcagctgga | taaagaacag | gttagaaagg | 120 |
| cagtggacgc | tctcttgacg | cattgcaagt | ccaggaaaaa | caattatggg | ttgcttttga | 180 |
| atgagaatga | aagtttattt | ttaatggtgg | tattatggaa | aattccaagt | aaagaactga | 240 |
| gggtcagatt | gaccttgcct | catagtattc | gatcagattc | agaagatatc | tgtttattta | 300 |
| cgaaggatga | acccaattca | actcctgaaa | agacagaaca | gttttataga | aagcttttaa | 360 |
| acaagcatgg | aattaaaacc | gtttctcaga | ttatctccct | ccaaactcta | agaaggaat | 420 |
| ataaatccta | tgaagccaag | ctccgccttc | tgagcagttt | tgatttcttc | cttactgatg | 480 |
| ccagaattag | gcggctctta | ccctcactca | ttgggagaca | tttctatcaa | agaaagaaag | 540 |
| ttccagtatc | tgtaaaccct | ctgtccaaga | atttatcaag | agagatcaat | gactgtatag | 600 |
| gtggaacggt | cttaaacatt | tctaaaagtg | gttcttgcag | tgctatacgt | attggtcacg | 660 |
| ttggaatgca | aattgagcac | atcattgaaa | acattgttgc | tgtcaccaaa | ggactttcag | 720 |
| aaaaattgcc | agagaagtgg | gagagcgtga | aactcctgtt | tgtgaaaact | gagaaatcgg | 780 |
| ctgcacttcc | catcttttcc | tcgtttgtca | gcaattggga | tgaagccacc | aaaagatctt | 840 |
| tgcttaataa | gaagaaaaaa | gaggcaagga | gaaacgaag | agaaagaaat | tttgaaaaac | 900 |
| aaaaggagag | gaagaagaag | aggcagcagg | ctaggaagac | tgcatcagtt | cttagtaaag | 960 |
| atgatgtggc | acctgaaagt | ggtgatacta | cagtgaagaa | acctgaatca | agaaggaac | 1020 |
| agaccccaga | gcatgggaag | aaaaaacgtg | gcagaggaaa | agcccaagtt | aaagcaacaa | 1080 |
| atgaatccga | agacgaaatc | ccacagctgg | taccaatagg | aaagaagact | ccagctaatg | 1140 |
| aaaaagtaga | gattcaaaaa | catgccacag | gaaagaagtc | tccagcaaag | agtcctaatc | 1200 |
| ccagcacacc | tcgtgggaag | aaaagaaagg | ctttgccagc | atctgagacc | caaaagctg | 1260 |
| cagagtctga | gaccccaggg | aaaagcccag | agaagaagcc | aaaaatcaaa | gaagaggcag | 1320 |
| tgaaggaaaa | aagtccttcg | ctggggaaaa | aagatgcgag | acagactcca | aaaaagccag | 1380 |
| aggccaagtt | tttcaccact | cctagtaat | ctgtgagaaa | agcttccac | accccaaa | 1440 |
| aatggcccaa | aaacccaaa | tacccagtc | gacctaagt | cagtgattca | actggaagga | 1500 |
| aacctcaatg | ctgcctccag | agcttttgg | aaatactcag | atcctggccg | cctttgtaac | 1560 |
| cttctctaaa | cgtcaggcct | ggacttaaaa | gatttttaa | aacctccata | agtagtccag | 1620 |

```
gggcggtggc tcacgcctgt aatcccagca ctttgggagg ccgaggcagg cggatcacaa    1680
ggtcaacgag atcgagacca tcctggccaa catggtgaaa ccctgtctgt accaaaaata    1740
caaaaattaa ttgggcatgg tggtggacac ctgtaatccc agctactagg gaggctgagg    1800
caggagaatt gcttgaacct gggaggcgga ggttgcagtg agccactgca ctccagcctg    1860
atgacagagc aagactcagt caaaaataaa taaaataat aaaacctc                  1908
```

<210> SEQ ID NO 6
<211> LENGTH: 517
<212> TYPE: PRT
<213> ORGANISM: Homo sapiens

<400> SEQUENCE: 6

```
Met Glu Asp Ser Ala Ser Ala Ser Leu Ser Ser Ala Ala Ala Thr Gly
1               5                   10                  15

Thr Ser Thr Ser Thr Pro Ala Ala Pro Thr Ala Arg Lys Gln Leu Asp
            20                  25                  30

Lys Glu Gln Val Arg Lys Ala Val Asp Ala Leu Leu Thr His Cys Lys
        35                  40                  45

Ser Arg Lys Asn Asn Tyr Gly Leu Leu Leu Asn Glu Asn Glu Ser Leu
    50                  55                  60

Phe Leu Met Val Val Leu Trp Lys Ile Pro Ser Lys Glu Leu Arg Val
65                  70                  75                  80

Arg Leu Thr Leu Pro His Ser Ile Arg Ser Asp Ser Glu Asp Ile Cys
                85                  90                  95

Leu Phe Thr Lys Asp Glu Pro Asn Ser Thr Pro Glu Lys Thr Glu Gln
            100                 105                 110

Phe Tyr Arg Lys Leu Leu Asn Lys His Gly Ile Lys Thr Val Ser Gln
        115                 120                 125

Ile Ile Ser Leu Gln Thr Leu Lys Lys Glu Tyr Lys Ser Tyr Glu Ala
    130                 135                 140

Lys Leu Arg Leu Leu Ser Ser Phe Asp Phe Phe Leu Thr Asp Ala Arg
145                 150                 155                 160

Ile Arg Arg Leu Leu Pro Ser Leu Ile Gly Arg His Phe Tyr Gln Arg
                165                 170                 175

Lys Lys Val Pro Val Ser Val Asn Leu Leu Ser Lys Asn Leu Ser Arg
            180                 185                 190

Glu Ile Asn Asp Cys Ile Gly Gly Thr Val Leu Asn Ile Ser Lys Ser
        195                 200                 205

Gly Ser Cys Ser Ala Ile Arg Ile Gly His Val Gly Met Gln Ile Glu
    210                 215                 220

His Ile Ile Glu Asn Ile Val Ala Val Thr Lys Gly Leu Ser Glu Lys
225                 230                 235                 240

Leu Pro Glu Lys Trp Glu Ser Val Lys Leu Leu Phe Val Lys Thr Glu
                245                 250                 255

Lys Ser Ala Ala Leu Pro Ile Phe Ser Ser Phe Val Ser Asn Trp Asp
            260                 265                 270

Glu Ala Thr Lys Arg Ser Leu Leu Asn Lys Lys Lys Glu Ala Arg
        275                 280                 285

Arg Lys Arg Arg Glu Arg Asn Phe Glu Lys Gln Lys Glu Arg Lys Lys
    290                 295                 300

Lys Arg Gln Gln Ala Arg Lys Thr Ala Ser Val Leu Ser Lys Asp Asp
305                 310                 315                 320
```

```
Val Ala Pro Glu Ser Gly Asp Thr Thr Val Lys Lys Pro Glu Ser Lys
            325                 330                 335

Lys Glu Gln Thr Pro Glu His Gly Lys Lys Arg Gly Arg Gly Lys
        340                 345                 350

Ala Gln Val Lys Ala Thr Asn Glu Ser Glu Asp Glu Ile Pro Gln Leu
        355                 360                 365

Val Pro Ile Gly Lys Lys Thr Pro Ala Asn Glu Lys Val Glu Ile Gln
    370                 375                 380

Lys His Ala Thr Gly Lys Lys Ser Pro Ala Lys Ser Pro Asn Pro Ser
385                 390                 395                 400

Thr Pro Arg Gly Lys Lys Arg Lys Ala Leu Pro Ala Ser Glu Thr Pro
                405                 410                 415

Lys Ala Ala Glu Ser Glu Thr Pro Gly Lys Ser Pro Glu Lys Lys Pro
                420                 425                 430

Lys Ile Lys Glu Glu Ala Val Lys Glu Lys Ser Pro Ser Leu Gly Lys
                435                 440                 445

Lys Asp Ala Arg Gln Thr Pro Lys Lys Pro Glu Ala Lys Phe Phe Thr
    450                 455                 460

Thr Pro Ser Lys Ser Val Arg Lys Ala Ser His Thr Pro Lys Lys Trp
465                 470                 475                 480

Pro Lys Lys Pro Lys Tyr Pro Ser Arg Pro Lys Val Ser Asp Ser Thr
                485                 490                 495

Gly Arg Lys Pro Gln Cys Cys Leu Gln Ser Phe Leu Glu Ile Leu Arg
                500                 505                 510

Ser Trp Pro Pro Leu
        515

<210> SEQ ID NO 7
<211> LENGTH: 634
<212> TYPE: DNA
<213> ORGANISM: Homo sapiens

<400> SEQUENCE: 7
gccagccctc ggaaacgcga agtgagcggc ggggtcgact gacggtaacg gggcagagag      60
gctgttcgca gagctgcgga agatgaatgc cagaggactt ggatctgagc taaaggacag     120
tattccagtt actgaacttt cagcaagtgg acctttgaa agtcatgatc ttcttcggaa      180 aggttttttct tgtgtgaaaa atgaactttt gcctagtcat ccccttgaat atcagaaaa     240 aaatttccag ctcaaccaag ataaaatgaa tttttccaca ctgagaaaca ttcagggtct     300
atttgctccg ctaaaattac agatggaatt caaggcagtg cagcaggttc agcgtcttcc     360
atttctttca agctcaaatc tttcactgga tgttttgagg ggtaatgatg agactattgg     420
atttgaggat attcttaatg atccatcaca aagcgaagtc atgggagagc cacacttgat     480
ggtggaatat aaacttggtt tactgtaata gtgtgctgtt catggaaacc gagggctgca     540
tcttgtttat agtcatcttt gtactgtaat ttgatgtaca caacattaaa agtactgaca     600
cctgaaaaaa aaaaaaaaaa aaaaaaaaaa aaaa                                 634

<210> SEQ ID NO 8
<211> LENGTH: 141
<212> TYPE: PRT
<213> ORGANISM: Homo sapiens

<400> SEQUENCE: 8

Met Asn Ala Arg Gly Leu Gly Ser Glu Leu Lys Asp Ser Ile Pro Val
1               5                   10                  15
```

```
Thr Glu Leu Ser Ala Ser Gly Pro Phe Glu Ser His Asp Leu Leu Arg
        20              25              30

Lys Gly Phe Ser Cys Val Lys Asn Glu Leu Leu Pro Ser His Pro Leu
        35              40              45

Glu Leu Ser Glu Lys Asn Phe Gln Leu Asn Gln Asp Lys Met Asn Phe
    50              55              60

Ser Thr Leu Arg Asn Ile Gln Gly Leu Phe Ala Pro Leu Lys Leu Gln
65              70              75              80

Met Glu Phe Lys Ala Val Gln Gln Val Gln Arg Leu Pro Phe Leu Ser
            85              90              95

Ser Ser Asn Leu Ser Leu Asp Val Leu Arg Gly Asn Asp Glu Thr Ile
            100             105             110

Gly Phe Glu Asp Ile Leu Asn Asp Pro Ser Gln Ser Glu Val Met Gly
        115             120             125

Glu Pro His Leu Met Val Glu Tyr Lys Leu Gly Leu Leu
130             135             140
```

HUMAN GENES AND GENE EXPRESSION PRODUCTS: II

RELATED APPLICATION INFORMATION

This application is a divisional of application Ser. No. 09/907,479, filed Jul. 17, 2001, which is a continuation-in-part of application Ser. No. 09/385,982, filed on Aug. 30, 1999, now U.S. Pat. No. 6,262,334 which is a continuation-in-part of application Ser. No. 09/328,111, filed Jun. 8, 1999, now U.S. Pat. No. 6,262,333 which is based on Provisional Application Nos. 60/117,393, filed Jan. 27, 1999 and 60/098,639, filed Aug. 31, 1998, all of which are incorporated by reference herein, in their entirety.

FIELD OF THE INVENTION

The present invention provides nucleic acid sequences and proteins encoded thereby, as well as probes derived from the nucleic acid sequences, antibodies directed to the encoded proteins, and diagnostic methods for detecting cancerous cells, especially colon cancer cells.

BACKGROUND OF THE INVENTION

Colorectal carcinoma is a malignant neoplastic disease. There is a high incidence of colorectal carcinoma in the Western world, particularly in the United States. Tumors of this type often metastasize through lymphatic and vascular channels. Many patients with colorectal carcinoma eventually die from this disease. In fact, it is estimated that 62,000 persons in the United States alone die of colorectal carcinoma annually.

However, if diagnosed early, colon cancer may be treated effectively by surgical removal of the cancerous tissue. Colorectal cancers originate in the colorectal epithelium and typically are not extensively vascularized (and therefore not invasive) during the early stages of development. Colorectal cancer is thought to result from the clonal expansion of a single mutant cell in the epithelial lining of the colon or rectum. The transition to a highly vascularized, invasive and ultimately metastatic cancer which spreads throughout the body commonly takes ten years or longer. If the cancer is detected prior to invasion, surgical removal of the cancerous tissue is an effective cure. However, colorectal cancer is often detected only upon manifestation of clinical symptoms, such as pain and black tarry stool. Generally, such symptoms are present only when the disease is well established, often after metastasis has occurred, and the prognosis for the patient is poor, even after surgical resection of the cancerous tissue. Early detection of colorectal cancer therefore is important in that detection may significantly reduce its morbidity.

Invasive diagnostic methods such as endoscopic examination allow for direct visual identification, removal, and biopsy of potentially cancerous growths such as polyps. Endoscopy is expensive, uncomfortable, inherently risky, and therefore not a practical tool for screening populations to identify those with colorectal cancer. Non-invasive analysis of stool samples for characteristics indicative of the presence of colorectal cancer or precancer is a preferred alternative for early diagnosis, but no known diagnostic method is available which reliably achieves this goal. A reliable, non-invasive, and accurate technique for diagnosing colon cancer at an early stage would help save many lives.

SUMMARY OF THE INVENTION

The present invention provides nucleic acid sequences and proteins encoded thereby, as well as probes derived from the nucleic acid sequences, antibodies directed to the encoded proteins, and diagnostic methods for detecting cancerous cells, especially colon cancer cells. The sequences disclosure herein have been found to be differentially expressed in samples obtained from colon cancer cell lines and/or colon cancer tissue.

In one embodiment, the invention provides a nucleic acid comprising a nucleotide sequence comprising the sequence of SEQ ID Nos. 1, 3, 5, or 7, or a sequence complementary thereto. The sequence further may comprise a transcriptional regulatory sequence operably linked to the nucleotide sequence to render the nucleotide sequence suitable for use as an expression vector. In another embodiment, the nucleic acid may be included in an expression vector capable of replicating in a prokaryotic or eukaryotic cell. In a related embodiment, the invention provides a host cell transfected with the expression vector.

In one embodiment, the invention provides a nucleic acid comprising a nucleotide sequence which hybridizes under stringent conditions to a sequence of SEQ ID Nos. 1, 3, 5, or 7, or a sequence complementary thereto. The sequence further may comprise a transcriptional regulatory sequence operably linked to the nucleotide sequence to render the nucleotide sequence suitable for use as an expression vector. In another embodiment, the nucleic acid may be included in an expression vector capable of replicating in a prokaryotic or eukaryotic cell. In a related embodiment, the invention provides a host cell transfected with the expression vector.

In another embodiment, the invention provides a transgenic animal having a transgene of a nucleic acid comprising a nucleotide sequence comprising the sequence of SEQ ID Nos. 1, 3, 5, or 7, or a sequence complementary thereto, incorporated in cells thereof. In another embodiment, the invention provides a transgenic animal having a transgene of a nucleic acid comprising a nucleic acid sequence which hybridizes under stringent conditions to a sequence comprising the sequence of SEQ ID Nos 1, 3, 5, or 7. The transgene modifies the level of expression of the nucleic acid, the stability of a mRNA transcript of the nucleic acid, or the activity of the encoded product of the nucleic acid.

In yet another embodiment, the invention provides an isolated substantially pure nucleic acid corresponding to at least about 8, at least about 12, at least about 15, at least about 25, or at least about 40 consecutive nucleotides up to the full length of one of SEQ ID Nos. 1, 3, 5, or 7, or a sequence complementary thereto or up to the full length of the gene of which said sequence is a fragment. In another aspect, the invention provides a substantially pure nucleic acid which hybridizes under stringent conditions to a nucleic acid probe corresponding to at least about 8, at least about 12, at least about 15, at least about 25, or at least about 40 consecutive nucleotides up to the full length of one of SEQ ID Nos. 1, 3, 5, or 7, or a sequence complementary thereto or up to the full length of the gene of which said sequence is a fragment. The invention also provides an antisense oligonucleotide analog which comprises at least about 8, at least about 12, at least about 25, or at least about 40 consecutive nucleotides of one of SEQ ID Nos. 1, 3, 5, or 7 or a sequence complementary thereto, and which is resistant to cleavage by a nuclease, preferably an endogenous endonuclease or exonuclease. In another aspect the invention also provides an antisense oligonucleotide analog which hybridizes under stringent conditions to at least about 8, at least about 12, at least about 25, or at least about 40 consecutive nucleotides of one of SEQ ID Nos. 1, 3, 5, or 7 or a sequence complementary thereto, and which is resistant to cleavage by a nuclease, preferably an endogenous endonuclease or exonuclease.

In another embodiment, the invention provides a probe/primer comprising a substantially purified oligonucleotide, said oligonucleotide comprising a region of a nucleic acid sequence of SEQ ID Nos. 1, 3, 5, or 7 sufficient to hybridize with a nuleic acid substantially complementary to the sequence of SEQ ID Nos. 1, 3, 5, or 7, and containing a region of nucleotide sequence which comprises at least about 8 at least about 12, at least about 15, at least about 25, or at least about 40 consecutive nucleotides of sense or antisense sequence selected from SEQ ID Nos. 1, 3, 5, or 7 up to the full length of one of SEQ ID Nos. 1, 3, 5, or 7 or a sequence complementary thereto. In a further embodiment, the invention provides a probe/primer comprising a substantially purified oligonucleotide, wherein the oligonucleotide comprises a region of nucleic acid sequence complementary to the sequence of SEQ ID Nos. 1, 3, 5, or 7 sufficient to hybridize with a sequence of SEQ ID Nos 1, 3, 5, or 7. In preferred embodiments, the probe selectively hybridizes with a target nucleic acid. In another embodiment, the probe may include a label group attached thereto and able to be detected. The label group may be selected from radioisotopes, fluorescent compounds, enzymes, and enzyme co-factors. The invention further provides arrays of at least about 10, at least about 25, at least about 50, or at least about 100 different probes as described above attached to a solid support.

As used herein, "sufficient to hybridize" refers to conditions, including the degree of complementarity between two nucleic acid sequences, which are sufficient to permit annealing of the two sequences under stringent hybridization conditions. Stringent hybridization conditions are well known to those of skill in the art and may be found in numerous scientific texts and laboratory manuals (see, for example, Maniatis et al., 1982 *Molecular Cloning: A Laboratory Manual*, Cold Spring Harbor Press, Inc.). Other conditions which may affect whether two sequences are sufficient to hybridize include G/C content, melting temperature and sequence length. Preferably, sequence which are "sufficient to hybridize" are at least 8 nucleotides in length, and have a G/C content no greater than about 50%.

In yet another embodiment, the invention pertains to a method of determining the phenotype of a cell, comprising detecting the differential expression, relative to a normal cell, of at least one nucleic acid comprising SEQ ID Nos. 1, 3, 5, or 7, wherein the nucleic acid is differentially expressed by at least about 0.5 fold, at least about 1 fold, at least about 2 fold, or at least up to about 50 fold. In a further aspect the invention pertains to a method of determining the phenotype of a cell, comprising detecting the differential expression, relative to a normal cell, of at least one nucleic acid which hybridizes under stringent conditions one of SEQ ID Nos. 1, 3, 5, or 7, wherein the nucleic acid is differentially expressed by at least at least about 0.5 fold, at least about 1 fold, at least about 2 fold, or at least up to about 50 fold.

In another aspect, the invention provides polypeptides encoded by the subject nucleic acids. In one embodiment, the polypeptides comprise the sequence of SEQ ID Nos. 2, 4, 6, or 8, or a fragment thereof. In another embodiment, the invention pertains to a polypeptide including an amino acid sequence encoded by a nucleic acid comprising a nucleotide sequence of SEQ ID Nos. 1, 3, 5, or 7 or a sequence complementary thereto, or a fragment-thereof. The fragments may comprise, for example, at least about 10, at least about 20, at least about 30, or at least about 40 amino acids of the present polypeptides.

Further provided are antibodies which specifically bind to a polypeptide comprising the sequence of SEQ ID Nos. 2, 4, 6, or 8, or a fragment thereof. In another embodiment, the invention pertains to antibodies which bind to a polypeptide comprising an amino acid sequence encoded by a nucleic acid comprising a nucleotide sequence of SEQ ID Nos. 1, 3, 5, or 7 or a sequence complementary thereto, or a fragment thereof. The fragments bound by the antibodies of the invention may comprise, for example, at least about 10, at least about 20, at least about 30, or at least about 40 amino acids of the present polypeptides.

In still another aspect, the invention provides diagnostic methods. In one embodiment, the invention pertains to a method for determining the phenotype of cells from a patient by providing a nucleic acid probe comprising a nucleotide sequence having at least about 8, at least about 12, at least about 15, at least about 25, or at least about 40 consecutive nucleotides represented in a sequence of SEQ ID Nos. 1, 3, 5, or 7 or a sequence complementary thereto or up to the full length of the gene of which said sequence is a fragment, obtaining a sample of cells from a patient, providing a second sample of cells substantially all of which are non-cancerous, contacting the nucleic acid probe under stringent conditions with mRNA of each of said first and second cell samples, and comparing (a) the amount of hybridization of the probe with mRNA of the first cell sample, with (b) the amount of hybridization of the probe with mRNA of the second cell sample, wherein a difference of at least about 0.5 fold, at least about 1 fold, at least about 2 fold, or at least up to about 50 fold in the amount of hybridization with the mRNA of the first cell sample as compared to the amount of hybridization with the mRNA of the second cell sample is indicative of the phenotype of cells in the first cell sample. Determining the phenotype includes determining the genotype, as the term is used herein.

In another embodiment, the invention provides a test kit for identifying transformed (i.e., malignant) cells, comprising a probe/primer as described above, for measuring a level of a nucleic acid comprising a nucleic acid of SEQ ID Nos. 1, 3, 5, or 7, or a sequence complementary thereto in a sample of cells isolated from a patient. In certain embodiments, the kit may further include instructions for using the kit, compositions for suspending or fixing the cells, detectable tags or labels, compositions for rendering a nucleic acid susceptible to hybridization, compositions for lysing cells, or compositions for the purification of nucleic acids.

In another embodiment, the invention provides a method of determining the phenotype of a cell, comprising detecting the differential expression, relative to a normal cell, of at least one protein of SEQ ID Nos. 2, 4, 6, or 8, wherein the protein is differentially expressed by at least about 0.5 fold, at least about 2 fold, at least about 5 fold, at least about 20 fold, or at least about 50 fold. In another embodiment, the invention provides a method of determining the phenotype of a cell, comprising detecting the differential expression, relative to a normal cell, of at least one protein of SEQ ID Nos. 2, 4, 6, or 8, wherein the protein is differentially expressed by at least about 0.5 fold, at least about 2 fold, at least about 5 fold, at least about 20 fold, or at least about 50 fold. In one embodiment, the level of the protein is detected in an immunoassay.

The invention further pertains to a method for determining the presence or absence of a nucleic acid comprising one of SEQ ID Nos. 1, 3, 5, or 7, or a sequence complementary thereto in a cell, comprising contacting the cell with a probe as described above. The invention further provides a method for determining the presence or absence of a subject polypeptide of SEQ ID Nos. 2, 4, 6, or 8 in a cell, comprising contacting the cell with an antibody as described above. In yet another embodiment, the invention provides a method for determining the presence of an aberrant mutation (e.g., deletion, insertion, or substitution of nucleic acids) or aberrant methylation in a gene comprising a sequence of SEQ ID Nos. 1, 3, 5, or 7 or a sequence complementary thereto, comprising collecting a sample of cells from a patient, isolating nucleic acid from the cells of the sample, contacting the nucleic acid sample with one or more primers which specifically hybridize to a nucleic acid sequence of SEQ ID Nos. 1, 3, 5, or 7 under conditions such that hybridization and amplification of the nucleic acid occurs, and comparing the presence, absence, or size of an amplification product to the amplification product of a normal cell.

In one embodiment, the invention provides a test kit for identifying transformed (i.e., malignant) cells, comprising an antibody specific for a protein encoded by a nucleic acid comprising any one of SEQ Nos. 1, 3, 5, or 7, or a sequence complementary thereto. In certain embodiments, the kit may further include instructions for using the kit, compositions for suspending or fixing the cells, detectable tags or labels, compositions for rendering a polypeptide susceptible to the binding of an antibody, compositions for lysing cells, or compositions for the purification of polypeptides.

In yet another aspect, the invention provides pharmaceutical compositions including the subject nucleic acids. In one embodiment, an agent which alters the level of expression in a cell of a nucleic acid comprising one of SEQ ID Nos. 1, 3, 5, or 7, or a sequence complementary thereto, is identified by providing a cell, treating the cell with a test agent, determining the level of expression in the cell of a nucleic acid of SEQ ID Nos. 1, 3, 5, or 7, or a sequence complementary thereto, and comparing the level of expression of the nucleic acid in the treated cell with the level of expression of the nucleic acid in an untreated cell, wherein a change in the level of expression of the nucleic acid in the treated cell relative to the level of expression of the nucleic acid in the untreated cell is indicative of an agent which alters the level of expression of the nucleic acid in a cell. The invention further provides a pharmaceutical composition comprising an agent identified by this method.

In another embodiment, the invention provides a pharmaceutical composition which includes a polypeptide either encoded by a nucleic acid having a nucleotide sequence comprising one of SEQ ID Nos. 1, 3, 5, or 7, or a sequence complementary thereto, or having the sequence of SEQ ID Nos. 2, 4, 6, or 8. In one embodiment, the invention pertains to a pharmaceutical composition comprising a nucleic acid including a sequence which hybridizes under stringent conditions to one of SEQ ID Nos. 1, 3, 5, or 7 or a sequence complementary thereto. Pharmaceutical compositions, useful in the present invention may further include fusion proteins comprising the amino acid sequence of SEQ ID Nos 2, 4, 6, or 8, or a fragment thereof, antibodies, or antibody fragments.

BRIEF DESCRIPTION OF THE FIGURE

FIG. 1 shows the nucleic acid sequence of SEQ ID NO: 1.
FIG. 2 shows the amino acid sequence of SEQ ID NO: 2.
FIG. 3 shows the nucleic acid sequence of SEQ ID NO: 3.
FIG. 4 shows the amino acid sequence of SEQ ID NO: 4.
FIG. 5 shows the nucleic acid sequence of SEQ ID NO: 5.
FIG. 6 shows the amino acid sequence of SEQ ID NO: 6.
FIG. 7 shows the nucleic acid sequence of SEQ ID NO: 7.
FIG. 8 shows the amino acid sequence of SEQ ID NO: 8.

DETAILED DESCRIPTION OF THE INVENTION

The invention relates to nucleic acids having the full length cDNA sequence of SEQ ID Nos. 1, 3, 5, or 7, or a sequence complementary thereto, and genes corresponding to these sequences, and to polypeptides and proteins encoded by these nucleic acids and genes, and portions thereof.

The invention further relates to the polypeptide sequences encoded by the mRNA sequence complementary to the cDNA sequence of SEQ ID Nos. 1, 3, 5, or 7, respectively including, but not limited to polypeptides having the amino acid sequence of SEQ ID Nos. 2, 4, 6, or 8.

Polypeptides and proteins that are variants of the polypeptides and proteins of SEQ ID Nos. 2, 4, 6, or 8 also are within the scope of the invention. The variants may differ from the wild-type protein in having one or more amino acid substitutions that enhance, add, or diminish a biological activity of the wild-type protein. Once the amino acid change is selected, a nucleic acid encoding that variant is constructed according to the invention. Such nucleic acids, which are variants of SEQ ID Nos 1, 3, 5, and 7, are encompassed by the invention.

The following detailed description discloses how to obtain or make cDNA and human genes corresponding to the present nucleic acids, how to express the nucleic acids and related genes, how to identify structural motifs of the genes, how to identify the function of a protein encoded by a gene corresponding to an nucleic acid, how to use nucleic acids as probes in mapping and in tissue profiling, how to use the corresponding polypeptides and proteins to raise antibodies, and how to use the nucleic acids, polypeptides, and proteins for therapeutic and diagnostic purposes.

Accordingly, certain aspects of the present invention relate to nucleic acids differentially expressed in tumor tissue, especially colon cancer cell lines, polypeptides encoded by such nucleic acids, antibodies immunoreactive with these polypeptides, and preparations of such compositions. Moreover, the present invention provides diagnostic and therapeutic assays, reagents, and compositions for detecting and treating disorders involving, for example, aberrant expression of the subject nucleic acids.

I. General

This invention relates in part to novel methods for identifying and/or classifying cancerous cells present in a human tumors, particularly in solid tumors, e.g., carcinomas and sarcomas, such as, for example, breast or colon cancers. The method uses genes that are differentially expressed in cancer cell lines and/or cancer tissue compared with related normal cells, such as normal colon cells, and thereby identifies or classifies tumor cells by the upregulation and/or downregulation of expression of particular genes, an event which is implicated in tumorigenesis.

Upregulation or increased expression of certain genes such as oncogenes, act to promote malignant growth. Downregulation or decreased expression of genes such as tumor suppressor genes also promotes malignant growth. Thus, alteration in the expression of either type of gene is a potential diagnostic indicator for determining whether a subject is at risk of developing or has cancer, e.g., colon cancer.

Accordingly, in one aspect, the invention also provides biomarkers, such as nucleic acid markers, for human tumor cells, e.g., for colon cancer cells. The invention also provides proteins encoded by these nucleic acid markers. The invention also features methods for identifying drugs useful for treatment of such cancer cells, and for treatment of a cancerous condition, such as colon cancer. Unlike prior methods, the invention provides a means for identifying cancer cells at an early stage of development, so that premalignant cells can be identified prior to their spreading throughout the human body. This allows early detection of potentially cancerous conditions, and treatment of those cancerous conditions prior to spread of the cancerous cells throughout the body, or prior to development of an irreversible cancerous condition.

II. Definitions

For convenience, the meaning of certain terms and phrases used in the specification, examples, and appended claims, are provided below.

The term "an aberrant expression", as applied to a nucleic acid of the present invention, refers to level of expression of that nucleic acid which differs from the level of expression of that nucleic acid in healthy tissue, or which differs from the activity of the polypeptide present in a healthy subject. An activity of a polypeptide can be aberrant because it is stronger than the activity of its native counterpart. Alternatively, an activity can be aberrant because it is weaker or absent relative to the activity of its native counterpart. An aberrant activity can also be a change in the activity; for example, an aberrant polypeptide can interact with a different target peptide. A cell can have an aberrant expression level of a gene due to overexpression or underexpression of that gene.

The term "agonist", as used herein, is meant to refer to an agent that mimics or upregulates (e.g., potentiates or supplements) the bioactivity of a protein. An agonist can be a wild-type protein or derivative thereof having at least one bioactivity of the wild-type protein. An agonist can also be a compound that upregulates expression of a gene or which increases at least one bioactivity of a protein. An agonist can also be a compound which increases the interaction of a polypeptide with another molecule, e.g., a target peptide or nucleic acid.

The term "allele", which is used interchangeably herein with "allelic variant", refers to alternative forms of a gene or portions thereof. Alleles occupy the same locus or position on homologous chromosomes. When a subject has two identical alleles of a gene, the subject is said to be homozygous for that gene or allele. When a subject has two different alleles of a gene, the subject is said to be heterozygous for the gene. Alleles of a specific gene can differ from each other in a single nucleotide, or several nucleotides, and can include substitutions, deletions, and/or insertions of nucleotides. An allele of a gene can also be a form of a gene containing mutations.

The term "allelic variant of a polymorphic region of a gene" refers to a region of a gene having one of several nucleotide sequences found in that region of the gene in other individuals.

"Antagonist" as used herein is meant to refer to an agent that downregulates (e.g., suppresses or inhibits) at least one bioactivity of a protein. An antagonist can be a compound which inhibits or decreases the interaction between a protein and another molecule, e.g., a target peptide or enzyme substrate. An antagonist can also be a compound that downregulates expression of a gene or which reduces the amount of expressed protein present.

The term "antibody" as used herein is intended to include whole antibodies, e.g., of any isotype (IgG, IgA, IgM, IgE, etc), and includes fragments thereof, and single-chain antibodies, which also are specifically reactive with a vertebrate, e.g., mammalian, protein. Antibodies can be fragmented using conventional techniques and the fragments screened for utility in the same manner as described above for whole antibodies. Thus, the term includes segments of proteolytically-cleaved or recombinantly-prepared portions of an antibody molecule that are capable of selectively reacting with a certain protein. Nonlimiting examples of such proteolytic and/or recombinant fragments include Fab, F(ab')2, Fab', Fv, and single chain antibodies (scFv) containing a V[L] and/or V[H] domain joined by a peptide linker. The scFv's may be covalently or non-covalently linked to form antibodies having two or more binding sites. The subject invention includes polyclonal, monoclonal, or other purified preparations of antibodies and recombinant antibodies.

The phenomenon of "apoptosis" is well known, and can be described as a programmed death of cells. As is known, apoptosis is contrasted with "necrosis", a phenomenon when cells die as a result of being killed by a toxic material, or other external effect. Apoptosis involves chromatic condensation, membrane blebbing, and fragmentation of DNA, all of which are generally visible upon microscopic examination.

A disease, disorder, or condition "associated with" or "characterized by" an aberrant expression of a nucleic acid refers to a disease, disorder, or condition in a subject which is caused by, contributed to by, or causative of an aberrant level of expression of a nucleic acid.

As used herein the term "bioactive fragment of a polypeptide" refers to a fragment of a full-length polypeptide, wherein the fragment specifically agonizes (mimics) or antagonizes (inhibits) the activity of a wild-type polypeptide. The bioactive fragment preferably is a fragment capable of interacting with at least one other molecule, e.g., protein, small molecule, or DNA, which a full length protein can bind.

"Biological activity" or "bioactivity" or "activity" or "biological function", which are used interchangeably, herein mean an effector or antigenic function that is directly or indirectly performed by a polypeptide (whether in its native or denatured conformation), or by any subsequence thereof. Biological activities include binding to polypeptides, binding to other proteins or molecules, activity as a DNA binding protein, as a transcription regulator, ability to bind damaged DNA, etc. A bioactivity can be modulated by directly affecting the subject polypeptide. Alternatively, a bioactivity can be altered by modulating the level of the polypeptide, such as by modulating expression of the corresponding gene.

The term "biomarker" refers a biological molecule, e.g., a nucleic acid, peptide, hormone, etc., whose presence or concentration can be detected and correlated with a known condition, such as a disease state.

"Cells," "host cells", or "recombinant host cells" are terms used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A "chimeric polypeptide" or "fusion polypeptide" is a fusion of a first amino acid sequence encoding one of the subject polypeptides with a second amino acid sequence defining a domain (e.g., polypeptide portion) foreign to and not substantially homologous with any domain of the subject polypeptide. A chimeric polypeptide may present a foreign domain which is found (albeit in a different polypeptide) in an organism which also expresses the first polypeptide, or it may be an "interspecies," "intergenic," etc., fusion of polypeptide structures expressed by different kinds of organisms. In general, a fusion polypeptide can be represented by the general formula $(X)_n-(Y)_m-(Z)_n$, wherein Y represents a portion of the subject polypeptide, and X and Z are each independently absent or represent amino acid sequences which are not related to the native sequence found in an organism, or which are not found as a polypeptide chain contiguous with the subject sequence, where m is an integer greater than or equal to one, and each occurrence of n is, independently, 0 or an integer greater than or equal to 1 (n and m are preferably no greater than 5 or 10).

A "delivery complex" shall mean a targeting means (e.g., a molecule that results in higher affinity binding of a nucleic acid, protein, polypeptide or peptide to a target cell surface and/or increased cellular or nuclear uptake by a target cell). Examples of targeting means include: sterols (e.g., cholesterol), lipids (e.g., a cationic lipid, virosome or liposome), viruses (e.g., adenovirus, adeno-associated virus, and retrovirus), or target cell-specific binding agents (e.g., ligands recognized by target cell specific receptors). Preferred complexes are sufficiently stable in vivo to prevent significant uncoupling prior to internalization by the target cell. However, the complex is cleavable under appropriate conditions within the cell so that the nucleic acid, protein, polypeptide or peptide is released in a functional form.

As is well known, genes or a particular polypeptide may exist in single or multiple copies within the genome of an individual. Such duplicate genes may be identical or may have certain modifications, including nucleotide substitutions, additions or deletions, which all still code for polypeptides having substantially the same activity. The term "DNA sequence encoding a polypeptide" may thus refer to one or more genes within a particular individual. Moreover, certain differences in nucleotide sequences may exist between individual organisms, which are called alleles. Such allelic differences may or may not result in differences in amino acid sequence of the encoded polypeptide yet still encode a polypeptide with the same biological activity.

The term "equivalent" is understood to include nucleotide sequences encoding functionally equivalent polypeptides. Equivalent nucleotide sequences will include sequences that differ by one or more nucleotide substitutions, additions or deletions, such as allelic variants; and will, therefore, include sequences that differ from the nucleotide sequence of the nucleic acids shown in SEQ ID NOs: 1, 3, 5, or 7 due to the degeneracy of the genetic code.

As used herein, the terms "gene", "recombinant gene", and "gene construct" refer to a nucleic acid of the present invention associated with an open reading frame, including both exon and (optionally) intron sequences.

A "recombinant gene" refers to nucleic acid encoding a polypeptide and comprising exon sequences, though it may optionally include intron sequences which are derived from, for example, a related or unrelated chromosomal gene. The term "intron" refers to a DNA sequence present in a given gene which is not translated into protein and is generally found between exons.

The term "growth" or "growth state" of a cell refers to the proliferative state of a cell as well as to its differentiative state. Accordingly, the term refers to the phase of the cell cycle in which the cell is, e.g., G0, G1, G2, prophase, metaphase, or telophase, as well as to its state of differentiation, e.g., undifferentiated, partially differentiated, or fully differentiated. Without wanting to be limited, differentiation of a cell is usually accompanied by a decrease in the proliferative rate of a cell.

"Homology" or "identity" or "similarity" refers to sequence similarity between two peptides or between two nucleic acid molecules, with identity being a more strict comparison. Homology and identity can each be determined by comparing a position in each sequence which may be aligned for purposes of comparison. When a position in the compared sequence is occupied by the same base or amino acid, then the molecules are identical at that position. A degree of homology or similarity or identity between nucleic acid sequences is a function of the number of identical or matching nucleotides at positions shared by the nucleic acid sequences. A degree of identity of amino acid sequences is a function of the number of identical amino acids at positions shared by the amino acid sequences. A degree of homology or similarity of amino acid sequences is a function of the number of amino acids, i.e., structurally related, at positions shared by the amino acid sequences. An "unrelated" or "non-homologous" sequence shares less than 40% identity, though preferably less than 25% identity, with one of the sequences of the present invention.

The term "percent identical" refers to sequence identity between two amino acid sequences or between two nucleotide sequences. Identity can each be determined by comparing a position in each sequence which may be aligned for purposes of comparison. When an equivalent position in the compared sequences is occupied by the same base or amino acid, then the molecules are identical at that position; when the equivalent site occupied by the same or a similar amino acid residue (e.g., similar in steric and/or electronic nature), then the molecules can be referred to as homologous (similar) at that position. Expression as a percentage of homology, similarity, or identity refers to a function of the number of identical or similar amino acids at positions shared by the compared sequences. Various alignment algorithms and/or programs may be used, including FASTA, BLAST, or ENTREZ. FASTA and BLAST are available as a part of the GCG sequence analysis package (University of Wisconsin, Madison, Wis.), and can be used with, e.g., default settings. ENTREZ is available through the National Center for Biotechnology Information, National Library of Medicine, National Institutes of Health, Bethesda, Md. In one embodiment, the percent identity of two sequences can be determined by the GCG program with a gap weight of 1, e.g., each amino acid gap is weighted as if it were a single amino acid or nucleotide mismatch between the two sequences.

Other techniques for alignment are described in *Methods in Enzymology*, vol. 266: Computer Methods for Macromolecular Sequence Analysis (1996), ed. Doolittle, Academic Press, Inc., a division of Harcourt Brace & Co., San Diego, Calif., USA. Preferably, an alignment program that permits gaps in the sequence is utilized to align the sequences. The Smith-Waterman is one type of algorithm that permits gaps in sequence alignments. See *Meth. Mol.* 70–187 (1997). Also, the GAP program using the Needleman and Wunsch alignment method can be utilized to align sequences. An alternative search strategy uses MPSRCH software, which runs on a MASPAR computer. MPSRCH uses a Smith-Waterman algorithm to score sequences on a massively parallel computer. This approach improves ability to pick up distantly related matches, and is especially tolerant of small gaps and nucleotide sequence errors. Nucleic acid-encoded amino acid sequences can be used to search both protein and DNA databases.

Databases with individual sequences are described in *Methods in Enzymology.* ed. Doolittle, supra. Databases include Genbank, EMBL, and DNA Database of Japan (DDBJ).

Preferred nucleic acids have a sequence at least about 70%, and more preferably at least about 80% identical and more preferably at least about 90% and even more preferably at least about 95% identical to an nucleic acid sequence of a sequence shown in one of SEQ ID NOS: 1, 3, 5, or 7. Nucleic acids at least about 90%, more preferably about 95%, and most preferably at least about 98–99% identical with a nucleic sequence represented in one of SEQ ID NOS: 1, 3, 5, or 7 are of course also within the scope of the invention. In preferred embodiments, the nucleic acid is of mammalian origin.

The term "interact" as used herein is meant to include detectable interactions (e.g., biochemical interactions) between molecules, such as interaction between protein-protein, protein-nucleic acid, nucleic acid-nucleic acid, and protein-small molecule or nucleic acid-small molecule in nature.

The term "isolated" as used herein with respect to nucleic acids, such as DNA or RNA, refers to molecules separated from other DNAS, or RNAs, respectively, that are present in the natural source of the macromolecule. The term isolated as used herein also refers to a nucleic acid or peptide that is substantially pure, i.e., free of cellular material, viral material, or culture medium when produced by recombinant DNA techniques, or chemical precursors or other chemicals when chemically synthesized. Moreover, an "isolated nucleic acid" is meant to include substantially pure and/or purified nucleic acid fragments which are not naturally occurring as fragments and would not be found in the natural state. The term "isolated" is also used herein to refer to polypeptides which are isolated from other cellular proteins and is meant to encompass both substantially purified and recombinant polypeptides.

The terms "modulated" and "differentially regulated" as used herein refer to both upregulation (i.e., activation or stimulation (e.g., by agonizing or potentiating) and down-regulation (i.e., inhibition or suppression (e.g., by antagonizing, decreasing or inhibiting)).

The term "mutated gene" refers to an allelic form of a gene, which is capable of altering the phenotype of a subject having the mutated gene relative to a subject which does not have the mutated gene. If a subject must be homozygous for this mutation to have an altered phenotype, the mutation is said to be recessive. If one copy of the mutated gene is sufficient to alter the genotype of the subject, the mutation is said to be dominant. If a subject has one copy of the mutated gene and has a phenotype that is intermediate between that of a homozygous and that of a heterozygous subject (for that gene), the mutation is said to be co-dominant.

The designation "N", where it appears in the accompanying Sequence Listing, indicates that the identity of the corresponding nucleotide is unknown. "N" should therefore not necessarily be interpreted as permitting substitution with any nucleotide, e.g., A, T, C, or G, but rather as holding the place of a nucleotide whose identity has not been conclusively determined.

The "non-human animals" of the invention include mammalians such as rodents, non-human primates, sheep, dog, cow, chickens, amphibians, reptiles, etc. Preferred non-human animals are selected from the rodent family including rat and mouse, most preferably mouse, though transgenic amphibians, such as members of the Xenopus genus, and transgenic chickens can also provide important tools for understanding and identifying agents which can affect, for example, embryogenesis and tissue formation. The term "chimeric animal" is used herein to refer to animals in which the recombinant gene is found, or in which the recombinant gene is expressed in some but not all cells of the animal. The term "tissue-specific chimeric animal" indicates that one of the recombinant genes is present and/or expressed or disrupted in some tissues but not others.

As used herein, the term "nucleic acid" refers to polynucleotides such as deoxyribonucleic acid (DNA), and, where appropriate, ribonucleic acid (RNA). The term should also be understood to include, as equivalents, analogs of either RNA or DNA made from nucleotide analogs, and, as applicable to the embodiment being described, single (sense or antisense) and double-stranded polynucleotides. ESTs, chromosomes, cDNAs, mRNAs, and rRNAs are representative examples of molecules that may be referred to as nucleic acids.

The term "nucleotide sequence complementary to the nucleotide sequence of SEQ ID NO. x" refers to the nucleotide sequence of the complementary strand of a nucleic acid strand having SEQ ID NO. x. The term "complementary strand" is used herein interchangeably with the term "complement". The complement of a nucleic acid strand can be the complement of a coding strand or the complement of a non-coding strand.

The term "polymorphism" refers to the coexistence of more than one form of a gene or portion (e.g., allelic variant) thereof. A portion of a gene of which there are at least two different forms, i.e., two different nucleotide sequences, is referred to as a "polymorphic region of a gene". A polymorphic region can be a single nucleotide, the identity of which differs in different alleles. A polymorphic region can also be several nucleotides long.

A "polymorphic gene" refers to a gene having at least one polymorphic region.

As used herein, the term "promoter" means a DNA sequence that regulates expression of a selected DNA sequence operably linked to the promoter, and which effects expression of the selected DNA sequence in cells. The term encompasses "tissue specific" promoters, i.e., promoters which effect expression of the selected DNA sequence only in specific cells (e.g., cells of a specific tissue). The term also covers so-called "leaky" promoters, which regulate expression of a selected DNA primarily in one tissue, but cause expression in other tissues as well. The term also encompasses non-tissue specific promoters and promoters that constitutively expressed or that are inducible (i.e., expression levels can be controlled).

The terms "protein", "polypeptide", and "peptide" are used interchangeably herein when referring to a gene product.

The term "recombinant protein" refers to a polypeptide of the present invention which is produced by recombinant DNA techniques, wherein generally, DNA encoding a polypeptide is inserted into a suitable expression vector which is in turn used to transform a host cell to produce the heterologous protein. Moreover, the phrase "derived from", with respect to a recombinant gene, is meant to include within the meaning of "recombinant protein" those proteins having an amino acid sequence of a native polypeptide, or an amino acid sequence similar thereto which is generated by mutations including substitutions and deletions (including truncation) of a naturally occurring form of the polypeptide.

"Small molecule" as used herein, is meant to refer to a composition, which has a molecular weight of less than about 5 kD and most preferably less than about 4 kD. Small molecules can be nucleic acids, peptides, polypeptides, peptidomimetics, carbohydrates, lipids or other organic (carbon-containing) or inorganic molecules. Many pharmaceutical companies have extensive libraries of chemical and/or biological mixtures, often fungal, bacterial, or algal extracts, which can be screened with any of the assays of the invention to identify compounds that modulate a bioactivity.

As used herein, the term "specifically hybridizes" or "specifically detects" refers to the ability of a nucleic acid molecule of the invention to hybridize to at least a portion of, for example approximately 6, 12, 15, 20, 30, 50, 100, 150, 200, 300, 350, 400, 500, 750, or 1000 contiguous nucleotides of a nucleic acid designated in any one of SEQ ID Nos 1, 3, 5, or 7, or a sequence complementary thereto, or naturally occurring mutants thereof, such that it has less than about 15%, preferably less than about 10%, and more preferably less than about 5% background hybridization to a cellular nucleic acid (e.g., mRNA or genomic DNA) encoding a different protein. In preferred embodiments, the oligonucleotide probe detects only a specific nucleic acid, e.g., it does not substantially hybridize to similar or related nucleic acids, or complements thereof.

"Transcriptional regulatory sequence" is a generic term used throughout the specification to refer to DNA sequences, such as initiation signals, enhancers, and promoters, which induce or control transcription of protein coding sequences with which they are operably linked. In preferred embodiments, transcription of one of the genes is under the control of a promoter sequence (or other transcriptional regulatory sequence) which controls the expression of the recombinant gene in a cell-type in which expression is intended. It will also be understood that the recombinant gene can be under the control of transcriptional regulatory sequences which are the same or which are different from those sequences which control transcription of the naturally occurring forms of the polypeptide.

As used herein, the term "transfection" means the introduction of a nucleic acid, e.g., via an expression vector, into a recipient cell by nucleic acid-mediated gene transfer. "Transformation", as used herein, refers to a process in which a cell's genotype is changed as a result of the cellular uptake of exogenous DNA or RNA, and, for example, the transformed cell expresses a recombinant form of a polypeptide or, in the case of anti-sense expression from the transferred gene, the expression of the target gene is disrupted.

As used herein, the term "transgene" means a nucleic acid sequence (or an antisense transcript thereto) which has been introduced into a cell. A transgene could be partly or entirely heterologous, i.e., foreign, to the transgenic animal or cell into which it is introduced, or, is homologous to an endogenous gene of the transgenic animal or cell into which it is introduced, but which is designed to be inserted, or is inserted, into the animal's genome in such a way as to alter the genome of the cell into which it is inserted (e.g., it is inserted at a location which differs from that of the natural gene or its insertion results in a knockout). A transgene can also be present in a cell in the form of an episome. A transgene can include one or more transcriptional regulatory sequences and any other nucleic acid, such as introns, that may be necessary for optimal expression of a selected nucleic acid.

A "transgenic animal" refers to any animal, preferably a non-human mammal, bird or an amphibian, in which one or more of the cells of the animal contain heterologous nucleic acid introduced by way of human intervention, such as by transgenic techniques well known in the art. The nucleic acid is introduced into the cell, directly or indirectly by introduction into a precursor of the cell, by way of deliberate genetic manipulation, such as by microinjection or by infection with a recombinant virus. The term genetic manipulation does not include classical crossbreeding, or in vitro fertilization, but rather is directed to the introduction of a recombinant DNA molecule. This molecule may be integrated within a chromosome, or it may be extra-chromosomally replicating DNA. In the typical transgenic animals described herein, the transgene causes cells to express a recombinant form of one of the subject polypeptide, e.g. either agonistic or antagonistic forms. However, transgenic animals in which the recombinant gene is silent are also contemplated, as for example, the FLP or CRE recombinase dependent constructs described below. Moreover, "transgenic animal" also includes those recombinant animals in which gene disruption of one or more genes is caused by human intervention, including both recombination and anti-sense techniques.

The term "treating" as used herein is intended to encompass curing as well as ameliorating at least one symptom of the condition or disease.

The term "vector" refers to a nucleic acid molecule capable of transporting another nucleic acid to which it has been linked. One type of preferred vector is an episome, i.e., a nucleic acid capable of extra-chromosomal replication. Preferred vectors are those capable of autonomous replication and/or expression of nucleic acids to which they are linked. Vectors capable of directing the expression of genes to which they are operatively linked are referred to herein as "expression vectors". In general, expression vectors of utility in recombinant DNA techniques are often in the form of "plasmids" which refer generally to circular double stranded DNA loops which, in their vector form are not bound to the chromosome. In the present specification, "plasmid" and "vector" are used interchangeably as the plasmid is the most commonly used form of vector. However, the invention is intended to include such other forms of expression vectors which serve equivalent functions and which become known in the art subsequently hereto.

The term "wild-type allele" refers to an allele of a gene which, when present in two copies in a subject results in a wild-type phenotype. There can be several different wild-type alleles of a specific gene, since certain nucleotide changes in a gene may not affect the phenotype of a subject having two copies of the gene with the nucleotide changes.

III. Nucleic Acids of the Present Invention

As described below, one aspect of the invention pertains to isolated nucleic acids, variants, and/or equivalents of such nucleic acids.

Nucleic acids of the present invention have been identified as differentially expressed in tumor cells, e.g., colon cancer-derived cell lines (relative to the expression levels in normal tissue, e.g., normal colon tissue and/or normal non-colon tissue), such as SEQ ID Nos. 1, 3, 5, or 7, a sequence complementary thereto, or a sequence which specifically hybridizes to a sequence of SEQ ID No. 1, 3, 5, or 7. In certain embodiments, the subject nucleic acids are differentially expressed by at least about 0.5 fold, at least about 2 fold, at least about 5 fold, at least about 20 fold, or at least about 50 fold. Preferred nucleic acids include sequences identified as differentially expressed both in colon cancer cell tissue and colon cancer cell lines. In preferred embodiments, nucleic acids of the present invention are upregulated in tumor cells, especially colon cancer tissue and/or colon cancer-derived cell lines. In another embodiment, nucleic acids of the present invention are downregulated in tumor cells, especially colon cancer tissue and/or colon cancer-derived cell lines.

Genes which are upregulated, such as oncogenes, or downregulated, such as tumor suppressors, in aberrantly proliferating cells may be targets for diagnostic or therapeutic techniques. For example, upregulation of the cdc2 gene induces mitosis. Overexpression of the myt1 gene, a mitotic deactivator, negatively regulates the activity of cdc2. Aberrant proliferation may thus be induced either by upregulating cdc2 or by downregulating myt1. Similarly, downregulation of tumor suppressors such as p53 and Rb have been implicated in tumorigenesis.

Still other preferred nucleic acids of the present invention encode a polypeptide comprising at least a portion of a polypeptide encoded by one of SEQ ID Nos. 1, 3, 5, or 7. For example, preferred nucleic acid molecules for use as probes/primers or antisense molecules (i.e., noncoding nucleic acid molecules) can comprise a region of a nucleic acid sequence of SEQ ID Nos 1, 3, 5, or 7 sufficient to hybridize with a nucleic acid substantialy complementary to the sequence of SEQ ID Nos 1, 3, 5, or 7. Preferred nucleic acid molecules for use as probes/primers can further comprise a region of nucleic acid sequence substantially complementary to the sequence of SEQ ID Nos. 1, 3, 5, or 7 sufficient to hybridize with the sequence of SEQ ID Nos. 1, 3, 5, or 7. The nucleic acid sequences of the present invention for use as probes/primers are preferably at least about 12, 20, 30, 50, 60, 70, 80, 90, or 100 base pairs in length up to the length of the complete gene. Coding nucleic acid molecules can comprise, for example, from about 50, 60, 70, 80, 90, or 100 base pairs up to the length of the complete gene.

Another aspect of the invention provides a nucleic acid which hybridizes under low, medium, or high stringency conditions to a nucleic acid sequence represented by one of SEQ ID Nos. 1, 3, 5, or 7, or a sequence complementary thereto. Appropriate stringency conditions which promote DNA hybridization, for example, 6.0×sodium chloride/sodium citrate (SSC) at about 45° C., followed by a wash of 2.0×SSC at 50° C., are known to those skilled in the art or can be found in Current Protocols in Molecular Biology, John Wiley & Sons, N.Y. (1989), 6.3.1–12.3.6. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C. Both temperature and salt may be varied, or temperature or salt concentration may be held constant while the other variable is changed. In a preferred embodiment, a nucleic acid of the present invention will bind to one of SEQ ID Nos. 1, 3, 5, or 7, or a sequence complementary thereto, under moderately stringent conditions, for example at about 2.0×SSC and about 40° C. In a particularly preferred embodiment, a nucleic acid of the present invention will bind to one of SEQ ID Nos. 1, 3, 5, or 7, or a sequence complementary thereto, under high stringency conditions.

In one embodiment, the invention provides nucleic acids which hybridize under low stringency conditions of 6×SSC at room temperature followed by a wash at 2×SSC at room temperature.

In another embodiment, the invention provides nucleic acids which hybridize under high stringency conditions of 2×SSC at about 65° C. followed by a wash at 0.2×SSC at about 65° C.

Nucleic acids having a sequence that differs from the nucleotide sequences shown in one of SEQ ID Nos. 1, 3, 5, or 7, or a sequence complementary thereto, due to degeneracy in the genetic code, are also within the scope of the invention. Such nucleic acids encode functionally equivalent peptides (i.e., a peptide having equivalent or similar biological activity) but differ in sequence from the sequence shown in the sequence listing due to degeneracy in the genetic code. For example, a number of amino acids are designated by more than one triplet. Codons that specify the same amino acid, or synonyms (for example, CAU and CAC each encode histidine) may result in "silent" mutations which do not affect the amino acid sequence of a polypeptide. However, it is expected that DNA sequence polymorphisms that do lead to changes in the amino acid sequences of the subject polypeptides will exist among mammals. One skilled in the art will appreciate that these variations in one or more nucleotides (e.g., up to about 3–5% of the nucleotides) of the nucleic acids encoding polypeptides having an activity of a polypeptide may exist among individuals of a given species due to natural allelic variation.

Also within the scope of the invention are nucleic acids encoding splicing variants of proteins encoded by a nucleic acid of SEQ ID Nos. 1, 3, 5, or 7, or a sequence complementary thereto, or natural homologs of such proteins. Such homologs can be cloned by hybridization or PCR, as further described herein.

The polynucleotide sequence may also encode for a leader sequence, e.g., the natural leader sequence or a heterologous leader sequence, for a subject polypeptide. For example, the desired DNA sequence may be fused in the same reading frame to a DNA sequence which aids in expression and secretion of the polypeptide from the host cell, for example, a leader sequence which functions as a secretory sequence for controlling transport of the polypeptide from the cell. The protein having a leader sequence is a preprotein and may have the leader sequence cleaved by the host cell to form the mature form of the protein.

The polynucleotide of the present invention may also be fused in frame to a marker sequence, also referred to herein as "Tag sequence" encoding a "Tag peptide", which allows for marking and/or purification of the present invention. In a preferred embodiment, the market sequence is a hexahistidine tag, e g, supplied by a PQE-9 vector. Numerous other Tag peptides are available commercially Other frequently used Tags include myc-epitopes (e g, see Ellison et al. (1991) J Biol hem 266:21150–21157) which includes a 10-residue sequence from c-myc, the pFLAG system (International Biotechnologies, Inc.), the pEZZ-protein A system (Pharmacia, N.J.), and a 16 amino acid portion of the *Haemophilus influenza* hemagglutinin protein. Furthermore, any polypeptide can be used as a Tag so long as a reagent, e.g., an antibody interacting specifically with the Tag polypeptide is available or can be prepared or identified.

As indicated by the examples set out below, nucleic acids can be obtained from mRNA present in any of a number of eukaryotic cells, e.g., and are preferably obtained from metazoan cells, more preferably from vertebrate cells, and even more preferably from mammalian cells. It should also be possible to obtain nucleic acids of the present invention from genomic DNA from both adults and embryos. For example, a gene can be cloned from either a cDNA or a genomic library in accordance with protocols generally known to persons skilled in the art. cDNA can be obtained by isolating total mRNA from a cell, e.g., a vertebrate cell, a mammalian cell, or a human cell, including embryonic cells. Double stranded cDNAs can then be prepared from the total mRNA, and subsequently inserted into a suitable plasmid or bacteriophage vector using any one of a number of known techniques. The gene can also be cloned using established polymerase chain reaction techniques in accordance with the nucleotide sequence information provided by the invention.

The invention includes within its scope a polynucleotide having the nucleotide sequence of nucleic acid obtained from this biological material, wherein the nucleic acid hybridizes under stringent conditions (at least about 4×SSC at 65° C., or at least about 4×SSC at 42° C.; see, for example, U.S. Pat. No. 5,707,829, incorporated herein by reference) with at least 15 contiguous nucleotides of at least one of SEQ ID Nos. 1, 3, 5, or 7. By this is intended that when at least 15 contiguous nucleotides of one of SEQ ID Nos. 1, 3, 5, or 7 is used as a probe, the probe will preferentially hybridize with a gene or mRNA (of the biological material) comprising the complementary sequence, allowing the identification and retrieval of the nucleic acids of the biological material that uniquely hybridize to the selected probe. Probes from more than one of SEQ ID Nos. 1, 3, 5, or 7 will hybridize with the same gene or mRNA if the cDNA from which they were derived corresponds to one mRNA. Probes of more than 15 nucleotides can be used, but 15 nucleotides represents enough sequence for unique identification.

In another embodiment the nucleic acids are isolated from libraries prepared from normal colon specific tissue. Techniques for producing and probing nucleic acid sequence libraries are described, for example, in Sambrook et al., "Molecular Cloning: A Laboratory Manual" (New York, Cold Spring Harbor Laboratory, 1989). The cDNA can be prepared by using primers based on a sequence from SEQ ID Nos. 1, 3, 5, or 7. In one embodiment, the cDNA library can be made from only poly-adenylated mRNA. Thus, poly-T primers can be used to prepare cDNA from the mRNA. Alignment of SEQ ID Nos. 1, 3, 5, or 7 can result in identification of a related polypeptide or polynucleotide. Some of the polynucleotides disclosed herein contains repetitive regions that were subject to masking during the search procedures. The information about the repetitive regions is discussed below.

Constructs of polynucleotides having sequences of SEQ ID Nos. 1, 3, 5, or 7, or sequences complementary thereto can be generated synthetically. Alternatively, single-step assembly of a gene and entire plasmid from large numbers of oligodeoxyribonucleotides is described by Stemmer et at, Gene (Amsterdam) (1995) 164(i):49–53. In this method, assembly PCR (the synthesis of long DNA sequences from large numbers of oligodeoxyribonucleotides (oligos)) is described. The method is derived from DNA shuffling (Stemmer, Nature (1994) 370:389–391), and does not rely on DNA ligase, but instead relies on DNA polymerase to build increasingly longer DNA fragments during the assembly process. For example, a 1.1-kb fragment containing the TEM-1 beta-lactamase-encoding gene (bla) can be assembled in a single reaction from a total of 56 oligos, each 40 nucleotides (nt) in length. The synthetic gene can be PCR amplified and cloned in a vector containing the tetracycline-resistance gene (Tc-R) as the sole selectable marker. Without relying on ampicillin (Ap) selection, 76% of the Tc-R colonies were Ap-R, making this approach a general method for the rapid and cost-effective synthesis of any gene.

IV. Identification of Functional and Structural Motifs of Novel Genes Using Art-Recognized Methods Translations of the nucleotide sequence of the nucleic acids, cDNAs, or full genes can be aligned with individual known sequences. Similarity with individual sequences can be used to determine the activity of the polypeptides encoded by the polynucleotides of the invention. For example, sequences that show similarity with a chemokine sequence may exhibit chemokine activities. Also, sequences exhibiting similarity with more than one individual sequence may exhibit activities that are characteristic of either or both individual sequences.

The full length sequences and fragments of the polynucleotide sequences of the nearest neighbors can be used as probes and primers to identify and isolate the full length sequence of the nucleic acid. The nearest neighbors can indicate a tissue or cell type to be used to construct a library for the full-length sequences of the nucleic acid.

Typically, the nucleic acids are translated in all six frames to determine the best alignment with the individual sequences. The sequences disclosed herein in the Sequence Listing are in a 5' to 3' orientation and translation in three frames can be sufficient (with a few specific exceptions as described in the Examples). These amino acid sequences are referred to, generally, as query sequences, which will be aligned with the individual sequences.

Nucleic acid sequences can be compared with known genes by any of the methods disclosed above. Results of individual and query sequence alignments can be divided into three categories: high similarity, weak similarity, and no similarity. Individual alignment results ranging from high similarity to weak similarity provide a basis for determining polypeptide activity and/or structure.

Parameters for categorizing individual results include: percentage of the alignment region length where the strongest alignment is found, percent sequence identity, and p value.

The percentage of the alignment region length is calculated by counting the number of residues of the individual sequence found in the region of strongest alignment. This number is divided by the total residue length of the query sequence to find a percentage. An example is shown below:

| Query Sequence: | $AA_1$ $AA_2$ $AA_3$ $AA_4$ $AA_5$ $AA_6$ $AA_7$ $AA_8$ $AA_9$ $AA_{10}$ $AA_{11}$ $AA_{12}$ $AA_{13}$ $AA_{14}$ $AA_{15}$ $AA_{16}$ $AA_{17}$ $AA_{18}$ $AA_{19}$ $AA_{20}$ |
| --- | --- |
| Individual Sequence: | $AA_1$ $AA_2$ $AA_3$ $AA_4$ $AA_5$ $AA_6$ $AA_7$ $AA_8$ $AA_9$ $AA_{10}$ $AA_{11}$ $AA_{12}$ $AA_{13}$ $AA_{14}$ $AA_{15}$ $AA_{16}$ $AA_{17}$ $AA_{18}$ $AA_{19}$ |

The region of alignment begins at amino acid 9 and ends at amino acid 19. The total length of the query sequence is 20 amino acids. The percent of the alignment region length is 11/20 or 55%.

Percent sequence identity is calculated by counting the number of amino acid matches between the query and individual sequence and dividing total number of matches by the number of residues of the individual sequence found in the region of strongest alignment. For the example above, the percent identity would be 10 matches divided by 11 amino acids, or approximately 90.9%.

P value is the probability that the alignment was produced by chance. For a single alignment, the p value can be calculated according to Karlin et al., *Proc. Natl. Acad. Sci.* 87: 2264 (1990) and Karlin et al., *Proc. Natl. Acad. Sci.* 90: (1993). The p value of multiple alignments using the same query sequence can be calculated using an heuristic approach described in Altschul et al., *Genet.* 6:119(1994). Alignment programs such as BLAST program can calculate the p value.

The boundaries of the region where the sequences align can be determined according to Doolittle, Methods in Enzymology, supra; BLAST or FASTA programs; or by determining the area where the sequence identity is highest.

Another factor to consider for determining identity or similarity is the location of the similarity or identity. Strong local alignment can indicate similarity even if the length of alignment is short. Sequence identity scattered throughout the length of the query sequence also can indicate a similarity between the query and profile sequences.

High Similarity

For the alignment results to be considered high similarity, the percent of the alignment region length, typically, is at least about 55% of total length query sequence; more typically, at least about 58%; even more typically; at least about 60% of the total residue length of the query sequence. Usually, percent length of the alignment region can be as much as about 62%; more usually, as much as about 64%; even more usually, as much as about 66%.

Further, for high similarity, the region of alignment, typically, exhibits at least about 75% of sequence identity; more typically, at least about 78%; even more typically; at least about 80% sequence identity. Usually, percent sequence identity can be as much as about 82%; more usually, as much as about 84%; even more usually, as much as about 86%.

The p value is used in conjunction with these methods. If high similarity is found, the query sequence is considered to have high similarity with a profile sequence when the p value is less than or equal to about $10^{-2}$; more usually; less than or equal to about $10^{-3}$ even more usually; less than or equal to about $10^{-4}$. More typically, the p value is no more than about $10^{-5}$ more typically; no more than or equal to about $10^{-10}$; even more typically; no more than or equal to about $10^{-15}$ for the query sequence to be considered high similarity.

Weak Similarity

For the alignment results to be considered weak there is no minimum percent length of the alignment region no minimum length of alignment. A better showing of weak similarity is considered when the region of alignment is, typically, at least about 15 amino acid residues in length; more typically, at least about 20; even more typically; at least about 25 amino acid residues in length. Usually, length of the alignment region can be as much as about 30 amino acid residues; more usually, as much as about 40; even more usually, as much as about 60 amino acid residues.

Further, for weak similarity, the region of alignment, typically, exhibits at least about 35% of sequence identity; more typically, at least about 40%; even more typically; at least about 45% sequence identity. Usually, percent sequence identity can be as much as about 50%; more usually, as much as about 55%; even more usually, as much as about 60%.

If low similarity is found, the query sequence is considered to have weak similarity with a profile sequence when the p value is usually less than or equal to about $10^{-2}$; more usually; less than or equal to about $10^{-3}$ even more usually; less than or equal to about $10^{-4}$. More typically, the p value is no more than about $10^{-5}$ more usually; no more than or equal to about $10^{-10}$; even more usually; no more than or equal to about $10^{-15}$ for the query sequence to be considered weak similarity.

Similarity Determined by Sequence Identity

Sequence identity alone can be used to determine similarity of a query sequence to an individual sequence and can indicate the activity of the sequence. Such an alignment, preferably, permits gaps to align sequences. Typically, the query sequence is related to the profile sequence if the sequence identity over the entire query sequence is at least about 15%; more typically, at least about 20%; even more typically, at least about 25%; even more typically, at least about 50%. Sequence identity alone as a measure of similarity is most useful when the query sequence is usually, at least 80 residues in length; more usually, 90 residues; even more usually, at least 95 amino acid residues in length. More typically, similarity can be concluded based on sequence identity alone when the query sequence is preferably 100 residues in length; more preferably, 120 residues in length; even more preferably, 150 amino acid residues in length.

Determining Activity from Alignments with Profile and Multiple Aligned Sequences Translations of the nucleic acids can be aligned with amino acid profiles that define either protein families or common motifs. Also, translations of the nucleic acids can be aligned to multiple sequence alignments (MSA) comprising the polypeptide sequences of members of protein families or motifs. Similarity or identity with profile sequences or MSAs can be used to determine the activity of the polypeptides encoded by nucleic acids or corresponding cDNA or genes. For example, sequences that show an identity or similarity with a chemokine profile or MSA can exhibit chemokine activities.

Profiles can designed manually by (1) creating a MSA, which is an alignment of the amino acid sequence of members that belong to the family and (2) constructing a statistical representation of the alignment. Such methods are described, for example, in Birney et al., *Nucl. Acid Res.* 25(14): 2730–2739 (1996).

MSAs of some protein families and motifs are publicly available. For example, these include MSAs of 547 different families and motifs. These MSAs are described also in Sonnhammer et al., *Proteins* 28: 405–420 (1997). Other sources are also available in the world wide web. A brief description of these MSAs is reported in Pascarella et al., *Prot. Eng.* 9(3): 249–251 (1996).

Techniques for building profiles from MSAs are described in Sonnhammer et al., supra; Birney et al., supra; and *Methods in Enzymology*, vol. 266: "Computer Methods for Macromolecular Sequence Analysis," 1996, ed. Doolittle, Academic Press, Inc., a division of Harcourt Brace & Co., San Diego, Calif., USA.

Similarity between a query sequence and a protein family or motif can be determined by (a) comparing the query sequence against the profile and/or (b) aligning the query sequence with the members of the family or motif.

Typically, a program such as Searchwise can be used to compare the query sequence to the statistical representation of the multiple alignment, also known as a profile. The program is described in Birney et al., supra. Other techniques to compare the sequence and profile are described in Sonnhammer et al., supra and Doolittle, supra.

Next, methods described by Feng et al., *J. Mol. Evol.* 25:351–360 (1987) and Higgins et al., *CABIOS* 5:151–153 (1989) can be used align the query sequence with the members of a family or motif, also known as a MSA. Computer programs, such as PILEUP, can be used. See Feng et al., infra.

The following factors are used to determine if a similarity between a query sequence and a profile or MSA exists: (1) number of conserved residues found in the query sequence, (2) percentage of conserved residues found in the query sequence, (3) number of frameshifts, and (4) spacing between conserved residues.

Some alignment programs that both translate and align sequences can make any number of frameshifts when translating the nucleotide sequence to produce the best alignment. The fewer frameshifts needed to produce an alignment, the stronger the similarity or identity between the query and profile or MSAs. For example, a weak similarity resulting from no frameshifts can be a better indication of activity or structure of a query sequence, than a strong similarity resulting from two frameshifts.

Preferably, three or fewer frameshifts are found in an alignment; more preferably two or fewer frameshifts; even more preferably, one or fewer frameshifts; even more preferably, no frameshifts are found in an alignment of query and profile or MSAs.

Conserved residues are those amino acids that are found at a particular position in all or some of the family or motif members. For example, most known chemokines contain four conserved cysteines. Alternatively, a position is considered conserved if only a certain class of amino acids is found in a particular position in all or some of the family members. For example, the N-terminal position may contain a positively charged amino acid, such as lysine, arginine, or histidine.

Typically, a residue of a polypeptide is conserved when a class of amino acids or a single amino acid is found at a particular position in at least about 40% of all class members; more typically, at least about 50%; even more typically, at least about 60% of the members. Usually, a residue is conserved when a class or single amino acid is found in at least about 70% of the members of a family or motif; more usually, at least about 80%; even more usually, at least about 90%; even more usually, at least about 95%.

A residue is considered conserved when three unrelated amino acids are found at a particular position in the some or all of the members; more usually, two unrelated amino acids. These residues are conserved when the unrelated amino acids are found at particular positions in at least about 40% of all class member, more typically, at least about 50%; even more typically, at least about 60% of the members. Usually, a residue is conserved when a class or single amino acid is found in at least about 70% of the members of a family or motif more usually, at least about 80%; even more usually, at least about 90%; even more usually, at least about 95%.

A query sequence has similarity to a profile or MSA when the query sequence comprises at least about 25% of the conserved residues of the profile or MSA; more usually, at least about 30%; even more usually; at least about 40%. Typically, the query sequence has a stronger similarity to a profile sequence or MSA when the query sequence comprises at least about 45% of the conserved residues of the profile or MSA more typically, at least about 50%; even more typically; at least about 55%.

V. Probes and Primers

The nucleotide sequences determined from the cloning of genes from tumor cells, especially colon cancer cell lines and tissues will further allow for the generation of probes and primers designed for identifying and/or cloning homologs in other cell types, e.g., from other tissues, as well as homologs from other mammalian organisms. Nucleotide sequences useful as probes/primers may include all or a portion of the sequences listed in SEQ ID Nos. 1, 3, 5, or 7 or sequences complementary thereto, or sequences which hybridize under stringent conditions to all or a portion of SEQ ID Nos. 1, 3, 5, or 7. For instance, the present invention also provides a probe/primer comprising a substantially purified oligonucleotide, which oligonucleotide comprising a nucleotide sequence that hybridizes under stringent conditions to at least approximately 8, preferably about 12, preferably about 15, preferably about 25, more preferably about 40 consecutive nucleotides up to the full length of the sense or anti-sense sequence selected from the group consisting of SEQ ID Nos. 1, 3, 5, or 7, or a sequence complementary thereto, or naturally occurring mutants thereof. For instance, primers based on a nucleic acid represented in SEQ ID Nos. 1, 3, 5, or 7, or a sequence complementary thereto, can be used in PCR reactions to clone homologs of that sequence.

In yet another embodiment, the invention provides probes/primers comprising a nucleotide sequence that hybridizes under moderately stringent conditions to at least approximately 8, preferably about 12, preferably about 15, preferably about 25, more preferably about 40 consecutive nucleotides up to the full length of the sense or antisense sequence selected from the group consisting of SEQ ID Nos. 1, 3, 5, or 7, or naturally occurring mutants thereof.

In particular, these probes are useful because they provide a method for detecting mutations in wild-type genes of the present invention. Nucleic acid probes which are complementary to a wild-type gene of the present invention and can form mismatches with mutant genes are provided, allowing for detection by enzymatic or chemical cleavage or by shifts in electrophoretic mobility. Likewise, probes based on the subject sequences can be used to detect transcripts or genomic sequences encoding the same or homologous proteins, for use, for example, in prognostic or diagnostic assays. In preferred embodiments, the probe further comprises a label group attached thereto and able to be detected, e.g., the label group is selected from radioisotopes, fluorescent compounds, chemiluminescent compounds, enzymes, and enzyme co-factors.

Full-length cDNA molecules comprising the disclosed nucleic acids are obtained as follows. A subject nucleic acid or a portion thereof comprising at least approximately 8, preferably about 12, preferably about 15, preferably about 25, more preferably about 40 nucleotides up to the full length of a sequence represented in SEQ ID Nos. 1, 3, 5, or 7, or a sequence complementary thereto, may be used as a hybridization probe to detect hybridizing members of a cDNA library using probe design methods, cloning methods, and clone selection techniques as described in U.S. Pat. No. 5,654,173, "Secreted Proteins and Polynucleotides Encoding Them," incorporated herein by reference. Libraries of cDNA may be made from selected tissues, such as normal or tumor tissue, or from tissues of a mammal treated with, for example, a pharmaceutical agent. Preferably, the tissue is the same as that used to generate the nucleic acids, as both the nucleic acid and the cDNA represent expressed genes. Most preferably, the cDNA library is made from the biological material described herein in the Examples. Alternatively, many cDNA libraries are available commercially. (Sambrook et al., Molecular Cloning: A Laboratory Manual, 2nd Ed. (Cold Spring Harbor Press, Cold Spring Harbor, N.Y. 1989). The choice of cell type for library construction may be made after the identity of the protein encoded by the nucleic acid-related gene is known. This will indicate which tissue and cell types are likely to express the related gene, thereby containing the mRNA for generating the cDNA.

Members of the library that are larger than the nucleic acid, and preferably that contain the whole sequence of the native message, may be obtained. To confirm that the entire cDNA has been obtained, RNA protection experiments may be performed as follows. Hybridization of a full-length cDNA to an mRNA may protect the RNA from RNase degradation. If the cDNA is not full length, then the portions of the mRNA that are not hybridized may be subject to RNase degradation. This may be assayed, as is known in the art, by changes in electrophoretic mobility on polyacrylamide gels, or by detection of released monoribonucleotides. Sambrook et al., Molecular Cloning: A Laboratory Manual, 2nd Ed. (Cold Spring Harbor Press, Cold Spring Harbor, N.Y. 1989). In order to obtain additional sequences 5' to the end of a partial cDNA, 5' RACE (PCR Protocols: A Guide to Methods and Applications (Academic Press, Inc. 1990)) may be performed.

Genomic DNA may be isolated using nucleic acids in a manner similar to the isolation of full-length cDNAs. Briefly, the nucleic acids, or portions thereof, may be used as probes to libraries of genomic DNA. Preferably, the library is obtained from the cell type that was used to generate the nucleic acids. Most preferably, the genomic DNA is obtained from the biological material described herein in the Example. Such libraries may be in vectors suitable for carrying large segments of a genome, such as P1 or YAC, as described in detail in Sambrook et al., 9.4–9.30. In addition, genomic sequences can be isolated from human BAC libraries, which are commercially available from Research Genetics, Inc., Huntville, Ala., USA, for example. In order to obtain additional 5' or 3' sequences, chromosome walking may be performed, as described in Sambrook et al., such that adjacent and overlapping fragments of genomic DNA are isolated. These may be mapped and pieced together, as is known in the art, using restriction digestion enzymes and DNA ligase.

Using the nucleic acids of the invention, corresponding full length genes can be isolated using both classical and PCR methods to construct and probe cDNA libraries. Using either method, Northern blots, preferably, may be performed on a number of cell types to determine which cell lines express the gene of interest at the highest rate.

Classical methods of constructing cDNA libraries in Sambrook et al., supra. With these methods, cDNA can be produced from mRNA and inserted into viral or expression vectors. Typically, libraries of mRNA comprising poly(A) tails can be produced with poly(T) primers. Similarly, cDNA libraries can be produced using the instant sequences as primers.

PCR methods may be used to amplify the members of a cDNA library that comprise the desired insert. In this case, the desired insert may contain sequence from the full length cDNA that corresponds to the instant nucleic acids. Such PCR methods include gene trapping and RACE methods.

Gene trapping may entail inserting a member of a cDNA library into a vector. The vector then may be denatured to produce single stranded molecules. Next, a substrate-bound probe, such a biotinylated oligo, may be used to trap cDNA inserts of interest. Biotinylated probes can be linked to an avidin-bound solid substrate. PCR methods can be used to amplify the trapped cDNA. To trap sequences corresponding to the full length genes, the labeled probe sequence may be based on the nucleic acids of the invention, e.g., SEQ ID Nos. 1, 3, 5, or 7, or a sequence complementary thereto. Random primers or primers specific to the library vector can be used to amplify the trapped cDNA. Such gene trapping techniques are described in Gruber et al., PCT WO 95/04745 and Gruber et al., U.S. Pat. No. 5,500,356. Kits are commercially available to perform gene trapping experiments from, for example, Life Technologies, Gaithersburg, Md., USA.

"Rapid amplification of cDNA ends," or RACE, is a PCR method of amplifying cDNAs from a number of different RNAs. The cDNAs may be ligated to an oligonucleotide linker and amplified by PCR using two primers. One primer may be based on sequence from the instant nucleic acids, for which full length sequence is desired, and a second primer may comprise a sequence that hybridizes to the oligonucleotide linker to amplify the cDNA. A description of this method is reported in PCT Pub. No. WO 97/19110.

In preferred embodiments of RACE, a common primer may be designed to anneal to an arbitrary adaptor sequence ligated to cDNA ends (Apte and Siebert, *Biotechniques* 15:890–893, 1993; Edwards et al., *Nuc. Acids Res.* 19:5227–5232, 1991). When a single gene-specific RACE primer is paired with the common primer, preferential amplification of sequences between the single gene specific primer and the common primer occurs. Commercial cDNA pools modified for use in RACE are available.

Another PCR-based method generates full-length cDNA library with anchored ends without specific knowledge of the cDNA sequence. The method uses lock-docking primers (1–VI), where one primer, poly TV (I–Ill) locks over the polyA tail of eukaryotic mRNA producing first strand synthesis and a second primer, polyGH (IV–VI) locks onto the polyC tail added by terminal deoxynucleotidyl transferase (TdT). This method is described in PCT Pub. No. WO 96/40998.

The promoter region of a gene generally is located 5' to the initiation site for RNA polymerase IL. Hundreds of promoter regions contain the "TATA" box, a sequence such as TATTA or TATAA, which is sensitive to mutations. The promoter region can be obtained by performing 5' RACE using a primer from the coding region of the gene. Alternatively, the cDNA can be used as a probe for the genomic sequence, and the region 5' to the coding region is identified by "walking up."

If the gene is highly expressed or differentially expressed, the promoter from the gene may be of use in a regulatory construct for a heterologous gene.

Once the full-length cDNA or gene is obtained, DNA encoding variants can be prepared by site-directed mutagenesis, described in detail in Sambrook 15.3–15.63. The choice of codon or nucleotide to be replaced can be based on the disclosure herein on optional changes in amino acids to achieve altered protein structure and/or function.

As an alternative method to obtaining DNA or RNA from a biological material, nucleic acid comprising nucleotides having the sequence of one or more nucleic acids of the invention can be synthesized. Thus, the invention encompasses nucleic acid molecules ranging in length from about 8 nucleotides (corresponding to at least 12 contiguous nucleotides which hybridize under stringent conditions to or are at least 80% identical to a nucleic acid represented by one of SEQ ID Nos. 1, 3, 5, or 7, or a sequence complementary thereto) up to a maximum length suitable for one or more biological manipulations, including replication and expression, of the nucleic acid molecule. The invention includes but is not limited to (a) nucleic acid having the size of a full gene, and comprising at least one of SEQ ID Nos. 1, 3, 5, or 7, or a sequence complementary thereto; (b) the nucleic acid of (a) also comprising at least one additional gene, operably linked to permit expression of a fusion protein; (c) an expression vector comprising (a) or (b); (d) a plasmid comprising (a) or (b); and (e) a recombinant viral particle comprising (a) or (b). Construction of (a) can be accomplished as described below in part IV.

The sequence of a nucleic acid of the present invention is not limited and can be any sequence of A, T, G, and/or C (for DNA) and A, U, 0, and/or C (for RNA) or modified bases thereof, including inosine and pseudouridine. The choice of sequence will depend on the desired function and can be dictated by coding regions desired, the intron-like regions desired, and the regulatory regions desired.

VI. Vectors Carrying Nucleic Acids of the Present Invention

The invention further provides plasmids and vectors, which can be used to express a gene in a host cell. The host cell may be any prokaryotic or eukaryotic cell. Thus, a nucleotide sequence derived from any one of SEQ ID Nos. 1, 3, 5, or 7, or a sequence complementary thereto, encoding all or a selected portion of a protein, can be used to produce a recombinant form of an polypeptide via microbial or eukaryotic cellular processes. Ligating the polynucleotide sequence into a gene construct, such as an expression vector, and transforming or transfecting into hosts, either eukaryotic (yeast, avian, insect or mammalian) or prokaryotic (bacterial cells), are standard procedures well known in the art.

Vectors that allow expression of a nucleic acid in a cell are referred to as expression vectors. Typically, expression vectors contain a nucleic acid operably linked to at least one transcriptional regulatory sequence. Regulatory sequences are art-recognized and are selected to direct expression of the subject nucleic acids. Transcriptional regulatory sequences are described in Goeddel; Gene Expression Technology: Methods in Enzymology 185, Academic Press, San Diego, Calif. (1990). In one embodiment, the expression vector includes a recombinant gene encoding a peptide having an agonistic activity of a subject polypeptide, or alternatively, encoding a peptide which is an antagonistic form of a subject polypeptide.

The choice of plasmid will depend on the type of cell in which propagation is desired and the purpose of propagation. Certain vectors are useful for amplifying and making large amounts of the desired DNA sequence. Other vectors are suitable for expression in cells in culture. Still other vectors are suitable for transfer and expression in cells in a whole animal or person. The choice of appropriate vector is well within the skill of the art. Many such vectors are available commercially. The nucleic acid or full-length gene is inserted into a vector typically by means of DNA ligase attachment to a cleaved restriction enzyme site in the vector. Alternatively, the desired nucleotide sequence may be inserted by homologous recombination in vivo. Typically this is accomplished by attaching regions of homology to the vector on the flanks of the desired nucleotide sequence. Regions of homology are added by ligation of oligonucleotides, or by polymerase chain reaction using primers comprising both the region of homology and a portion of the desired nucleotide sequence.

Nucleic acids or full-length genes are linked to regulatory sequences as appropriate to obtain the desired expression properties. These may include promoters (attached either at the 5' end of the sense strand or at the 3' end of the antisense strand), enhancers, terminators, operators, repressors, and inducers. The promoters may be regulated or constitutive. In some situations it may be desirable to use conditionally active promoters, such as tissue-specific or developmental stage-specific promoters. These are linked to the desired nucleotide sequence using the techniques described above for linkage to vectors. Any techniques known in the art may be used.

When any of the above host cells, or other appropriate host cells or organisms, are used to replicate and/or express the polynucleotides or nucleic acids of the invention, the resulting replicated nucleic acid, RNA, expressed protein or polypeptide, is within the scope of the invention as a product of the host cell or organism. The product is recovered by any appropriate means known in the art.

Once the gene corresponding to the nucleic acid is identified, its expression can be regulated in the cell to which the gene is native. For example, an endogenous gene of a cell can be regulated by an exogenous regulatory sequence as disclosed in U.S. Pat. No. 5,641,670, "Protein Production and Protein Delivery."

A number of vectors exist for the expression of recombinant proteins in yeast (see, for example, Broach et al (1983) in Experimental Manipulation of Gene Expression, ed. M. Inouye, Academic Press, p. 83, incorporated by reference herein). In addition, drug resistance markers such as ampicillin can be used. In an illustrative embodiment, a polypeptide is produced recombinantly utilizing an expression vector generated by sub-cloning one of the nucleic acids represented in one of SEQ ID Nos. 1, 3, 5, or 7, or a sequence complementary thereto.

The preferred mammalian expression vectors contain both prokaryotic sequences, to facilitate the propagation of the vector in bacteria, and one or more eukaryotic transcription units that are expressed in eukaryotic cells. The various methods employed in the preparation of plasmids and transformation of host organisms are well known in the art. For other suitable expression systems for both prokaryotic and eukaryotic cells, as well as general recombinant procedures, see Molecular Cloning: A Laboratory Manual, 2' Ed., ed. by Sambrook, Fritsch and Maniatis (Cold Spring Harbor Laboratory Press: 1989) Chapters 16 and 17.

When it is desirable to express only a portion of a gene, e.g., a truncation mutant, it may be necessary to add a start codon (ATG) to the oligonucleotide fragment containing the desired sequence to be expressed. It is well known in the art that a methionine at the N-terminal position can be enzymatically cleaved by the use of the enzyme methionine aminopeptidase (MAP). MAP has been cloned from *E. coli* (Ben-Bassat et al., (1987) *J. Bacteriol.* 169:751–757) and *Salmonella typhimurium* and its in vitro activity has been demonstrated on recombinant proteins (Miller et al. (1987) PNAS 84:2718–1722). Therefore, removal of an N-terminal methionine, if desired, can be achieved either in vivo by expressing polypeptides in a host which produces MAP (e.g., *E. coli* or CM89 or *S. cerevisiae*), or in vitro by use of purified MAP (e.g., procedure of Miller et al., supra).

Moreover, the nucleic acid constructs of the present invention can also be used as part of a gene therapy protocol to deliver nucleic acids such as antisense nucleic acids. Thus, another aspect of the invention features expression vectors for in vivo or in vitro transfection with an antisense oligonucleotide.

Nucleic acid molecules and constructs providing transgenes such as antisence oligonucleotides under the control of highly cell-type specific promoters and amplification promoter elements, can be incorporated into a vector and administered to any mammal, including a human. Many such vectors are commercially available, and other suitable vectors can be readily prepared and obvious to the skilled artisan. The exact design of the vector depends on such factors as the choice of the host cell to be transformed and/or the type of protein desired to be expressed. Suitable vectors can be produced by ligating the desired construct into a plasmid or viral vector suitable for expression in eukaryotic cells (see, for example, Broach, et al., Experimental Manipulation of Gene Expression, ed. M. Inouye (Academic Press, 1983) p. 83; Molecular Cloning: A Laboratory Manual, 2nd Ed., ed. Sambrook, et al. (Cold Spring Harbor Laboratory Press, 1989) Chapters 16 and 17, the entireties of which are incorporated by reference herein).

Examples of vectors that can be used include, but are not limited to, plasmids such as pBR322, pUC, or ColE1; adenovirus; Sindbis virus; simian virus 40; cytomegalovirus; and retroviral vectors such as murine sarcoma virus, mouse mammary tumor virus, Moloney murine leukemia virus, and Rous sarcoma virus. Bacterial vectors can be used, such as *Salmonella* ssp., *Yersinia enterocolitica, Shigella* spp., *Vibrio cholerae, Mycobacterium* strain BCG, and *Listeria monocytogenes*. Minichromosomes such as MC and MC1, bacteriophages, cosmids (plasmids into which phage lambda cos sites have been inserted) and replicons (genetic elements that are capable of independent extrachromosomal replication).

The vectors described above can additionally comprise sequences encoding one or more selectable markers, including, but not limited to, the gene that encodes dihydrofolate reductase and the genes that confer resistance to neomycin, tetracycline, ampicillin, chloramphenicol, kanamycin and streptomycin resistance. To improve incorporation into the genome of the target cell (if desired), a retroviral vector can be used, and long terminal repeat (LTR) sequences can be added on either side of the expression construct (see, e.g., Vile, et al., Virology 214: 307–313 (1995), the entirety of which is incorporated by reference herein).

Delivery of a nucleic acid construct comprising a nucleotide sequence of the present invention under the control of a highly cell-type specific promoter can be by any means known in the art, including oral or intranasal administration; intramuscular, intradermal, intraperitoneal, or subcutaneous injection, including injection using a biological ballistic gun ("gene gun"). Administration of the nucleic acid for therapeutic purposes can be repeated at any desired interval as needed to achieve therapeutic efficacy. Additional components can be added to a vector to improve its selective delivery to target cells and to repress its delivery to non-target cells. Examples of approaches that can be used include host range extension, entry enhancement, and host range restriction, as described in Peng and Russell, Cur. Opin. Biotech. 10: 454–457 (1999), the entirety of which is incorporated herein by reference.

In addition to viral transfer methods, non-viral methods can also be employed to introduce a subject nucleic acid, e.g., a sequence represented by one of SEQ ID Nos. 1, 3, 5, or 7, or a sequence complementary thereto, into the tissue of an animal. Most nonviral methods of gene transfer rely on normal mechanisms used by mammalian cells for the uptake and intracellular transport of macromolecules. In preferred embodiments, non-viral targeting means of the present invention rely on endocytic pathways for the uptake of the subject nucleic acid by the targeted cell. Exemplary targeting means of this type include liposomal derived systems, polylysine conjugates, and artificial viral envelopes.

A nucleic acid of any of SEQ ID Nos. 1, 3, 5, or 7, or a sequence complementary thereto, the corresponding cDNA, or the full-length gene may be used to express the partial or complete gene product. Appropriate nucleic acid constructs are purified using standard recombinant DNA techniques as described in, for example, Sambrook et al., (1989) *Molecular Cloning: A Laboratory Manual*, 2nd ed. (Cold Spring Harbor Press, Cold Spring Harbor, N.Y.), and under current regulations described in United States Dept. of HHS, National Institute of Health (NIH) Guidelines for Recombinant DNA Research. The polypeptides encoded by the nucleic acid may be expressed in any expression system, including, for example, bacterial, yeast, insect, amphibian and mammalian systems. Suitable vectors and host cells are described in U.S. Pat. No. 5,654,173.

Bacteria. Expression systems in bacteria include those described in Chang et al., *Nature* (1978) 275:615, Goeddel et al., *Nature* (1979) 281 :5, Goeddel et al., *Nucleic Acids Rec.* (1980) 8:4057; EP 0 036,776, U.S. Pat. No. 4,551,433, DeBoer et al., *Proc. Natl. Acad. Sci. (USA)* (1983) 80:2125, and Siebenlist et al., *Cell* (1980) 20:269.

Yeast. Expression systems in yeast include those described in Hinnen et al., *Proc. Natl. Acad. Sci. (USA)* (1978) 75:1929; Ito et al., *J. Bacteriol.* (1983) 153:163; Kurtz et al., *Mol. Cell. Biol.* (1986) 6:142; Kunze et al., *J. Basic Microbiol.* (1985) 25:141; Gleeson et al., *J. Gen. Microbiol.* (1986) 132:3459, Roggenkamp et al., *Mol. Gen. Genet.* (1986) 202:302) Das et al., *J. Bacteriol.* (1984) 158:1165; De Louvencourt et al., *J. Bacteriol.* (1983) 154: 737, Van den Berg et al., Bio/Technology (1990) 8:135; Kunze et al., J. Basic Microbiol. (1985) 25:141; Cregg et al., *Mol. Cell. Biol.* (1985) 5:3376, U.S. Pat. Nos. 4,837,148 and 4,929,555; Beach and Nurse, Nature (1981) 300:706; Davidow et al., Curr. Genet. (1985) 10:380, Gaillardin et al., Curr. Genet. (1985) 10:49, Ballance et al., *Biochem*. Biophys. Res. Commun. (1983) 112:284289; Tilburn et al., Gene (1983) 26:205221, Yelton et al., Proc. Natl. Acad. Sci. (USA) (1984) 81:14701474, Kelly and Hynes, EMBO J. (1985) 4:475479; EP 0 244,234, and WO 91/00357.

Insect Cells. Expression of heterologous genes in insects is accomplished as described in U.S. Pat. No. 4,745,051, Friesen et al., (1986) "The Regulation of Baculovirus Gene Expression" in: The Molecular Biology Of Baculoviruses (W. Doerfler, ed.), EP 0 127,839, EP 0 155,476, and Vlak et al., *J. Gen. Virol.* (1988) 69:765776, Miller et al., *Ann. Rev. Microbiol.* (1988) 42:177, Carbonell et al., *Gene* (1988) 73:409, Maeda et al., Nature (1985) 315:592594, Lebacq Verheyden et at., Mol. Cell. Biol. (1988) 8:3129; Smith et al., Proc. Nail. Acad. Sci. (USA) (1985) 82:8404, Miyajima et al., Gene (1987) 58:273; and Martin et al., DNA (1988) 7:99. Numerous baculoviral strains and variants and corresponding permissive insect host cells from hosts are described in Luckow et al., Bio/Technology (1988) 6:4755, Miller et al., Generic Engineering (Setlow, J. K. et al. eds.), Vol. 8 (Plenum Publishing, 1986), pp. 277279, and Maeda et al., Nature, (1985) 315:592–594.

Mammalian Cells. Mammalian expression is accomplished as described in Dijkema et al., EMBO J. (1985) 4:761, Gorman et al., Proc. Natl. Acad. Sci. (USA) (1982) 79:6777, Boshart et al., Cell (1985) 41:52 1 and U.S. Pat. No. 4,399,216. Other features of mammalian expression are facilitated as described in Ham and Wallace, Meth. Enz. (1979) 58:44, Barnes and Sato, Anal. Biochem. (1980) 102:255, U.S. Pat. Nos. 4,767,704, 4,657,866, 4,927,762, 4,560,655, WO 90/103430, WO 87/00195, and U.S. RE Pat. No. 30,985.

VII. Therapeutic Nucleic Acid Constructs

One aspect of the invention relates to the use of the isolated nucleic acid, e.g., SEQ ID Nos. 1, 3, 5, or 7, or a sequence complementary thereto, in antisense therapy. As used herein, antisense therapy refers to administration or in situ generation of oligonucleotide molecules or their derivatives which specifically hybridize (e.g., bind) under cellular conditions with the cellular mRNA and/or genomic DNA, thereby inhibiting transcription and/or translation of that gene. The binding may be by conventional base pair complementarity, or, for example, in the case of binding to DNA duplexes, through specific interactions in the major groove of the double helix. In general, antisense therapy refers to the range of techniques generally employed in the art, and includes any therapy which relies on specific binding to oligonucleotide sequences.

An antisense construct of the present invention can be delivered, for example, as an expression plasmid which, when transcribed in the cell, produces RNA which is complementary to at least a unique portion of the cellular mRNA. Alternatively, the antisense construct is an oligonucleotide probe which is generated ex vivo and which, when introduced into the cell, causes inhibition of expression by hybridizing with the mRNA and/or genomic sequences of a subject nucleic acid. Such oligonucleotide probes are preferably modified oligonucleotides which are resistant to endogenous nucleases, e.g., exonucleases and/or endonucleases, and are therefore stable in vivo. Exemplary nucleic acid molecules for use as antisense oligonucleotides are phosphoramidate, phosphorothioate and methylphosphonate analogs of DNA (see also U.S. Pat. Nos. 5,176,996; 5,264,564; and 5,256,775). Additionally, general approaches to constructing oligomers useful in antisense therapy have been reviewed, for example, by Van der Krol et al. (1988) BioTechniques 6:958–976; and Stein et al. (1988) Cancer Res 48:2659–2668. With respect to antisense DNA, oligodeoxyribonucleotides derived from the translation initiation site, e.g., between the −10 and +10 regions of the nucleotide sequence of interest, are preferred.

Antisense approaches involve the design of oligonucleotides (either DNA or RNA) that are complementary to mRNA. The antisense oligonucleotides will bind to the mRNA transcripts and prevent translation. Absolute complementarity, although preferred, is not required. In the case of double-stranded antisense nucleic acids, a single strand of the duplex DNA may thus be tested, or triplex formation may be assayed. The ability to hybridize will depend on both the degree of complementarity and the length of the antisense nucleic acid. Generally, the longer the hybridizing nucleic acid, the more base mismatches with an RNA it may contain and still form a stable duplex (or triplex, as the case may be). One skilled in the art can ascertain a tolerable degree of mismatch by use of standard procedures to determine the melting point of the hybridized complex.

Oligonucleotides that are complementary to the 5' end of the mRNA, e.g., the 5' untranslated sequence up to and including the AUG initiation codon, should work most efficiently at inhibiting translation. However, sequences complementary to the 3' untranslated sequences of mRNAs have recently been shown to be effective at inhibiting translation of mRNAs as well. (Wagner, R. 1994. Nature 372:333). Therefore, oligonucleotides complementary to either the 5' or 3' untranslated, non-coding regions of a gene could be used in an antisense approach to inhibit translation of endogenous mRNA. Oligonucleotides complementary to the 5' untranslated region of the mRNA should include the complement of the AUG start codon. Antisense oligonucleotides complementary to mRNA coding regions are typically less efficient inhibitors of translation but could also be used in accordance with the invention. Whether designed to hybridize to the 5', 3', or coding region of subject mRNA, antisense nucleic acids should be at least six nucleotides in length, and are preferably less that about 100 and more preferably less than about 50, 25, 17 or 10 nucleotides in length.

Regardless of the choice of target sequence, it is preferred that in vitro studies are first performed to quantitate the ability of the antisense oligonucleotide to quantitate the ability of the antisense oligonucleotide to inhibit gene expression. It is preferred that these studies utilize controls that distinguish between antisense gene inhibition and non-specific biological effects of oligonucleotides. It is also preferred that these studies compare levels of the target RNA or protein with that of an internal control RNA or protein. Additionally, it is envisioned that results obtained using the antisense oligonucleotide are compared with those obtained using a control oligonucleotide. It is preferred that the control oligonucleotide is of approximately the same length as the test oligonucleotide and that the nucleotide sequence of the oligonucleotide differs from the antisense sequence no more than is necessary to prevent specific hybridization to the target sequence.

The oligonucleotides can be DNA or RNA or chimeric mixtures or derivatives or modified versions thereof, single-stranded or double-stranded. The oligonucleotide can be modified at the base moiety, sugar moiety, or phosphate backbone, for example, to improve stability of the molecule, hybridization, etc. The oligonucleotide may include other appended groups such as peptides (e.g., for targeting host cell receptors), or agents facilitating transport across the cell membrane (see, e.g., Letsinger et al., 1989, Proc. Natl. Acad. Sci. U.S.A. 86:6553–6556; Lemaitre et al., 1987, Proc. Natl. Acad. Sci. 84:648–652; PCT Publication No. WO 88/098 10, published Dec. 15, 1988) or the blood-brain barrier (see, e.g., PCT Publication No. WO 89/10 134, published Apr. 25, 1988), hybridization-triggered cleavage agents (See, e.g., Krol et al., 1988, BioTechniques 6:958–976), or intercalating agents (See, e.g., Zon, 1988, Pharm. Res. 5:539–549). To this end, the oligonucleotide may be conjugated to another molecule, e.g., a peptide, hybridization triggered cross-linking agent, transport agent, hybridization-triggered cleavage agent, etc.

The antisense oligonucleotide may comprise at least one modified base moiety which is selected from the group including but not limited to 5-fluorouracil, 5-bromouracil, 5-chlorouracil, 5-iodouracil, hypoxanthine, xantine, 4-acetylcytosine, 5-(carboxyhydroxytriethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine.

The antisense oligonucleotide may also comprise at least one modified sugar moiety selected from the group including but not limited to arabinose, 2-fluoroarabinose, xylulose, and hexose.

The antisense oligonucleotide can also contain a neutral peptide-like backbone. Such molecules are termed peptide nucleic acid (PNA)-oligomers and are described, e.g., in Peny-O'Keefe et al. (1996) Proc. Natl. Acad. Sci. U.S.A. 93:14670 and in Eglom et al. (1993) Nature 365:566. One advantage of PNA oligomers is their capability to bind to complementary DNA essentially independently from the ionic strength of the medium due to the neutral backbone of the DNA. In yet another embodiment, the antisense oligonucleotide comprises at least one modified phosphate backbone selected from the group consisting of a phosphorothioate, a phosphorodithioate, a phosphoramidothioate, a phosphoramidate, a phosphordiamidate, a methyiphosphonate, an alkyl phosphotriester, and a formacetal or analog thereof.

In yet a further embodiment, the antisense oligonucleotide is an a-anomeric oligonucleotide. An a-anomeric oligonucleotide forms specific double-stranded hybrids with complementary RNA in which, contrary to the usual n-units, the strands run parallel to each other (Gautier et al, 1987, Nucl. Acids Res. 15:6625–6641). The oligonucleotide is a 2'-O-methylribonucleotide (Inoue et al., 1987, Nucl. Acids Res. 15:6131–12148), or a chimeric RNA-DNA analogue (Jnoue et al., 1987, FEBS Lett. 215:327–330).

Oligonucleotides of the invention may be synthesized by standard methods known in the art, e.g., by use of an automated DNA synthesizer (such as are commercially available from Biosearch, Applied Biosystems, etc.). As examples, phosphorothioate oligonucleotides may be synthesized by the method of Stein et al. (1988, Nucl. Acids Res. 16:3209), methylphosphonate olgonucleotides can be prepared by use of controlled pore glass polymer supports (Sarin et al., 1988, Proc. Natl. Acad. Sci. U.S.A. 85:7448–7451), etc.

While antisense nucleotides complementary to a coding region sequence can be used, those complementary to the transcribed untranslated region and to the region comprising the initiating methionine are most preferred.

The antisense molecules can be delivered to cells which express the target nucleic acid in vivo. A number of methods have been developed for delivering antisense DNA or RNA to cells; e.g., antisense molecules can be injected directly into the tissue site, or modified antisense molecules, designed to target the desired cells (e.g., antisense linked to peptides or antibodies that specifically bind receptors or antigens expressed on the target cell surface) can be administered systemically.

However, it is often difficult to achieve intracellular concentrations of the antisense sufficient to suppress translation on endogenous mRNAs. Therefore, a preferred approach utilizes a recombinant DNA construct in which the antisense oligonucleotide is placed under the control of a strong pol III or pol II promoter. The use of such a construct to transfect target cells in the patient will result in the transcription of sufficient amounts of single stranded RNAs that will form complementary base pairs with the endogenous transcripts and thereby prevent translation of the target mRNA. For example, a vector can be introduced in vivo such that it is taken up by a cell and directs the transcription of an antisense RNA. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others known in the art for replication and expression in mammalian cells. Expression of the sequence encoding the antisense RNA can be by any promoter known in the art to act in mammalian, preferably human cells. Such promoters can be inducible or constitutive. Such promoters include but are not limited to: the SV40 early promoter region (Bernoist and Chambon, 1981, Nature 290:304–310), the promoter contained in the 3' long terminal repeat of Rous sarcoma virus (Yamamoto et al., 1980, Cell 22:787–797), the herpes thymidine kinase promoter (Wagner et al., 1981, Proc. Natl. Acad. Sci. U.S.A. 78:1441–1445), the regulatory sequences of the metallothionein gene (Brinster et at, 1982, Nature 296:39–42), etc. Any type of plasmid, cosmid, YAC or viral vector can be used to prepare the recombinant DNA construct which can be introduced directly into the tissue site; e.g., the choroid plexus or hypothalamus. Alternatively, viral vectors can be used which selectively infect the desired tissue (e.g., for brain, herpesvirus vectors may be used), in which case administration may be accomplished by another route (e.g., systemically).

In another aspect of the invention, ribozyme molecules designed to catalytically cleave target mRNA transcripts can be used to prevent translation of target mRNA and expression of a target protein (See, e.g., PCT International Publication WO90/11364, published Oct. 4, 1990; Sarver et al., 1990, Science 247:1222–1225 and U.S. Pat. No. 5,093,246). While ribozymes that cleave mRNA at site specific recognition sequences can be used to destroy target mRNAs, the use of hammerhead ribozymes is preferred. Hammerhead ribozymes cleave mRNAs at locations dictated by flanking regions that form complementary base pairs with the target mRNA. The sole requirement is that the target mRNA have the following sequence of two bases: 5'-UG-3'. The construction and production of hammerhead ribozymes is well known in the art and is described more fully in Haseloff and Gerlach, 1988, Nature, 334:585–591. Preferably the ribozyme is engineered so that the cleavage recognition site is located near the 5' end of the target mRNA; i.e., to increase efficiency and minimize the intracellular accumulation of non-functional mRNA transcripts.

The ribozymes of the present invention also include RNA endoribonucleases (hereinafter "Cech-type ribozymes") such as the one which occurs naturally in *Tetrahymena thermophila* (known as the IVS, or L-19 IVS RNA) and which has been extensively described by Thomas Cech and collaborators (Zaug, et al., 1984, Science, 224:574–578; Zaug and Cech, 1986, Science, 231:470–475; Zaug, et al., 1986, Nature, 324:429–433; published International patent application No. WO88/04300 by University Patents Inc.; Been and Cech, 1986, Cell, 47:207–216). The Cech-type ribozymes have an eight base pair active site which hybridizes to a target RNA sequence whereafter cleavage of the target RNA takes place. The invention encompasses those Cech-type ribozymes which target eight base-pair active site sequences that are present in a target gene.

As in the antisense approach, the ribozymes can be composed of modified oligonucleotides (e.g., for improved stability, targeting, etc.) and should be delivered to cells which express the target gene in vivo. A preferred method of delivery involves using a DNA construct "encoding" the ribozyme under the control of a strong constitutive pol III or pol II promoter, so that transfected cells will produce sufficient quantities of the ribozyme to destroy endogenous messages and inhibit translation. Because ribozymes, unlike antisense molecules, are catalytic, a lower intracellular concentration is required for efficiency.

Antisense RNA, DNA, and ribozyme molecules of the invention may be prepared by any method known in the art for the synthesis of DNA and RNA molecules. These include techniques for chemically synthesizing oligodeoxyribonucleotides and oligoribonucleotides well known in the art such as for example solid phase phosphoramidite chemical synthesis. Alternatively, RNA molecules may be generated by in vitro and in vivo transcription of DNA sequences encoding the antisense RNA molecule. Such DNA sequences may be incorporated into a wide variety of vectors which incorporate suitable RNA polymerase promoters such as the T7 or SP6 polymerase promoters. Alternatively, antisense cDNA constructs that synthesize antisense RNA constitutively or inducibly, depending on the promoter used, can be introduced stably into cell lines.

Moreover, various well-known modifications to nucleic acid molecules may be introduced as a means of increasing intracellular stability and half-life. Possible modifications include but are not limited to the addition of flanking sequences of ribonucleotides or deoxyribonucleotides to the 5' and/or 3' ends of the molecule or the use of phosphorothioate or 2' 0-methyl rather than phosphodiesterase linkages within the oligodeoxyribonucleotide backbone.

VIII. Polypeptides of the Present Invention

The present invention makes available isolated polypeptides which are isolated from, or otherwise substantially free of other cellular proteins, especially other signal transduction factors and/or transcription factors which may normally be associated with the polypeptide. Subject polypeptides of the present invention include polypeptides encoded by the nucleic acids of SEQ ID Nos. 1, 3, 5, or 7, or a sequence complementary thereto. Preferred polypeptides are those having the amino acid sequence of SEQ ID Nos. 2, 4, 6, or 8. Polypeptides of the present invention include those proteins which are differentially regulated in tumor cells, especially colon cancer-derived cell lines (relative to normal cells, e.g., normal colon tissue and non-colon tissue). In preferred embodiments, the polypeptides are upregulated in tumor cells, especially colon cancer cancer-derived cell lines. In other embodiments, the polypeptides are downregulated in tumor cells, especially colon cancer-derived cell lines. Proteins which are upregulated, such as oncogenes, or downregulated, such as tumor suppressors, in aberrantly proliferating cells may be targets for diagnostic or therapeutic techniques. For example, upregulation of the cdc2 gene induces mitosis. Overexpression of the myt1 gene, a mitotic deactivator, negatively regulates the activity of cdc2. Aberrant proliferation may thus be induced either by upregulating cdc2 or by downregulating myt1.

The term "substantially free of other cellular proteins" (also referred to herein as "contaminating proteins") or "substantially pure or purified preparations" are defined as encompassing preparations of polypeptides having less than about 20% (by dry weight) contaminating protein, and preferably having less than about 5% contaminating protein. Functional forms of the subject polypeptides can be prepared, for the first time, as purified preparations by using a cloned nucleic acid as described herein. Full length proteins or fragments corresponding to one or more particular motifs and/or domains or to arbitrary sizes, for example, at least about 5, 10, 25, 50, 75, or 100 amino acids in length are within the scope of the present invention.

Preferred polypeptides are those that are encoded by nucleic acid sequences at least about 70%, 75%, 80%, 90%, 95%, 97%, or 98% identical to a mRNA sequence complementary to the nucleic acid sequence of SEQ ID Nos. 1, 3, 5, or 7, particularly preferred polypeptides are those of SEQ ID Nos. 2, 4, 6, or 8.

Isolated peptidyl portions of proteins can be obtained by screening peptides recombinantly produced from the corresponding fragment of the nucleic acid encoding such peptides. In addition, fragments can be chemically synthesized using techniques known in the art such as conventional Merrifield solid phase f-Moc or t-Boc chemistry. For example, a polypeptide of the present invention may be arbitrarily divided into fragments of desired length with no overlap of the fragments, or preferably divided into overlapping fragments of a desired length. The fragments can be produced (recombinantly or by chemical synthesis) and tested to identify those peptidyl fragments which can function as either agonists or antagonists of a wild-type (e.g., "authentic") protein.

Another aspect of the present invention concerns recombinant forms of the subject proteins. Recombinant polypeptides preferred by the present invention, in addition to native proteins, as described above are encoded by a nucleic acid, which is at least about 60%, more preferably at least about 80%, and more preferably about 85%, and more preferably about 90%, and more preferably about 95% identical to an amino acid sequence encoded by SEQ ID Nos. 1, 3, 5, or 7, or a sequence complementary thereto. Polypeptides which are encoded by a nucleic acid that is at least about 98–99% identical with the sequence of SEQ ID Nos. 1, 3, 5, or 7, or a sequence complementary thereto are also within the scope of the invention. Also included in the present invention are peptide fragments comprising at least a portion of such a protein.

In a preferred embodiment, a polypeptide of the present invention is a mammalian polypeptide and even more preferably a human polypeptide. In particularly preferred embodiment, the polypeptide retains wild-type bioactivity. It will be understood that certain post-translational modifications, e.g., phosphorylation and the like, can increase the apparent molecular weight of the polypeptide relative to the unmodified polypeptide chain. In a preferred embodiment, a polypeptide of the present invention has the sequence of SEQ ID Nos. 2, 4, 6, or 8.

The present invention further pertains to recombinant forms of one of the subject polypeptides. Such recombinant polypeptides preferably are capable of functioning in one of either role of antagonist or antagonist of at least one biological activity of a wild-type ("authentic") polypeptide of the appended sequence listing. The term "evolutionarily related to", with respect to amino acid sequences of proteins, refers to both polypeptides having amino acid sequences which have arisen naturally, and also to mutational variants of human polypeptides which are derived, for example, by combinatorial mutagenesis.

In general, polypeptides referred to herein as having an activity (e.g., are "bioactive") of a protein are defined as polypeptides which include an amino acid sequence of SEQ ID Nos. 2, 4, 6, or 8, and which mimic or antagonize all or a portion of the biological/biochemical activities of a naturally occurring protein. According to the present invention, a polypeptide has biological activity if it is a specific agonist or antagonist of a naturally occurring form of a protein.

Assays for determining whether a compound, e.g, a protein or variant thereof, has one or more of the above biological activities are well known in the art. In certain embodiments, the polypeptides of the present invention have activities such as those outlined above.

In another embodiment, the coding sequences for the polypeptide can be incorporated as a part of a fusion gene including a nucleotide sequence encoding a different polypeptide. This type of expression system can be useful under conditions where it is desirable to produce an immunogenic fragment of a polypeptide (see, for example, EP Publication No: 0259149; and Evans et al. (1989) Nature 339:385; Huang et at. (1988) J. Virol. 62:3 855; and Schlienger et al., (1992) J. Virol. 66:2). In addition to utilizing fusion proteins to enhance immunogenicity, it is widely appreciated that fusion proteins can also facilitate the expression of proteins, and, accordingly, can be used in the expression of the polypeptides of the present invention (see, for example, Current Protocols in Molecular Biology, eds. Ausubel et at. (N.Y. John Wiley & Sons, 1991)). In another embodiment, a fusion gene coding for a purification leader sequence, such as a poly-(His)/enterokinase cleavage site sequence at the N-terminus of the desired portion of the recombinant protein, can allow purification of the expressed fusion protein by affinity chromatography using a $Ni^{2+}$ metal resin. The purification leader sequence can then be subsequently removed by treatment with enterokinase to provide the purified protein (e.g., see Hochuli et al. (1987) J. Chromatography 411:177; and Janknecht et al. PNAS 88:8972).

Techniques for making fusion genes are known to those skilled in the art. Essentially, the joining of various DNA fragments coding for different polypeptide sequences is performed in accordance with conventional techniques, employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of nucleic acid fragments can be carried out using anchor primers which give rise to complementary overhangs between two consecutive nucleic acid fragments which can subsequently be annealed to generate a chimeric nucleic acid sequence (see, for example, Current Protocols in Molecular Biology, eds. Ausubel et al. John Wiley & Sons: 1992).

The present invention further pertains to methods of producing the subject polypeptides. For example, a host cell transfected with a nucleic acid vector directing expression of a nucleotide sequence encoding the subject polypeptides can be cultured under appropriate conditions to allow expression of the peptide to occur. Suitable media for cell culture are well known in the art. The recombinant polypeptide can be isolated from cell culture medium, host cells, or both using techniques known in the art for purifying proteins including ion-exchange chromatography, gel filtration chromatography, ultrafiltration, electrophoresis, and immunoaffinity purification with antibodies specific for such peptide. In a preferred embodiment, the recombinant polypeptide is a fusion protein containing a domain which facilitates its purification, such as GST fusion protein.

Moreover, it will be generally appreciated that, under certain circumstances, it may be advantageous to provide homologs of one of the subject polypeptides which function in a limited capacity as one of either an agonist (mimetic) or an antagonist, in order to promote or inhibit only a subset of the biological activities of the naturally occurring form of the protein. Thus, specific biological effects can be elicited by treatment with a homolog of limited function, and with fewer side effects relative to treatment with agonists or antagonists which are directed to all of the biological activities of naturally occurring forms of subject proteins.

Homologs of each of the subject polypeptide can be generated by mutagenesis, such as by discrete point mutation(s), or by truncation. For instance, mutation can give rise to homologs which retain substantially the same, or merely a subset, of the biological activity of the polypeptide from which it was derived. Alternatively, antagonistic forms of the polypeptide can be generated which are able to inhibit the function of the naturally occurring form of the protein, such as by competitively binding to a receptor.

The recombinant polypeptides of the present invention also include homologs of the wild-type proteins, such as versions of those proteins which are resistant to proteolytic cleavage, for example, due to mutations which alter ubiquitination or other enzymatic targeting associated with the protein.

Polypeptides may also be chemically modified to create derivatives by forming covalent or aggregate conjugates with other chemical moieties, such as glycosyl groups, lipids, phosphate, acetyl groups and the like. Covalent derivatives of proteins can be prepared by linking the chemical moieties to functional groups on amino acid sidechains of the protein or at the N-terminus or at the C-terminus of the polypeptide.

Modification of the structure of the subject polypeptides can be for such purposes as enhancing therapeutic or prophylactic efficacy, stability (e.g., ex vivo shelf life and resistance to proteolytic degradation), or post-translational modifications (e.g., to alter phosphorylation pattern of protein). Such modified peptides, when designed to retain at least one activity of the naturally occurring form of the protein, or to produce specific antagonists thereof, are considered functional equivalents of the polypeptides described in more detail herein. Such modified peptides can be produced, for instance, by amino acid substitution, deletion, or addition. The substitutional variant may be a substituted conserved amino acid or a substituted non-conserved amino acid.

For example, it is reasonable to expect that an isolated replacement of a leucine with an isoleucine or valine, an aspartate with a glutamate, a threonine with a serine, or a similar replacement of an amino acid with a structurally related amino acid (i.e., isosteric and/or isoelectric mutations) will not have a major effect on the biological activity of the resulting molecule. Conservative replacements are those that take place within a family of amino acids that are related in their side chains. Genetically encoded amino acids can be divided into four families: (1) acidic=aspartate, glutamate; (2) basic=lysine, arginine, histidine; (3) nonpolar=alanine, valine, leucine, isoleucine, proline, phenylalanine, methionine, tryptophan; and (4) uncharged polar=glycine, asparagine, glutamine, cysteine, serine, threonine, tyrosine. In similar fashion, the amino acid repertoire can be grouped as (1) acidic=aspartate, glutamate; (2) basic=lysine, arginine histidine, (3) aliphatic=glycine, alanine, valine, leucine, isoleucine, serine, threonine, with serine and threonine optionally be grouped separately as aliphatic-hydroxyl; (4) aromatic=phenylalanine, tyrosine, tiyptophan; (5) amide=asparagine, glutamine; and (6) sulfur-containing=cysteine and methionine. (see, for example, *Biochemistry*, 2 ed., Ed. by L. Stryer, W H Freeman and Co.: 1981). Whether a change in the amino acid sequence of a peptide results in a functional homolog (e.g., functional in the sense that the resulting polypeptide mimics or antagonizes the wild-type form) can be readily determined by assessing the ability of the variant peptide to produce a response in cells in a fashion similar to the wild-type protein, or competitively inhibit such a response.

Polypeptides in which more than one replacement has taken place can readily be tested in the same manner. The variant may be designed so as to retain biological activity of a particular region of the protein. In a non-limiting example, Osawa et al., 1994, *Biochemistry and Molecular International* 34:1003–1009, discusses the actin binding region of a protein from several different species. The actin binding regions of the these species are considered homologous based on the fact that they have amino acids that fall within "homologous residue groups." Homologous residues are judged according to the following groups (using single letter amino acid designations): STAG; ILVMF; HRK; DEQN; and FYW. For example, an S, a T, an A or a G can be in a position and the function (in this case actin binding) is retained.

Additional guidance on amino acid substitution is available from studies of protein evolution. Go et al., 1980, *Int. J. Peptide Protein Res.* 15: 211–224, classified amino acid residue sites as interior or exterior depending on their accessibility. More frequent substitution on exterior sites was confirmed to be general in eight sets of homologous protein families regardless of their biological functions and the presence or absence of a prosthetic group. Virtually all types of amino acid residues had higher mutabilities on the exterior than in the interior. No correlation between mutability and polarity was observed of amino acid residues in the interior and exterior, respectively. Amino acid residues were classified into one of three groups depending on their polarity: polar (Arg, Lys, His, Gln, Asn, Asp, and Glu); weak polar (Ala, Pro, Gly, Thr, and Ser), and nonpolar (Cys, Val, Met, Ile, Leu, Phe, Tyr, and Trp). Amino acid replacements during protein evolution were very conservative: 88% or 76% of them in the interior or exterior, respectively, were within the same group of the three. Intergroup replacements are such that weak polar residues are replaced more often by nonpolar residues in the interior and more often by polar residues on the exterior.

Querol et al., 1996, *Prot. Eng.* 9:265–271, provides general rules for amino acid substitutions to enhance protein thermostability. New glycosylation sites can be introduced as discussed in Olsen and Thomsen, 1991, *J. Gen. Microbiol.* 137 :579–585. An additional disulfide bridge can be introduced, as discussed by Perry and Wetzel, 1984, *Science* 226:555–557; Pantoliano et al., 1987, *Biochemistry* 26:2077–2082; Matsumura et al., 1989, *Nature* 342:291–293; Nishikawa et al., 1990, *Protein Eng.* 3:443–448; Takagi et al., 1990, *J. Biol. Chem,* 265:6874–6878; Clarke et al., 1993, *Biochemistry* 32:4322–43299; and Wakarchuk et al., 1994, *Protein Eng.* 7:1379–1386.

An additional metal binding site can be introduced, according to Toma et al., 1991, *Biochemistry* 30:97–106, and Haezerbrouck et al., 1993, *Protein Eng.* 6:643–649. Substitutions with prolines in loops can be made according to Masul et al., 1994, *Appl Env. Microbiol.* 60:3579–3584; and Hardy et al., *FEBS Lett.* 317:89–92.

Cysteine-depleted muteins are considered variants within the scope of the invention. These variants can be constructed according to methods disclosed in U.S. Pat. No. 4,959,314, which discloses how to substitute other amino acids for cysteines, and how to determine biological activity and effect of the substitution. Such methods are suitable for proteins according to this invention that have cysteine residues suitable for such substitutions, for example to eliminate disulfide bond formation.

To learn the identity and function of the gene that correlates with an nucleic acid, the nucleic acids or corresponding amino acid sequences can be screened against profiles of protein families. Such profiles focus on common structural motifs among proteins of each family. Publicly available profiles are described above. Additional or alternative profiles are described below.

In comparing a new nucleic acid with known sequences, several alignment tools are available. Examples include PileUp, which creates a multiple sequence alignment, and is described in Feng et al., *J. Mol. Evol.* (1987) 25: 351–360. Another method, GAP, uses the alignment method of Needleman et al., *J. Mol. Biol.* (1970) 48:443–453. GAP is best suited for global alignment of sequences. A third method, BestFit, functions by inserting gaps to maximize the number of matches using the local homology algorithm of Smith and Waterman, *Adv. Appl. Math.* (1981) 2:482–489.

Examples of such profiles are described below.

Chemokines

Chemokines are a family of proteins that have been implicated in lymphocyte trafficking, inflammatory diseases, angiogenesis, hematopoiesis, and viral infection. See, for example, Rollins, *Blood* (1997) 90(3):909–928, and Wells et al., *J. Leuk. Biol.* (1997) 61:545–550. U.S. Pat. No. 5,605,817 discloses DNA encoding a chemokine expressed in fetal spleen. U.S. Pat. No. 5,656,724 discloses chemokine-like proteins and methods of use. U.S. Pat. No. 5,602,008 discloses DNA encoding a chemokine expressed by liver.

Mutants of the encoded chemokines are polypeptides having an amino acid sequence that possesses at least one amino acid substitution, addition, or deletion as compared to native chemokines. Fragments possess the same amino acid sequence of the native chemokines; mutants may lack the amino and/or carboxyl terminal sequences. Fusions are mutants, fragments, or the native chemokines that also include amino and/or carboxyl terminal amino acid extensions.

The number or type of the amino acid changes is not critical, nor is the length or number of the amino acid deletions, or amino acid extensions that are incorporated in the chemokines as compared to the native chemokine amino acid sequences. A polynucleotide encoding one of these variant polypeptides will retain at least about 80% amino acid identity with at least one known chemokine. Preferably, these polypeptides will retain at least about 85% amino acid sequence identity, more preferably, at least about 90%; even more preferably, at least about 95%. In addition, the variants will exhibit at least 80%; preferably about 90%; more preferably about 95% of at least one activity exhibited by a native chemokine. Chemokine activity includes immunological, biological, receptor binding, and signal transduction functions of the native chemokine.

Chemotaxis. Assays for chemotaxis relating to neutrophils are described in Walz et al., *Biochem. Biophys. Res. Commun.* (1987) 149:755, Yoshimura et al., *Proc. Natl. Acad. Sci.* (USA) (1987) 84:9233, and Schroder et al., *J.*

*Immunol.* (1987) 139:3474; to lymphocytes, Larsen et al., *Science* (1989) 243:1464, Carr et al., *Proc. Natl. Acad. Sci.* (USA) (1994) 91:3652; to tumor-infiltrating lymphocytes, Liao et al., *J. Exp. Med.* (1995). 182:1301; to hemopoietic progenitors, Aiuti et al., *J. Exp. Med.* (1997) 185:111; to monocytes, Valente et al., *Biochem.* (1988) 27:4162; and to natural killer cells, Loetscher et al., *J. Immunol.* (1996) 156:322, and Allavena et al., *Eur. J. Immunol.* (1994) 24:3233.

Assays for determining the biological activity of attracting eosinophils are described in Dahinden et al, *J. Exp. Med.* (1994) 179:751, Weber et al., *J Immunol.* (1995) 154:4166, and Noso et al., *Biochem. Biophys. Res. Commun.* (1994) 200:1470; for attracting dendritic cells, Sozzani et al., *J. Immunol.* (1995) 155:3292; for attracting basophils, in Dahinden et al., *J. Exp. Med.* (1994) 179:751, Alam et al., *J. Immunol.* (1994) 152:1298, Alam et al., *J. Exp. Med.* (1992) 176:781; and for activating neutrophils, Maghazaci et al., *Eur. J. Immunol.* (1996) 26:315, and Taub et al, *J. Immunol.* (1995) 155:3877. Native chemokines can act as mitogens for fibroblasts, assayed as described in Mullenbach et al., *J. Biol. Chem.* (1986) 261:719.

Receptor Binding. Native chemokines exhibit binding activity with a number of receptors. Description of such receptors and assays to detect binding are described in, for example, Murphy et al., *Science* (1991) 253:1280; Combadiere et al., *J. Biol. Chem.* (1995) 270:29671; Daugherty et al., *J. Exp. Med.* (1996) 183:2349; Samson et al., *Biochem.* (1996) 35:3362; Raport et al., *J. Biol. Chem.* (1996) 271:17161; Combadiere et al., *J. Leukoc. Biol.* (1996) 60:147; Baba et al., *J. Biol. Chem.* (1997) 23: 14893; Yosida et al., *J. Biol. Chem.* (1997) 272:13803; Arvannitakis et al., Nature (1997) 385:347, and many other assays are known in the art.

Kinase Activiation. Assays for kinase activation are described by Yen et al., *J. Leukoc. Biol.* (1997) 61:529; Dubois et al., *J. Immunol.* (1996) 156:1356; Turner et al., *J. Immunol.* (1995) 155:2437. Assays for inhibition of angiogenesis or cell proliferation are described in Malone et al., *Science* (1990) 247:77. Glycosaminoglycan production can be induced by native chemokines, assayed as described in Castor et al., *Proc. Natl. Acad. Sci.* (USA) (1983) 80:765. Chemokinemediated histamine release from basophils is assayed as described in Dahinden et al., *J. Exp. Med.* (1989) 170:1787; and White et al., *Immunol. Lett.* (1989) 22:151. Heparin binding is described in Luster et al., *J. Exp. Med.* (1995) 182:219.

Dimenzation Activity. Chemokines can possess dimerization activity, which can be assayed according to Burrows et al., *Biochem* (1994) 33 12741, and Zhang et al., *Mol. Cell. Biol.* (1995) 15:4851. Native chemokines can play a role in the inflammatory response of viruses. This activity can be assayed as described in Bleul et al., *Nature* (1996) 382:829; and Oberlin et al., *Nature* (1996) 382:833. Exocytosis of monocytes can be promoted by native chemokines. The assay for such activity is described in Uguccioni et al., *Eur. J. Immunol.* (1995) 25:64. Native chemokines also can inhibit hemapoietic stem cell proliferation. The method for testing for such activity is reported in Graham et al., *Nature* (1990) 344:442.

Death Domain Proteins. Several protein families contain death domain motifs (Feinstein and Kimchi, *TIBS Letters* (1995) 20:242–244). Some death domain-containing proteins are implicated in cytotoxic intracellular signaling (Cleveland and Ihle, Cell (1995) 81:479–482, Pan et al., *Science* (1997) 276:111–113, Duan and Dixit, Nature (1997) 385:86–89, and Chinnaiyan et al., Science (1996) 274: 990–992). U.S. Pat. No. 5,563,039 describes a protein homologous to TRADD (Tumor Necrosis Factor Receptor-1 Associated Death Domain containing protein), and modifications of the active domain of TRADD that retain the functional characteristics of the protein, as well as apoptosis assays for testing the function of such death domain containing proteins. U.S. Pat. No. 5,658,883 discloses biologically active TGF-B1 peptides. U.S. Pat. No. 5,674,734 discloses protein RIP which contains a C-terminal death domain and an N-terminal kinase domain.

Leukemia Inhibitory Factor (LIF). An LIF profile is constructed from sequences of leukemia inhibitor factor, CT-I (cardiotrophin-1), CNTF (ciliary neurotrophic factor), OSM (oncostatin M), and IL-6 (interleukin-6). This profile encompasses a family of secreted cytokines that have pleiotropic effects on many cell types including hepatocytes, osteoclasts, neuronal cells and cardiac myocytes, and can be used to detect additional genes encoding such proteins. These molecules are all structurally related and share a common co-receptor gp130 which mediates intracellular signal transduction by cytoplasmic tyrosine kinases such as src.

Novel proteins related to this family are also likely to be secreted, to activate gp130 and to function in the development of a variety of cell types. Thus new members of this family would be candidates to be developed as growth or survival factors for the cell types that they stimulate. For more details on this family of cytokines, see Pennica et al., *Cytokine and Growth Factor Reviews* (1996) 7:81–91. U.S. Pat. No. 5,420,247 discloses LIF receptor and fusion proteins. U.S. Pat. No. 5,443,825 discloses human LIP.

Angiopoietin. Angiopoietin-1 is a secreted ligand of the TIE-2 tyrosine kinase; it functions as an angiogenic factor critical for normal vascular development. Angiopoietin-2 is a natural antagonist of angiopoietin-1 and thus functions as an antiangiogenic factor. These two proteins are structurally similar and activate the same receptor. (Folkman and D'Amore, *Cell* (1996) 87:1153–1155, and Davis et al., *Cell* (1996) 87:1161–1169.)

The angiopoietin molecules are composed of two domains, a coiled-coil region and a region related to fibrinogen. The fibrinogen domain is found in many molecules including ficolin and tesascin, and is well defined structurally with many members.

Receptor Protein-Tyrosine Kinases. Receptor Protein-Tyrosine Kinases or RPTKs are described in Lindberg. *Annu. Rev. Cell Biol.* (1994) 10:251–337.

Growth Factors: Epidermal Growth Factor (EGF) and Fibroblast Growth Factor (FGF). For a discussion of growth factor superfamilies, see *Growth Factors: A Practical Approach*. Appendix A1 (Ed. McKay and Leigh, Oxford University Press, NY, 1993) pp. 237–243.

The alignments (pretty box) for EGF and FGF are shown in FIGS. 1 and 2, respectively. U.S. Pat. No. 4,444,760 discloses acidic brain fibroblast growth factor, which is active in the promotion of cell division and wound healing. U.S. Pat. No. 5,439,818 discloses DNA encoding human recombinant basic fibroblast growth factor, which is active in wound healing. U.S. Pat. No. 5,604,293 discloses recombinant human basic fibroblast growth factor, which is useful for wound healing. U.S. Pat. No. 5,410,832 discloses brain-derived and recombinant acidic fibroblast growth factor, which act as mitogens for mesoderm and neuroectoderm-derived cells in culture, and promote wound healing in soft tissue, cartilaginous tissue and musculoskeletal tissue. U.S. Pat. No. 5,387,673 discloses biologically active fragments of FGF that retain activity.

Proteins of the TNF Family. A profile derived from the TNF family is created by aligning sequences of the following TNF family members: nerve growth factor (NGF), lymphotoxin, Fas ligand, tumor necrosis factor (TNF), CD40 ligand, TRAIL, ox40 ligand, 4-IBB ligand, CD27 ligand, and CD30 ligand. The profile is designed to identify sequences of proteins that constitute new members or homologues of this family of proteins.

U.S. Pat. No. 5,606,023 discloses mutant TNF proteins; U.S. Pat. No. 5,597,899 and U.S. Pat. No. 5,486,463 disclose TNF muteins; and U.S. Pat. No. 5,652,353 discloses DNA encoding TNF-a muteins.

Members of the TNF family of proteins have been show in vitro to multimerize, as described in Burrows et al., *Biochem.* (1994) 33:12741 and Zhang et al., *Mol. Cell. Biol.* (1995) 154851 and bind receptors as described in Browning et al., *J. Immunol.* (1994) 147:1230, Androlewicz et al., *J. Biol. Chem.* (1992) 267:2542, and Crowe et al., *Science* (1994) 264:707.

In vivo, TNFs proteolytically cleave a target protein as described in Kriegel et al., *Cell* (1988) 53:45 and Mohler et al., *Nature* (1994) 370:218 and demonstrate cell proliferation and differentiation activity. T-cell or thymocyte proliferation is assayed as described in Armitage et al., *Eur. J. Immunol.* (1992) 22:447; Current Protocols in Immunology, ed. J. E. Coligan et al., 3.1–3.19; Takai et al., *J. Immunol.* (1986) 137:3494–3500, Bertagnoli et al., *J. Immunol.* (1990) 145:1706–1712, Bertagnoli et al., *J. Immunol.* (1991) 133: 327–340, Bertagnoli et al., *J. Immunol.* (1992) 149:3778–3783, and Bowman et al., *J. Immunol.* (1994) 152:1756–1761. B cell proliferation and Ig secretion are assayed as described in Maliszewski, *J. Immunol.* (1990) 144:3028–3033, and Assays for B Cell Function: In vitro antibody production, Mond and Brunswick, Current Protocols in Immunol., Coligan Ed vol 1 pp 3.8.1–3.8.16, John Wiley and Sons, Toronto 1994, Kebrl et al., Science (1987) 238:1144 and Boussiotis et al., PNAS USA (1994) 91:7007.

Other in vivo activities include upregulation of cell surface antigens, upregulation of costimulatory molecules, and cellular aggregation/adhesion as described in Barrett et al., *J. Immunol.* (1991) 146:1722; Bjorck et al., *Eur. J. Immunol.* (1993) 23:1771; Clark et al., *Annu Rev. Immunol.* (1991) 9:97; Ranheim et al., *J. Exp. Med.* (1994) 177:925; Yellin, *J. Immunol.* (1994) 153:666; and Gruss et al., Blood (1994) 84:2305.

Proliferation and differentiation of hematopoietic and lymphopoictic cells has also been shown in vivo for TNFs, using assays for embryonic differentiation and hematopoiesis as described in Johansson et al., *Cellular Biology* (1995) 15:141–151, Keller et al., *Mol. Cell. Biol.* (1993) 13:473–486, McClanahan et al., Blood (1993) 81:2903–2915 and using assays to detect stem cell survival and differentiation as described in Culture of Hematopoietic Cells, Freshney et al. eds, pp 1–21, 23–29, 139–162, 163–179, and 265–268, Wiley-Liss, Inc., New York, N.Y., 1994, and Hirajama et al., *PNAS USA* (1992) 89:5907–5911.

In vivo activities of TNFs also include lymphocyte survival and apoptosis, assayed as described in Darzynkewicz et al., *Cytometry* (1992) 13:795–808; Gorczca et al., *Leukemia* (1993) 7:659–670; Itoh et al., *Cell* (1991) 66:233–243; Zacharduk, *J. Immunol.* (1990) 145:4037–4045; Zamai et al., *Cytometry* (1993) 14:891–897; and Gorczyca et al., *Int'l Oncol.* (1992) 1:639–648.

Some members of the TNF family are cleaved from the cell surface; others remain membrane bound. The three-dimensional structure of TNF is discussed in Sprang and Eck, Tumor Necrosis Factors; supra.

TNF proteins include a transmembrane domain. The protein is cleaved into a shorter soluble version, as described in Kriegler et al., Cell (1988) 53:45–53, Perez et al., *Cell* (1990) 63:251–258, and Shaw et al., Cell (1986) 46:659–667. The transmembrane domain is between amino acid 46 or 77 and the cytoplasmic domain is between position 1 and 45 on the human form of TNFα. The 3-dimensional motifs of TNF include a sandwich of two pleated b-sheets. Each sheet is composed of anti-parallel α-strands, α-Strands facing each other on opposite sites of the sandwich are connected by short polypeptide loops, as described in Van Ostade et al., Protein Engineering (1994) 7(1):5–22, and Sprang et al., Tumor Necrosis Factors; supra.

Residues of the TNF family proteins that are involved in the b-sheet secondary structure have been identified as described in Van Ostade et al., *Protein Engineering* (1994) 7(1):5–22, and Sprang et al., Tumor Necrosis Factors; supra.

TNF receptors are disclosed in U.S. Pat. No. 5,395,760. A profile derived from the TNF receptor family is created by aligning sequences of the TNF receptor family, including Apol/Fas, TNFR I and II, death receptor[3] (DR3), CD4O, ox40, CD27, and CD30. Thus, the profile is designed to identify, from the nucleic acids of the invention, sequences of proteins that constitute new members or homologs of this family of proteins.

Tumor necrosis factor receptors exist in two forms in humans: p55 TNFR and p75 TNFR, both of which provide intracellular signals upon binding with a ligand. The extracellular domains of these receptor proteins are cysteine rich. The receptors can remain membrane bound, although some forms of the receptors are cleaved forming soluble receptors. The regulation, diagnostic, prognostic, and therapeutic value of soluble TNF receptors is discussed in Aderka, *Cytokine and Growth Factor Reviews,* (1996) 7(3):231–240.

PDGF Family U.S. Pat. No. 5,326,695 discloses platelet derived growth factor agonists; bioactive portions of PDGF-B are used as agonists. U.S. Pat. No. 4,845,075 discloses biologically active B-chain homodimers, and also includes variants and derivatives of the PDGF-B chain. U.S. Pat. No. 5,128,321 discloses PDGF analogs and methods of use. Proteins having the same bioactivity as PDGF are disclosed, including A and B chain proteins.

Kinase (Including MKK) Family U.S. Pat. No. 5,650,501 discloses serine/threonine kinase, associated with mitotic and meiotic cell division; the protein has a kinase domain in its N-terminal and 3 PEST regions in the C-terminus. U.S. Pat. No. 5,605,825 discloses human PAK65, a serine protein kinase.

The foregoing discussion provides a few examples of the protein profiles that can be compared with the nucleic acids of the invention. One skilled in the art can use these and other protein profiles to identify the genes that correlate with the nucleic acids.

IX. Determining the Function of the Encoded Expression Products

Ribozymes, antisense constructs, dominant negative mutants, and triplex formation can be used to determine function of the expression product of an nucleic acid-related gene.

A. Ribozymes

Trans-cleaving catalytic RNAs (ribozymes) are RNA molecules possessing endoribonuclease activity. Ribozymes are specifically designed for a particular target, and the target message must contain a specific nucleotide sequence. They are engineered to cleave any RNA species site-specifically in the background of cellular RNA. The cleavage event renders the mRNA unstable and prevents protein expression. Importantly, ribozymes can be used to inhibit expression of a gene of unknown function for the purpose of determining its function in an in vitro or in vivo context, by detecting the phenotypic effect.

One commonly used ribozyme motif is the hammerhead, for which the substrate sequence requirements are minimal. Design of the hammerhead ribozyme is disclosed in Usman et al., *Current Opin. Struct. Biol.* (1996) 6:527–533. Usman also discusses the therapeutic uses of ribozymes. Ribozymes can also be prepared and used as described in Long et al., *FASEB J.* (1993) 7:25; Symons, *Ann. Rev. Biochem.* (1992) 61:641; Perrotta et al., *Biochem.* (1992) 31:16–17; Ojwang et al., Proc. Natl. Acad. Sci. (USA) (1992) 89:10802–10806; and U.S. Pat. No. 5,254,678. Ribozyme cleavage of HIV-I RNA is described in U.S. Pat. No. 5,144,019; methods of cleaving RNA using ribozymes is described in U.S. Pat. No. 5,116,742; and methods for increasing the specificity of ribozymes are described in U.S. Pat. No. 5,225,337 and Koizumi et al., Nucleic Acid Res. (1989) 17:7059–7071. Preparation and use of ribozyme fragments in a hammerhead structure are also described by Koizumi et al., *Nucleic Acids Res.* (1989) 17:7059–7071. Preparation and use of ribozyme fragments in a hairpin structure are described by Chowrira and Burke, *Nucleic Acids Res.* (1992) 20:2835. Ribozymes can also be made by rolling transcription as described in Daubendiek and Kool, *Nat. Biotechnol.* (1997) 15(3):273–277.

The hybridizing region of the ribozyme may be modified or may be prepared as a branched structure as described in Horn and Urdea, *Nucleic Acids Res.* (1989) 17:6959–67. The basic structure of the ribozymes may also be chemically altered in ways familiar to those skilled in the art, and chemically synthesized ribozymes can be administered as synthetic oligonucleotide derivatives modified by monomeric units. In a therapeutic context, liposome mediated delivery of ribozymes improves cellular uptake, as described in Birikh et al., *Eur. J. Biochem.* (1997) 245:1–16.

Using the nucleic acid sequences of the invention and methods known in the art, ribozymes are designed to specifically bind and cut the corresponding mRNA species. Ribozymes thus provide a means to inhibit the expression of any of the proteins encoded by the disclosed nucleic acids or their full-length genes. The full-length gene need not be known in order to design and use specific inhibitory ribozymes. In the case of a nucleic acid or cDNA of unknown function, ribozymes corresponding to that nucleotide sequence can be tested in vitro for efficacy in cleaving the target transcript. Those ribozymes that effect cleavage in vitro are further tested in vivo. The ribozyme can also be used to generate an animal model for a disease, as described in Birikh et al., *Eur. J. Biochem.* (1997) 245:1–16. An effective ribozyme is used to determine the function of the gene of interest by blocking its transcription and detecting a change in the cell. Where the gene is found to be a mediator in a disease, an effective ribozyme is designed and delivered in a gene therapy for blocking transcription and expression of the gene.

Therapeutic and functional genomic applications of ribozymes proceed beginning with knowledge of a portion of the coding sequence of the gene to be inhibited. Thus, for many genes, a partial nucleic acid sequence provides adequate sequence for constructing an effective ribozyme. A target cleavage site is selected in the target sequence, and a ribozyme is constructed based on the 5' and 3' nucleotide sequences that flank the cleavage site. Retro viral vectors are engineered to express monomeric and multimeric hammerhead ribozymes targeting the mRNA of the target coding sequence. These monomeric and multimeric ribozymes are tested in vitro for an ability to cleave the target mRNA. A cell line is stably transduced with the retroviral vectors expressing the ribozymes, and the transduction is confirmed by Northern blot analysis and reverse-transcription polymerase chain reaction (RT-PCR). The cells are screened for inactivation of the target mRNA by such indicators as reduction of expression of disease markers or reduction of the gene product of the target mRNA.

B. Antisense

Antisense nucleic acids are designed to specifically bind to RNA, resulting in the formation of RNA-DNA or RNA-RNA hybrids, with an arrest of DNA replication, reverse transcription or messenger RNA translation. Antisense polynucleotides based on a selected nucleic acid sequence can interfere with expression of the corresponding gene. Antisense polynucleotides are typically generated within the cell by expression from antisense constructs that contain the antisense nucleic acid strand as the transcribed strand. Antisense nucleic acids will bind and/or interfere with the translation of nucleic acid-related mRNA. The expression products of control cells and cells treated with the antisense construct are compared to detect the protein product of the gene corresponding to the nucleic acid. The protein is isolated and identified using routine Biochemical methods.

One rationale for using antisense methods to determine the function of the gene corresponding to a nucleic acid is the biological activity of antisense therapeutics. Antisense therapy for a variety of cancers is in clinical phase and has been discussed extensively in the literature. Reed reviewed antisense therapy directed at the Bcl-2 gene in tumors; gene transfer-mediated overexpression of Bcl-2 in tumor cell lines conferred resistance to many types of cancer drugs. (Reed, J. C., *N.C.I.* (1997) 89:988–990). The potential for clinical development of antisense inhibitors of ras is discussed by Cowsert, L. M., *Anti-Cancer Drug Design* (1997) 12:359–371. Additional important antisense targets include leukemia (Geurtz, A. M., *Anti-Cancer Drug Design* (1997) 12:341–358); human C-ref kinase (Monia, B. P., *Anti-Cancer Drug Design* (1997) 12:327–339); and protein kinase C (McGraw et al., *Anti-Cancer Drug Design* (1997) 12:315–326.

Given the extensive background literature and clinical experience in anti sense therapy, one skilled in the art can use selected nucleic acids of the invention as additional potential therapeutics. The choice of nucleic acid can be narrowed by first testing them for binding to "hot spot" regions of the genome of cancerous cells. If a nucleic acid is identified as binding to a "hot spot", testing the nucleic acid as an antisense compound in the corresponding cancer cells clearly is warranted.

Ogunbiyi et al., *Gastroenterology* (1997) 113(3):761–766 describe prognostic use of audio loss in colon cancer; Barks et al., *Genes, Chromosomes, and Cancer* (1997) 19(4):278–285 describe increased chromosome copy number detected by FISH in malignant melanoma; Nishjzake et al., *Genes. Chromosomes, and Cancer* (1997) 19(4):267–272 describe genetic alterations in primary breast cancer and their metastases and direct comparison using modified comparative genome hybridization; and Elo et al., *Cancer Research* (1997) 57(16):3356–3359 disclose that loss of heterozygosity at 16z24.1-q24.2 is significantly associated with metastatic and aggressive behavior of prostate cancer.

C. Dominant Negative Mutations

As an alternative method for identifying function of the nucleic acid-related gene, dominant negative mutations are readily generated for corresponding proteins that are active as homomultimers. A mutant polypeptide will interact with wild-type polypeptides (made from the other allele) and form a non-functional multimer. Thus, a mutation is in a substrate-binding domain, a catalytic domain, or a cellular localization domain. Preferably, the mutant polypeptide will be overproduced. Point mutations are made that have such an effect. In addition, fusion of different polypeptides of various lengths to the terminus of a protein can yield dominant negative mutants. General strategies are available for making dominant negative mutants. See Herskowitz, Nature (1987) 329:219–222. Such a technique can be used for creating a loss-of-function mutation, which is useful for determining the function of a protein.

D. Triplex Formation

Endogenous gene expression can also be reduced by inactivating or "knocking out" the gene or its promoter using targeted homologous recombination. (E.g., see Smithies et al., 1985, Nature 317:230–234; Thomas & Capecchi, 1987, Cell 51:503–512; Thompson et al., 1989 Cell 5:313–321; each of which is incorporated by reference herein in its entirety). For example, a mutant, non-functional gene (or a completely unrelated DNA sequence) flanked by DNA homologous to the endogenous gene (either the coding regions or regulatory regions of the gene) can be used, with or without a selectable marker and/or a negative selectable marker, to transfect cells that express that gene in vivo. Insertion of the DNA construct, via targeted homologous recombination, results in inactivation of the gene.

Alternatively, endogenous gene expression can be reduced by targeting deoxyribonucleotide sequences complementary to the regulatory region of the target gene (i.e., the gene promoter and/or enhancers) to form triple helical structures that prevent transcription of the gene in target cells in the body. (See generally, Helene, C. 1991, Anticancer Drug Des., 6(6):569–84; Helene, C., et al., 1992, Ann, N.Y. Accad. Sci., 660:27–36; and Maher, L. J., 1992, Bioassays 14(12):807–15).

Nucleic acid molecules to be used in triple helix formation for the inhibition of transcription are preferably single stranded and composed of deoxyribonucleotides. The base composition of these oligonucleotides should promote triple helix formation via Hoogsteen base-pairing rules, which generally require sizable stretches of either purines or pyrimidines to be present on one strand of a duplex. Nucleotide sequences may be pyrimidine-based, which will result in TAT and CGC triplets across the three associated strands of the resulting triple helix. The pyrimidine-rich molecules provide base complementarity to a purine-rich region of a single strand of the duplex in a parallel orientation to that strand. In addition, nucleic acid molecules may be chosen that are purine-rich, for example, containing a stretch of G residues. These molecules will form a triple helix with a DNA duplex that is rich in GC pairs, in which the majority of the purine residues are located on a single strand of the targeted duplex, resulting in CGC triplets across the three strands in the triplex.

Alternatively, the potential sequences that can be targeted for triple helix formation may be increased by creating a so called "switchback" nucleic acid molecule. Switchback molecules are synthesized in an alternating 5'-3', 3'-5' manner, such that they base pair with first one strand of a duplex and then the other, eliminating the necessity for a sizable stretch of either purines or pyrimidines to be present on one strand of a duplex.

Antisense RNA and DNA, ribozyme, and triple helix molecules of the invention may be prepared by any method known in the art for the synthesis of DNA and RNA molecules. These include techniques for chemically synthesizing oligodeoxyribonucleotides and oligoribonucleotides well known in the art such as for example solid phase phosphoramidite chemical synthesis. Alternatively, RNA molecules may be generated by in vitro and in vivo transcription of DNA sequences encoding the antisense RNA molecule. Such DNA sequences may be incorporated into a wide variety of vectors which incorporate suitable RNA polymerase promoters such as the T7 or SP6 polymerase promoters. Alternatively, antisense cDNA constructs that synthesize antisense RNA constitutively or inducibly, depending on the promoter used, can be introduced stably into cell lines.

Moreover, various well known modifications to nucleic acid molecules may be introduced as a means of increasing intracellular stability and half-life. Possible modifications include but are not limited to the addition of flanking sequences of ribonucleotides or deoxyribonucleotides to the 5' and/or 3' ends of the molecule or the use of phosphorothioate or 2' 0-methyl rather than phosphodiesterase linkages within the oligodeoxyribonucleotide backbone.

X. Diagnostic & Prognostic Assays and Drug Screening Methods

The present invention provides method for determining whether a subject is at risk for developing a disease or condition characterized by unwanted cell proliferation by detecting the disclosed biomarkers, i.e., the disclosed nucleic acid markers (SEQ ID Nos: 1, 3, 5, or 7, or a sequence complementary thereto, or a sequence which hybridizes to one or more of SEQ ID Nos 1, 3, 5, or 7) and/or polypeptide markers for the disease or condition encoded thereby.

In clinical applications, human tissue samples can be screened for the presence and/or absence of the biomarkers identified herein. Such samples may comprise tissue samples, whole cells, cell lysates, or isolated nucleic acids, including, for example, needle biopsy cores, surgical resection samples, lymph node tissue, or serum. For example, these methods include obtaining a biopsy, which is optionally fractionated by cryostat sectioning to enrich tumor cells to about 80% of the total cell population. In certain embodiments, nucleic acids extracted from these samples may be amplified using techniques well known in the art. The levels of selected markers detected would be compared with statistically valid groups of metastatic, non-metastatic malignant, benign, or normal colon tissue samples.

In one embodiment, the diagnostic method comprises determining whether a subject has an abnormal mRNA and/or protein level of the disclosed markers, such as by Northern blot analysis, reverse transcription-polymerase chain reaction (RT-PCR), in situ hybridization, immunoprecipitation, Western blot hybridization, or immunohistochemistry. According to the method, cells are obtained from a subject and the levels of the disclosed biomarkers, protein or mRNA level, is determined and compared to the level of these markers in a healthy subject. An abnormal level of the biomarker polypeptide or mRNA levels is likely to be indicative of cancer such as colon cancer.

Accordingly, in one aspect, the invention provides probes and primers that are specific to the unique nucleic acid markers disclosed herein. Accordingly, the nucleic acid probes comprise a region of a nucleic acid sequence of SEQ ID Nos 1, 3, 5, or 7 sufficient to hybridize with a nucleic acid substantialy complementary to the sequence of SEQ ID Nos 1, 3, 5, or 7. Preferred nucleic acid molecules for use as probes/primers can further comprise a region of nucleic acid sequence substantially complementary to the sequence of SEQ ID Nos. 1, 3, 5, or 7 sufficient to hybridize with the sequence of SEQ ID Nos. 1, 3, 5, or 7. In addition, nucleic acid sequences useful as probes/primers comprise a nucleotide sequence at least about 8 nucleotides in length, at least about 12 nucleotides in length, preferably at least about 15 nucleotides, more preferably about 25 nucleotides, and most preferably at least 40 nucleotides, and up to all or nearly all of the coding sequence which is complementary to a portion of the coding sequence of a marker nucleic acid sequence, which nucleic acid sequence is represented by SEQ ID Nos: 1, 3, 5, or 7, or a sequence complementary thereto.

In one embodiment, the method comprises using a nucleic acid probe to determine the presence of cancerous cells in a tissue from a patient. Specifically, the method comprises:

1. providing a nucleic acid probe comprising a nucleotide sequence at at least about 8 nucleotides in length, at least about 12 nucleotides in length, preferably at least about 15 nucleotides, more preferably about 25 nucleotides, and most preferably at least about 40 nucleotides, and up to all or nearly all of the coding sequence which is complementary to a portion of the coding sequence of a nucleic acid sequence represented by SEQ ID Nos: 1, 3, 5, or 7, or a sequence complementary thereto, and is differentially expressed in tumors cells, such as colon cancer cells;
2. obtaining a tissue sample from a patient potentially comprising cancerous cells;
3. providing a second tissue sample containing cells substantially all of which are non-cancerous;
4. contacting the nucleic acid probe under stringent conditions with RNA of each of said first and second tissue samples (e.g., in a Northern blot or in situ hybridization assay); and
5. comparing (a) the amount of hybridization of the probe with RNA of the first tissue sample, with (b) the amount of hybridization of the probe with RNA of the second tissue sample; wherein a statistically significant difference in the amount of hybridization with the RNA of the first tissue sample as compared to the amount of hybridization with the RNA of the second tissue sample is indicative of the presence of cancerous cells in the first tissue sample.

In one aspect, the method comprises in situ hybridization with a probe derived from a given marker nucleic acid sequence, which nucleic acid sequence is represented by SEQ ID Nos: 1, 3, 5, or 7, or a sequence complementary thereto. The method comprises contacting the labeled hybridization probe with a sample of a given type of tissue potentially containing cancerous or pre-cancerous cells as well as normal cells, and determining whether the probe labels some cells of the given tissue type to a degree significantly different (e.g., by at least 0.5 fold, at least 2 fold, at least 5 fold, at least 20 fold, or at least 50 fold) than the degree to which it labels other cells of the same tissue type.

Also within the invention is a method of determining the phenotype of a test cell from a given human tissue, e.g., whether the cell is (a) normal, or (b) cancerous or precancerous, by contacting the mRNA of a test cell with a nucleic acid probe at least approximately 8 nucleotides in length, preferably about 12, preferably about 15, preferably about 25, more preferably about 40 nucleotides in length, and up to all or nearly all of a sequence which is complementary to a portion of the coding sequence of a nucleic acid sequence represented by SEQ ID Nos: 1, 3, 5, or 7, or a sequence complementary thereto, and which is differentially expressed in tumor cells as compared to normal cells of the given tissue type; and determining the approximate amount of hybridization of the probe to the mRNA, an amount of hybridization either more or less than that seen with the mRNA of a normal cell of that tissue type being indicative that the test cell is cancerous or pre-cancerous.

Alternatively, the above diagnostic assays may be carried out using antibodies to detect the protein product encoded by the marker nucleic acid sequence, which nucleic acid sequence is represented by SEQ ID Nos: 1, 3, 5, or 7, or a sequence complementary thereto. Preferably, the protein product has the sequence of one or more of SEQ ID Nos. 2, 4, 6, or 8. Accordingly, in one embodiment, the assay would include contacting the proteins of the test cell with an antibody specific for the gene product of a nucleic acid represented by SEQ II) Nos: 1, 3, 5, or 7, or a sequence complementary thereto, the marker nucleic acid being one which is expressed at a given control level in normal cells of the same tissue type as the test cell, and determining the approximate amount of immunocomplex formation by the antibody and the proteins of the test cell, wherein a statistically significant difference in the amount of the immunocomplex formed with the proteins of a test cell as compared to a normal cell of the same tissue type is an indication that the test cell is cancerous or pre-cancerous.

Another such method includes the steps of: providing an antibody specific for the gene product of a marker nucleic acid sequence represented by SEQ ID Nos 1, 3, 5, or 7, or a sequence complementary thereto, the gene product being present in cancerous tissue of a given tissue type (e.g., colon tissue) at a level more or less than the level of the gene product in non-cancerous tissue of the same tissue type; obtaining from a patient a first sample of tissue of the given tissue type, which sample potentially includes cancerous cells; providing a second sample of tissue of the same tissue type (which may be from the same patient or from a normal control, e.g. another individual or cultured cells), this second sample containing normal cells and essentially no cancerous cells; contacting the antibody with protein (which may be partially purified, in lysed but unfractionated cells, or in situ) of the first and second samples under conditions permitting immunocomplex formation between the antibody and the marker nucleic acid sequence product present in the samples; and comparing (a) the amount of immunocomplex formation in the first sample, with (b) the amount of immunocomplex formation in the second sample, wherein a statistically significant difference in the amount of immunocomplex formation in the first sample less as compared to the amount of immunocomplex formation in the second sample is indicative of the presence of cancerous cells in the first sample of tissue.

The subject invention further provides a method of determining whether a cell sample obtained from a subject possesses an abnormal amount of marker polypeptide which comprises (a) obtaining a cell sample from the subject, (b) quantitatively determining the amount of the marker polypeptide in the sample so obtained, and (c) comparing the amount of the marker polypeptide so determined with a known standard, so as to thereby determine whether the cell sample obtained from the subject possesses an abnormal amount of the marker polypeptide. Such marker polypeptides may be detected by immunohistochemical assays, dot-blot assays, ELISA and the like.

Immunoassays are commonly used to quantitate the levels of proteins in cell samples, and many other immunoassay techniques are known in the art. The invention is not limited to a particular assay procedure, and therefore is intended to include both homogeneous and heterogeneous procedures. Exemplary immunoassays which can be conducted according to the invention include fluorescence polarization immunoassay (FPIA), fluorescence immunoassay (FIA), enzyme immunoassay (EIA), nephelometric inhibition immunoassay (NIA), enzyme linked immunosorbent assay (ELISA), and radioimmunoassay (RIA). An indicator moiety, or label group, can be attached to the subject antibodies and is selected so as to meet the needs of various uses of the method which are often dictated by the availability of assay equipment and compatible immunoassay procedures. General techniques to be used in performing the various immunoassays noted above are known to those of ordinary skill in the art.

In another embodiment, the level of the encoded product, i.e., the product encoded by SEQ ID Nos 1, 3, 5, or 7, or a sequence complementary thereto, in a biological fluid (e.g., blood or urine) of a patient may be determined as a way of monitoring the level of expression of the marker nucleic acid sequence in cells of that patient. Such a method would include the steps of obtaining a sample of a biological fluid from the patient, contacting the sample (or proteins from the sample) with an antibody specific for a encoded marker polypeptide, and determining the amount of immune complex formation by the antibody, with the amount of immune complex formation being indicative of the level of the marker encoded product in the sample. This determination is particularly instructive when compared to the amount of immune complex formation by the same antibody in a control sample taken from a normal individual or in one or more samples previously or subsequently obtained from the same person.

In another embodiment, the method can be used to determine the amount of marker polypeptide present in a cell, which in turn can be correlated with progression of a hyperproliferative disorder, e.g., colon cancer. The level of the marker polypeptide can be used predictively to evaluate whether a sample of cells contains cells which are, or are predisposed towards becoming, transformed cells. Moreover, the subject method can be used to assess the phenotype of cells which are known to be transformed, the phenotyping results being useful in planning a particular therapeutic regimen. For instance, very high levels of the marker polypeptide in sample cells is a powerful diagnostic and prognostic marker for a cancer, such as colon cancer. The observation of marker polypeptide level can be utilized in decisions regarding, e.g., the use of more aggressive therapies.

As set out above, one aspect of the present invention relates to diagnostic assays for determining, in the context of cells isolated from a patient, if the level of a marker polypeptide is significantly reduced in the sample cells. The term "significantly reduced" refers to a cell phenotype wherein the cell possesses a reduced cellular amount of the marker polypeptide relative to a normal cell of similar tissue origin. For example, a cell may have less than about 50%, 25%, 10%, or 5% of the marker polypeptide that a normal control cell. In particular, the assay evaluates the level of marker polypeptide in the test cells, and, preferably, compares the measured level with marker polypeptide detected in at least one control cell, e.g., a normal cell and/or a transformed cell of known phenotype.

Of particular importance to the subject invention is the ability to quantitate the level of marker polypeptide as determined by the number of cells associated with a normal or abnormal marker polypeptide level. The number of cells with a particular marker polypeptide phenotype may then be correlated with patient prognosis. In one embodiment of the invention, the marker polypeptide phenotype of the lesion is determined as a percentage of cells in a biopsy which are found to have abnormally high/low levels of the marker polypeptide. Such expression may be detected by immunohistochemical assays, dot-blot assays, ELISA and the like.

Where tissue samples are employed, immunohistochemical staining may be used to determine the number of cells having the marker polypeptide phenotype. For such staining, a multiblock of tissue is taken from the biopsy or other tissue sample and subjected to proteolytic hydrolysis, employing such agents as protease K or pepsin. In certain embodiments, it may be desirable to isolate a nuclear fraction from the sample cells and detect the level of the marker polypeptide in the nuclear fraction.

The tissue samples are fixed by treatment with a reagent such as formalin, glutaraldehyde, methanol, or the like. The samples are then incubated with an antibody, preferably a monoclonal antibody, with binding specificity for the marker polypeptides. This antibody may be conjugated to a label for subsequent detection of binding. Samples are incubated for a time sufficient for formation of the immunocomplexes. Binding of the antibody is then detected by virtue of a label conjugated to this antibody. Where the antibody is unlabeled, a second labeled antibody may be employed, e.g., which is specific for the isotype of the anti-marker polypeptide antibody. Examples of labels which may be employed include radionuclides, fluorescers, chemiluniinescers, enzymes and the like.

Where enzymes are employed, the substrate for the enzyme may be added to the samples to provide a colored or fluorescent product. Examples of suitable enzymes for use in conjugates include horseradish peroxidase, alkaline phosphatase, malate dehydrogenase and the like. Where not commercially available, such antibody-enzyme conjugates are readily produced by techniques known to those skilled in the art.

In one embodiment, the assay is performed as a dot blot assay. The dot blot assay finds particular application where tissue samples are employed as it allows determination of the average amount of the marker polypeptide associated with a single cell by correlating the amount of marker polypeptide in a cell-free extract produced from a predetermined number of cells.

It is well established in the cancer literature that tumor cells of the same type (e.g., breast and/or colon tumor cells) may not show uniformly increased expression of individual oncogenes or uniformly decreased expression of individual tumor suppressor genes. There may also be varying levels of expression of a given marker gene even between cells of a given type of cancer, further emphasizing the need for reliance on a battery of tests rather than a single test. Accordingly, in one aspect, the invention provides for a battery of tests utilizing a number of probes of the invention, in order to improve the reliability and/or accuracy of the diagnostic test.

In one embodiment, the present invention also provides a method wherein nucleic acid probes are immobilized on a DNA chip in an organized array. Oligonucleotides can be bound to a solid support by a variety of processes, including lithography. For example a chip can hold up to 250,000 oligonucleotides (GeneChip, Affymetrix). These nucleic acid probes comprise a nucleotide sequence at least about 8 nucleotides in length, preferably at least about 12 preferably at least about 15 nucleotides, more preferably at least about 25 nucleotides, and most preferably at least about 40 nucleotides, and up to all or nearly all of a sequence which is complementary to a portion of the coding sequence of a marker nucleic acid sequence represented by SEQ ID Nos: 1, 3, 5, or 7 and is differentially expressed in tumor cells, such as colon cancer cells. The present invention provides significant advantages over the available tests for various cancers, such as colon cancer, because it increases the reliability of the test by providing an array of nucleic acid markers on a single chip.

The method includes obtaining a biopsy, which is optionally fractionated by cryostat sectioning to enrich tumor cells to about 80% of the total cell population. The DNA or RNA is then extracted, amplified, and analyzed with a DNA chip to determine the presence of absence of the marker nucleic acid sequences.

In one embodiment, the nucleic acid probes are spotted onto a substrate in a two-dimensional matrix or array. Samples of nucleic acids can be labeled and then hybridized to the probes. Double-stranded nucleic acids, comprising the labeled sample nucleic acids bound to probe nucleic acids, can be detected once the unbound portion of the sample is washed away.

The probe nucleic acids can be spotted on substrates including glass, nitrocellulose, etc. The probes can be bound to the substrate by either covalent bonds or by non-specific interactions, such as hydrophobic interactions. The sample nucleic acids can be labeled using radioactive labels, fluorophores, chromophores, etc.

Techniques for constructing arrays and methods of using these arrays are described in EP No. 0 799 897; PCT No. WO 97/292 12; PCT No. WO 97127317; EP No. 0 785 280; PCT No. WO 97/02357; U.S. Pat. No. 5,593,839; U.S. Pat. No. 5,578,832; EP No. 0 728 520; U.S. Pat. No. 5,599,695; EP No. 0 721 016; U.S. Pat. No. 5,556,752; PCT No. WO 95/22058; and U.S. Pat. No. 5,631,734.

Further, arrays can be used to examine differential expression of genes and can be used to determine gene function. For example, arrays of the instant nucleic acid sequences can be used to determine if any of the nucleic acid sequences are differentially expressed between normal cells and cancer cells, for example. High expression of a particular message in a cancer cell, which is not observed in a corresponding normal cell, can indicate a cancer specific protein.

In yet another embodiment, the invention contemplates using a panel of antibodies which are generated against the marker polypeptides of this invention, which polypeptides are SEQ ID Nos: 2, 4, 6, or 8. Such a panel of antibodies may be used as a reliable diagnostic probe for colon cancer. The assay of the present invention comprises contacting a biopsy sample containing cells, e.g., colon cells, with a panel of antibodies to one or more of the encoded products to determine the presence or absence of the marker polypeptides.

The diagnostic methods of the subject invention may also be employed as follow-up to treatment, e.g., quantitation of the level of marker polypeptides may be indicative of the effectiveness of current or previously employed cancer therapies as well as the effect of these therapies upon patient prognosis.

Accordingly, the present invention makes available diagnostic assays and reagents for detecting gain and/or loss of marker polypeptides from a cell in order to aid in the diagnosis and phenotyping of proliferative disorders arising from, for example, tumorigenic transformation of cells.

The diagnostic assays described above can be adapted to be used as prognostic assays, as well. Such an application takes advantage of the sensitivity of the assays of the invention to events which take place at characteristic stages in the progression of a tumor. For example, a given marker gene may be up- or downregulated at a very early stage, perhaps before the cell is irreversibly committed to developing into a malignancy, while another marker gene may be characteristically up or down regulated only at a much later stage. Such a method could involve the steps of contacting the mRNA of a test cell with a nucleic acid probe derived from a given marker nucleic acid which is expressed at different characteristic levels in cancerous or precancerous cells at different stages of tumor progression, and determining the approximate amount of hybridization of the probe to the mRNA of the cell, such amount being an indication of the level of expression of the gene in the cell, and thus an indication of the stage of tumor progression of the cell; alternatively, the assay can be carried out with an antibody specific for the gene product of the given marker nucleic acid, contacted with the proteins of the test cell. A battery of such tests will disclose not only the existence and location of a tumor, but also will allow the clinician to select the mode of treatment most appropriate for the tumor, and to predict the likelihood of success of that treatment.

The methods of the invention can also be used to follow the clinical course of a tumor. For example, the assay of the invention can be applied to a tissue sample from a patient; following treatment of the patient for the cancer, another tissue sample is taken and the test repeated. Successful treatment will result in either removal of all cells which demonstrate differential expression characteristic of the cancerous or precancerous cells, or a substantial increase in expression of the gene in those cells, perhaps approaching or even surpassing normal levels.

In yet another embodiment, the invention provides methods for determining whether a subject is at risk for developing a disease, such as a predisposition to develop cancer, for example colon cancer, associated with an aberrant activity of any one of the polypeptides of SEQ ID Nos: 2, 4, 6, or 8, wherein the aberrant activity of the polypeptide is characterized by detecting the presence or absence of a genetic lesion characterized by at least one of (i) an alteration affecting the integrity of a gene encoding a marker polypeptides, or (ii) the misexpression of the encoding nucleic acid. To illustrate, such genetic lesions can be detected by ascertaining the existence of at least one of(i) a deletion of one or more nucleotides from the nucleic acid sequence, (ii) an addition of one or more nucleotides to the nucleic acid sequence, (iii) a substitution of one or more nucleotides of the nucleic acid sequence, (iv) a gross chromosomal rearrangement of the nucleic acid sequence, (v) a gross alteration in the level of a messenger RNA transcript of the nucleic acid sequence, (vii) aberrant modification of the nucleic acid sequence, such as of the methylation pattern of the genomic DNA, (vii) the presence of a non-wild type splicing pattern of a messenger RNA transcript of the gene, (viii) a non-wild type level of the marker polypeptide, (ix) allelic loss of the gene, and/or (x) inappropriate post-translational modification of the marker polypeptide.

The present invention provides assay techniques for detecting lesions in the encoding nucleic acid sequence. These methods include, but are not limited to, methods involving sequence analysis, Southern blot hybridization, restriction enzyme site mapping, and methods involving detection of absence of nucleotide pairing between the nucleic acid to be analyzed and a probe.

Specific diseases or disorders, e.g., genetic diseases or disorders, are associated with specific allelic variants of polymorphic regions of certain genes, which do not necessarily encode a mutated protein. Thus, the presence of a specific allelic variant of a polymorphic region of a gene in a subject can render the subject susceptible to developing a specific disease or disorder. Polymorphic regions in genes, can be identified, by determining the nucleotide sequence of genes in populations of individuals. If a polymorphic region is identified, then the link with a specific disease can be determined by studying specific populations of individuals, e.g, individuals which developed a specific disease, such as colon cancer. A polymorphic region can be located in any region of a gene, e.g., exons, in coding or non coding regions of exons, introns, and promoter region.

In an exemplary embodiment, there is provided a nucleic acid composition comprising a nucleic acid probe including a region of nucleotide sequence which is capable of hybridizing to a sense or antisense sequence of a gene or naturally occurring mutants thereof, or 5' or 3' flanking sequences or intronic sequences naturally associated with the subject genes or naturally occurring mutants thereof The nucleic acid of a cell is rendered accessible for hybridization, the probe is contacted with the nucleic acid of the sample, and the hybridization of the probe to the sample nucleic acid is detected. Such techniques can be used to detect lesions or allelic variants at either the genomic or mRNA level, including deletions, substitutions, etc., as well as to determine mRNA transcript levels.

A preferred detection method is allele specific hybridization using probes overlapping the mutation or polymorphic site and having about 5, 10, 20, 25, or 30 nucleotides around the mutation or polymorphic region. In a preferred embodiment of the invention, several probes capable of hybridizing specifically to allelic variants are attached to a solid phase support, e.g., a "chip". Mutation detection analysis using these chips comprising oligonucleotides, also termed "DNA probe arrays" is described e.g., in Cronin et al. (1996) Human Mutation 7:244. In one embodiment, a chip comprises all the allelic variants of at least one polymorphic region of a gene. The solid phase support is then contacted with a test nucleic acid and hybridization to the specific probes is detected. Accordingly, the identity of numerous allelic variants of one or more genes can be identified in a simple hybridization experiment.

In certain embodiments, detection of the lesion comprises utilizing the probe/primer in a polymerase chain reaction (PCR) (see, e.g. U.S. Pat. Nos. 4,683,195 and 4,683,202), such as anchor PCR or RACE PCR, or, alternatively, in a ligase chain reaction (LCR) (see, e.g., Landegran et al. (1988) Science 241:1077–1080; and Nakazawa et al. (1994) PNAS 91:360–364), the latter of which can be particularly useful for detecting point mutations in the gene (sec Abravaya et al. (1995) Nuc Acid Res 23:675–682). In a merely illustrative embodiment, the method includes the steps of (i) collecting a sample of cells from a patient, (ii) isolating nucleic acid (e.g., genomic, mRNA or both) from the cells of the sample, (iii) contacting the nucleic acid sample with one or more primers which specifically hybridize to a nucleic acid sequence under conditions such that hybridization and amplification of the nucleic acid (if present) occurs, and (iv) detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

Alternative amplification methods include: self sustained sequence replication (Guatelli, J. C. et al., 1990, Proc. Natl. Acad. Sci. USA 87:1874–1878), transcriptional amplification system (Kwoh, D. Y. et al., 1989, Proc. Natl. Acad. Sci. USA 86:1173–1177), Q-Beta Replicase (Lizardi, P. M. et al., 1988, Bio/Technology 6:1197), or any other nucleic acid amplification method, followed by the detection of the amplified molecules using techniques well known to those of skill in the art. These detection schemes are especially useful for the detection of nucleic acid molecules if such molecules are present in very low numbers.

In a preferred embodiment of the subject assay, mutations in, or allelic variants, of a gene from a sample cell are identified by alterations in restriction enzyme cleavage patterns. For example, sample and control DNA is isolated, amplified (optionally), digested with one or more restriction endonucleases, and fragment length sizes are determined by gel electrophoresis. Moreover, the use of sequence specific ribozymes (see, for example, U.S. Pat. No. 5,498,531) can be used to score for the presence of specific mutations by development or loss of a ribozyme cleavage site.

Another aspect of the invention is directed to the identification of agents capable of modulating the differentiation and proliferation of cells characterized by aberrant proliferation. In this regard, the invention provides assays for determining compounds that modulate the expression of the marker nucleic acids (SEQ ID Nos: 1, 3, 5, or 7, or a sequence complementary thereto) and/or alter for example, inhibit the bioactivity of the encoded polypeptide.

Several in vivo methods can be used to identify compounds that modulate expression of the marker nucleic acids (SEQ ID Nos: 1, 3, 5, or 7, or a sequence complementary thereto) and/or alter for example, inhibit the bioactivity of the encoded polypeptide.

Drug screening is performed by adding a test compound to a sample of cells, and monitoring the effect. A parallel sample which does not receive the test compound is also monitored as a control. The treated and untreated cells are then compared by any suitable phenotypic criteria, including but not limited to microscopic analysis, viability testing, ability to replicate, histological examination, the level of a particular RNA or polypeptide associated with the cells, the level of enzymatic activity expressed by the cells or cell lysates, and the ability of the cells to interact with other cells or compounds. Differences between treated and untreated cells indicates effects attributable to the test compound.

Desirable effects of a test compound include an effect on any phenotype that was conferred by the cancer-associated marker nucleic acid sequence. Examples include a test compound that limits the overabundance of mRNA, limits production of the encoded protein, or limits the functional effect of the protein. The effect of the test compound would be apparent when comparing results between treated and untreated cells.

The invention thus also encompasses methods of screening for agents which inhibit expression of the nucleic acid markers (SEQ ID Nos: 1, 3, 5, or 7, or a sequence complementary thereto) in vitro, comprising exposing a cell or tissue in which the marker nucleic acid mRNA is detectable in cultured cells to an agent in order to determine whether the agent is capable of inhibiting production of the mRNA; and determining the level of mRNA in the exposed cells or tissue, wherein a decrease in the level of the mRNA after exposure of the cell line to the agent is indicative of inhibition of the marker nucleic acid mRNA production.

Alternatively, the screening method may include in vitro screening of a cell or tissue in which marker protein is detectable in cultured cells to an agent suspected of inhibiting production of the marker protein; and determining the level of the marker protein in the cells or tissue, wherein a decrease in the level of marker protein after exposure of the cells or tissue to the agent is indicative of inhibition of marker protein production.

The invention also encompasses in vivo methods of screening for agents which inhibit expression of the marker nucleic acids, comprising exposing a mammal having tumor cells in which marker mRNA or protein is detectable to an agent suspected of inhibiting production of marker mRNA or protein; and determining the level of marker mRNA or protein in tumor cells of the exposed mammal. A decrease in the level of marker mRNA or protein after exposure of the mammal to the agent is indicative of inhibition of marker nucleic acid expression.

Accordingly, the invention provides a method comprising incubating a cell expressing the marker nucleic acids (SEQ ID Nos: 1, 3, 5, or 7, or a sequence complementary thereto) with a test compound and measuring the mRNA or protein level. The invention further provides a method for quantitatively determining the level of expression of the marker nucleic acids in a cell population, and a method for determining whether an agent is capable of increasing or decreasing the level of expression of the marker nucleic acids in a cell population. The method for determining whether an agent is capable of increasing or decreasing the level of expression of the marker nucleic acids in a cell population comprises the steps of (a) preparing cell extracts from control and agent-treated cell populations, (b) isolating the marker polypeptides from the cell extracts, (c) quantifying (e.g., in parallel) the amount of an immunocomplex formed between the marker polypeptide and an antibody specific to said polypeptide. The marker polypeptides of this invention may also be quantified by assaying for its bioactivity. Agents that induce increased the marker nucleic acid expression may be identified by their ability to increase the amount of immunocomplex formed in the treated cell as compared with the amount of the immunocomplex formed in the control cell. In a similar manner, agents that decrease expression of the marker nucleic acid may be identified by their ability to decrease the amount of the immunocomplex formed in the treated cell extract as compared to the control cell.

mRNA levels can be determined by Northern blot hybridization. mRNA levels can also be determined by methods involving PCR. Other sensitive methods for measuring mRNA, which can be used in high throughput assays, e.g., a method using a DELFIA endpoint detection and quantification method, are described, e.g., in Webb and Hurskainen (1996) *Journal of Biomolecular Screening* 1:119. Marker protein levels can be determined by immunoprecipitations or immunohistochemistiy using an antibody that specifically recognizes the protein product of SEQ ID Nos: 2, 4, 6, or 8.

Agents that are identified as active in the drug screening assay are candidates to be tested for their capacity to block cell proliferation activity. These agents would be useful for treating a disorder involving aberrant growth of cells, especially colon cells.

A variety of assay formats will suffice and, in light of the present disclosure, those not expressly described herein will nevertheless be comprehended by one of ordinary skill in the art. For instance, the assay can be generated in many different formats, and include assays based on cell-free systems, e.g., purified proteins or cell lysates, as well as cell-based assays which utilize intact cells.

In many drug screening programs which test libraries of compounds and natural extracts, high throughput assays are desirable in order to maximize the number of compounds surveyed in a given period of time. Assays of the present invention which are performed in cell-free systems, such as may be derived with purified or semi-purified proteins or with lysates, are often preferred as "primary" screens in that they can be generated to permit rapid development and relatively easy detection of an alteration in a molecular target which is mediated by a test compound. Moreover, the effects of cellular toxicity and/or bioavailability of the test compound can be generally ignored in the in vitro system, the assay instead being focused primarily on the effect of the drug on the molecular target as may be manifest in an alteration of binding affinity with other proteins or changes in enzymatic properties of the molecular target.

A. Use of Nucleic Acids as Probes in Mapping and in Tissue Profiling Probes

Polynucleotide probes as described above, e g, comprising at least 8 contiguous nucleotides selected from the nucleotide SEQ ID Nos. 1, 3, 5, or 7, or a sequence complementary thereto, are used for a variety of purposes, including identification of human chromosomes and determining transcription levels. Additional disclosure about preferred regions of the nucleic acid sequences is found in the accompanying tables.

The nucleotide probes are labeled, for example, with a radioactive, fluorescent, biotinylated, or chemiluminescent label, and detected by well known methods appropriate for the particular label selected. Protocols for hybridizing nucleotide probes to preparations of metaphase chromosomes are also well known in the art. A nucleotide probe will hybridize specifically to nucleotide sequences in the chromosome preparations which are complementary to the nucleotide sequence of the probe. A probe that hybridizes specifically to a nucleic acid should provide a detection signal at least 5-, 10-, or 20-fold higher than the background hybridization provided with other unrelated sequences.

In a non-limiting example, commercial programs are available for identifying regions of chromosomes commonly associated with disease, such as cancer. Nucleic acids of the invention can be used to probe these regions. For example, if, through profile searching, a nucleic acid is identified as corresponding to a gene encoding a kinase, its ability to bind to a cancer-related chromosomal region will suggest its role as a kinase in one or more stages of tumor cell development/growth. Although some experimentation would be required to elucidate the role, the nucleic acid constitutes a new material for isolating a specific protein that has potential for developing a cancer diagnostic or therapeutic.

Nucleotide probes are used to detect expression of a gene corresponding to the nucleic acid. For example, in Northern blots, mRNA is separated electrophoretically and contacted with a probe. A probe is detected as hybridizing to an mRNA species of a particular size. The amount of hybridization is quantitated to determine relative amounts of expression, for example under a particular condition. Probes are also used to detect products of amplification by polymerase chain reaction. The products of the reaction are hybridized to the probe and hybrids are detected. Probes are used for in situ hybridization to cells to detect expression. Probes can also be used in vivo for diagnostic detection of hybridizing sequences. Probes are typically labeled with a radioactive isotope. Other types of detectable labels may be used such as chromophores, fluorophores, and enzymes.

Expression of specific mRNA can vary in different cell types and can be tissue specific. This variation of mRNA levels in different cell types can be exploited with nucleic acid probe assays to determine tissue types. For example, PCR, branched DNA probe assays, or blotting techniques utilizing nucleic acid probes substantially identical or complementary to nucleic acids of SEQ ID Nos. 1, 3, 5, or 7, or a sequence complementary thereto, can determine the presence or absence of target cDNA or mRNA.

Examples of a nucleotide hybridization assay are described in Urdea et al., PCT WO92/02526 and Urdea et al., U.S. Pat. No. 5,124,246, both incorporated herein by reference. The references describe an example of a sandwich nucleotide hybridization assay.

Alternatively, the Polymerase Chain Reaction (PCR) is another means for detecting small amounts of target nucleic acids, as described in Mullis et al., *Met/i. Enzymol.* (1987) 155:335–350; U.S. Pat. No. 4,683,195; and U.S. Pat. No. 4,683,202, all incorporated herein by reference. Two primer polynucleotides nucleotides hybridize with the target nucleic acids and are used to prime the reaction. The primers may be composed of sequence within or 3' and 5 ' to the polynucleotides of the Sequence Listing. Alternatively, if the primers are 3' and 5' to these polynucleotides, they need not hybridize to them or the complements. A thermostable polymerase creates copies of target nucleic acids from the primers using the original target nucleic acids as a template. After a large amount of target nucleic acids is generated by the polymerase, it is detected by methods such as Southern blots. When using the Southern blot method, the labeled probe will hybridize to a polynucleotide of the Sequence Listing or complement.

Furthermore, mRNA or cDNA can be detected by traditional blotting techniques described in Sambrook et al., "Molecular Cloning: A Laboratory Manual" (New York, Cold Spring Harbor Laboratory, 1989). mRNA or cDNA generated from mRNA using a polymerase enzyme can be purified and separated using gel electrophoresis. The nucleic acids on the gel are then blotted onto a solid support, such as nitrocellulose. The solid support is exposed to a labeled probe and then washed to remove any unhybridized probe. Next, the duplexes containing the labeled probe are detected. Typically, the probe is labeled with radioactivity.

Mapping

Nucleic acids of the present invention are used to identify a chromosome on which the corresponding gene resides. For example, using in situ hybridization (ISH), or fluorescence in situ hybridization (FISH) on normal metaphase spreads, comparative genomic hybridization allows total genome assessment of changes in relative copy number of DNA sequences. See Schwartz and Samad, *Current Opinions in Biotechnology* (1994) 8:70–74; Kallioniemi et al., *Seminars in Cancer Biology* (1993) 4:41–46; Valdes and Tagle, *Methods in Molecular Biology* (1997) 68:1, Boultwood, ed., Human Press, Totowa, N.J.

Preparations of human metaphase chromosomes are prepared using standard cytogenetic techniques from human primary tissues or cell lines. Nucleotide probes comprising at least 12 contiguous nucleotides selected from the nucleotide sequence of SEQ ID Nos. 1, 3, 5, or 7, or a sequence complementary thereto, are used to identify the corresponding chromosome. The nucleotide probes are labeled, for example, with a radioactive, fluorescent, biotinylated, or chemiluminescent label, and detected by well known methods appropriate for the particular label selected. Protocols for hybridizing nucleotide probes to preparations of metaphase chromosomes are also well known in the art. A nucleotide probe will hybridize specifically to nucleotide sequences in the chromosome preparations that are complementary to the nucleotide sequence of the probe. A probe that hybridizes specifically to a target gene provides a detection signal at least 5-, 10-, or 20-fold higher than the background hybridization provided with unrelated coding sequences.

Nucleic acids are mapped to particular chromosomes using, for example, radiation hybrids or chromosome-specific hybrid panels. See Leach et al., Advances in Genetics, (1995) 33:63–99; Walter et al., Nature Genetics (1994) 7:22–28; Walter and Goodfellow, Trends in Genetics (1992) 9:352. Panels for radiation hybrid mapping are available from Research Genetics, Inc., Huntsville, Ala., USA. Databases for markers using various panels are available via the world wide web at http:/F/shgc-www.stanford.edu, and other locations. The statistical program RHMAP can be used to construct a map based on the data from radiation hybridization with a measure of the relative likelihood of one order versus another, RHIIVIAP is available via the world wide web at sph.umich.edu/group/statgen/software.

Such mapping can be useful in identifying the function of the target gene by its proximity to other genes with known function. Function can also be assigned to the target gene when particular syndromes or diseases map to the same chromosome.

Tissue Profiling

The nucleic acids of the present invention can be used to determine the tissue type from which a given sample is derived. For example, a metastatic lesion is identified by its developmental organ or tissue source by identifying the expression of a particular marker of that organ or tissue. If a nucleic acid is expressed only in a specific tissue type, and a metastatic lesion is found to express that nucleic acid, then the developmental source of the lesion has been identified. Expression of a particular nucleic acid is assayed by detection of either the corresponding mRNA or the protein product. Immunological methods, such as antibody staining, are used to detect a particular protein product. Hybridization methods may be used to detect particular mRNA species, including but not limited to in situ hybridization and Northern blotting.

Use of Polymorphisms

A nucleic acid will be useful in forensics, genetic analysis, mapping, and diagnostic applications if the corresponding region of a gene is polymorphic in the human population. A particular polymorphic form of the nucleic acid may be used to either identify a sample as deriving from a suspect or rule out the possibility that the sample derives from the suspect. Any means for detecting a polymorphism in a gene are used, including but not limited to electrophoresis of protein polymorphic variants, differential sensitivity to restriction enzyme cleavage, and hybridization to an allele-specific probe.

B. Use of Nucleic Acids and Encoded Polypeptides to Raise Antibodies

Expression products of a nucleic acid, the corresponding mRNA or cDNA, or the corresponding complete gene are prepared and used for raising antibodies for experimental, diagnostic, and therapeutic purposes. For nucleic acids to which a corresponding gene has not been assigned, this provides an additional method of identifying the corresponding gene. The nucleic acid or related cDNA is expressed as described above, and antibodies are prepared. These antibodies are specific to an epitope on the encoded polypeptide, and can precipitate or bind to the corresponding native protein in a cell or tissue preparation or in a cell-free extract of an in vitro expression system.

Immunogens for raising antibodies are prepared by mixing the polypeptides encoded by the nucleic acids of the present invention with adjuvants. Alternatively, polypeptides are made as fusion proteins to larger immunogenic proteins. Polypeptides are also covalently linked to other larger immunogenic proteins, such as keyhole limpet hemocyanin. Immunogens are typically administered intradermally, subcutaneously, or intramuscularly. Immunogens are administered to experimental animals such as rabbits, sheep, and mice, to generate antibodies. Optionally, the animal spleen cells are isolated and fused with myeloma cells to form hybridomas which secrete monoclonal antibodies. Such methods are well known in the art. According to another method known in the art, the nucleic acid is administered directly, such as by intramuscular injection, and expressed in vivo. The expressed protein generates a variety of protein-specific immune responses, including production of antibodies, comparable to administration of the protein.

Preparations of polyclonal and monoclonal antibodies specific for nucleic acid-encoded proteins and polypeptides are made using standard methods known in the art. The antibodies specifically bind to epitopes present in the polypeptides of SEQ ID Nos. 2, 4, 6, or 8. Typically, at least about 6, 8, 10, or 12 contiguous amino acids are required to form an epitope. However, epitopes which involve noncontiguous amino acids may require more, for example, at least about 15, 25, or 50 amino acids. A short sequence of a nucleic acid may then be unsuitable for use as an epitope to raise antibodies for identifying the corresponding novel protein, because of the potential for cross-reactivity with a known protein. However, the antibodies may be useful for other purposes, particularly if they identify common structural features of a known protein and a novel polypeptide encoded by a nucleic acid of the invention.

Antibodies that specifically bind to human nucleic acid-encoded polypeptides should provide a detection signal at least about 5-, 10-, or 20-fold higher than a detection signal provided with other proteins when used in Western blots or other immunochemical assays. Preferably, antibodies that specifically bind nucleic acid T-encoded polypeptides do not detect other proteins in immunochemical assays and can immunoprecipitate nucleic acid-encoded proteins from solution.

To test for the presence of serum antibodies to the nucleic acid-encoded polypeptide in a human population, human antibodies are purified by methods well known in the art. Preferably, the antibodies are affinity purified by passing antiserum over a column to which a nucleic acid-encoded protein, polypeptide, or fusion protein is bound. The bound antibodies can then be eluted from the column, for example using a buffer with a high salt concentration.

In addition to the antibodies discussed above, genetically engineered antibody derivatives are made, such as single chain antibodies.

Antibodies may be made by using standard protocols known in the art (See, for example, Antibodies: A Laboratory Manual ed. by Harlow and Lane (Cold Spring Harbor Press: 1988)). A mammal, such as a mouse, hamster, or rabbit can be immunized with an immunogenic form of the peptide (e.g., a mammalian polypeptide or an antigenic fragment which is capable of eliciting an antibody response, or a fusion protein as described above).

In one aspect, this invention includes monoclonal antibodies that show a subject polypeptide is highly expressed in colorectal tissue or tumor tissue, especially colon cancer tissue or colon cancer-derived cell lines. Therefore, in one embodiment, this invention provides a diagnostic tool for the analysis of expression of a subject polypeptide in general, and in particular, as a diagnostic for colon cancer.

Techniques for conferring immunogenicity on a protein or peptide include conjugation to carriers or other techniques well known in the art. An immunogenic portion of a protein can be administered in the presence of adjuvant. The progress of immunization can be monitored by detection of antibody titers in plasma or serum. Standard ELISA or other immunoassays can be used with the immunogen as antigen to assess the levels of antibodies. In a preferred embodiment, the subject antibodies are immunospecific for antigenic determinants of a protein of a mammal, e.g., antigenic determinants of a protein of SEQ ID Nos. 2, 4, 6, or 8 or closely related homologs (e.g., at least 90% identical, and more preferably at least 95% identical).

Following immunization of an animal with an antigenic preparation of a polypeptide, antisera can be obtained and, if desired, polyclonal antibodies isolated from the serum. To produce monoclonal antibodies, antibody-producing cells (lymphocytes) can be harvested from an immunized animal and fused by standard somatic cell fusion procedures with immortalizing cells such as myeloma cells to yield hybridoma cells. Such techniques are well known in the art, and include, for example, the hybridoma technique (originally developed by Kohler and Milstein, (1975) Nature, 256: 495–497), the human B cell hybridoma technique (Kozbar et al., (1983) Immunology Today, 4: 72), and the EBV-hybridoma technique to produce human monoclonal antibodies (Cole et al., (1985) Monoclonal Antibodies and Cancer Therapy, Alan R. Liss, Inc. pp. 77–96). Hybridoma cells can be screened immunochemically for production of antibodies specifically reactive with a polypeptide of the present invention and monoclonal antibodies isolated from a culture comprising such hybridoma cells.

The term antibody as used herein is intended to include fragments thereof which are also specifically reactive with one of the subject polypeptides. Antibodies can be fragmented using conventional techniques and the fragments screened for utility in the same manner as described above for whole antibodies. For example, $F(ab)_2$ fragments can be generated by treating antibody with pepsin. The resulting $F(ab)_2$ fragment can be treated to reduce disulfide bridges to produce Fab fragments. The antibody of the present invention is further intended to include bispecific, single-chain, and chimeric and humanized molecules having affinity for a polypeptide conferred by at least one CDR region of the antibody. In preferred embodiments, the antibodies, the antibody further comprises a label attached thereto and able to be detected, (e.g., the label can be a radioisotope, fluorescent compound, chemiluminescent compound, enzyme, or enzyme co-factor).

Antibodies can be used, e.g., to monitor protein levels in an individual for determining, e.g., whether a subject has a disease or condition, such as colon cancer, associated with an aberrant protein level, or allowing determination of the efficacy of a given treatment regimen for an individual afflicted with such a disorder. The level of polypeptides may be measured from cells in bodily fluid, such as in blood samples.

Another application of antibodies of the present invention is in the immunological screening of cDNA libraries constructed in expression vectors such as gtl1, gtl8–23, ZAP, and ORF8. Messenger libraries of this type, having coding sequences inserted in the correct reading frame and orientation, can produce fusion proteins. For instance, gt1 1 will produce fusion proteins whose amino termini consist of b-galactosidase amino acid sequences and whose carboxyl termini consist of a foreign polypeptide. Antigenic epitopes of a protein, e.g., other orthologs of a particular protein or other paralogs from the same species, can then be detected with antibodies, as, for example, reacting nitrocellulose filters lifted from infected plates with antibodies. Positive phage detected by this assay can then be isolated from the infected plate. Thus, the presence of homologs can be detected and cloned from other animals, as can alternate isoforms (including splicing variants) from humans.

In another embodiment, a panel of monoclonal antibodies may be used, wherein each of the epitope's involved functions are represented by a monoclonal antibody. Loss or perturbation of binding of a monoclonal antibody in the panel would be indicative of a mutational attention of the protein and thus of the corresponding gene.

C. Differential Expression

The present invention also provides a method to identify abnormal or diseased tissue in a human. For nucleic acids corresponding to profiles of protein families as described above, the choice of tissue may be dictated by the putative biological function. The expression of a gene corresponding to a specific nucleic acid is compared between a first tissue that is suspected of being diseased and a second, normal tissue of the human. The normal tissue is any tissue of the human, especially those that express the target gene including, but not limited to, brain, thymus, testis, heart, prostate, placenta, spleen, small intestine, skeletal muscle, pancreas, and the mucosal lining of the colon.

The tissue suspected of being abnormal or diseased can be derived from a different tissue type of the human, but preferably it is derived from the same tissue type; for example an intestinal polyp or other abnormal growth should be compared with normal intestinal tissue. A difference between the target gene, mRNA, or protein in the two tissues which are compared, for example in molecular weight, amino acid or nucleotide sequence, or relative abundance, indicates a change in the gene, or a gene which regulates it, in the tissue of the human that was suspected of being diseased.

The target genes in the two tissues are compared by any means known in the art. For example, the two genes are sequenced, and the sequence of the gene in the tissue suspected of being diseased is compared with the gene sequence in the normal tissue. The target genes, or portions thereof, in the two tissues are amplified, for example using nucleotide primers based on the nucleotide sequence shown in the Sequence Listing, using the polymerase chain reaction. The amplified genes or portions of genes are hybridized to nucleotide probes selected from a corresponding nucleotide sequence shown SEQ ID No. 1, 3, 5, or 7. A difference in the nucleotide sequence of the target gene in the tissue suspected of being diseased compared with the normal nucleotide sequence suggests a role of the nucleic acid-encoded proteins in the disease, and provides a lead for preparing a therapeutic agent.

The nucleotide probes are labeled by a variety of methods, such as radiolabeling, biotinylation, or labeling with fluorescent or chemiluminescent tags, and detected by standard methods known in the art.

Alternatively, target mRNA in the two tissues is compared. PolyA⁺RNA is isolated from the two tissues as is known in the art. For example, one of skill in the art can readily determine differences in the size or amount of target mRNA transcripts between the two tissues using Northern blots and nucleotide probes selected from the nucleotide sequence shown in the Sequence Listing. Increased or decreased expression of a target mRNA in a tissue sample suspected of being diseased, compared with the expression of the same target mRNA in a normal tissue, suggests that the expressed protein has a role in the disease, and also provides a lead for preparing a therapeutic agent.

Any method for analyzing proteins is used to compare two nucleic acid-encoded proteins from matched samples. The sizes of the proteins in the two tissues are compared, for example, using antibodies of the present invention to detect nucleic acid-encoded proteins in Western blots of protein extracts from the two tissues. Other changes, such as expression levels and subcellular localization, can also be detected immunologically, using antibodies to the corresponding protein. A higher or lower level of nucleic acid-encoded protein expression in a tissue suspected of being diseased, compared with the same nucleic acid-encoded protein expression level in a normal tissue, is indicative that the expressed protein has a role in the disease, and provides another lead for preparing a therapeutic agent.

Similarly, comparison of gene sequences or of gene expression products, e.g., mRNA and protein, between a human tissue that is suspected of being diseased and a normal tissue of a human, are used to follow disease progression or remission in the human. Such comparisons of genes, mRNA, or protein are made as described above.

For example, increased or decreased expression of the target gene in the tissue suspected of being neoplastic can indicate the presence of neoplastic cells in the tissue. The degree of increased expression of the target gene in the neoplastic tissue relative to expression of the gene in normal tissue, or differences in the amount of increased expression of the target gene in the neoplastic tissue over time, is used to assess the progression of the neoplasia in that tissue or to monitor the response of the neoplastic tissue to a therapeutic protocol over time.

The expression pattern of any two cell types can be compared, such as low and high metastatic tumor cell lines, or cells from tissue which have and have not been exposed to a therapeutic agent. A genetic predisposition to disease in a human is detected by comparing an target gene, mRNA, or protein in a fetal tissue with a normal target gene, mRNA, or protein. Fetal tissues that are used for this purpose include, but are not limited to, amniotic fluid, chorionic villi, blood, and the blastomere of an in vitro-fertilized embryo. The comparable normal target gene is obtained from any tissue. The mRNA or protein is obtained from a normal tissue of a human in which the target gene is expressed. Differences such as alterations in the nucleotide sequence or size of the fetal target gene or mRNA, or alterations in the molecular weight, amino acid sequence, or relative abundance of fetal target protein, can indicate a germline mutation in the target gene of the fetus, which indicates a genetic predisposition to disease.

D. Use of Nucleic Acids, and Encoded Polvpeptides to Screen for Peptide Analogs and Antagonists Polypeptides of SEQ ID Nos. 2, 4, 6, or 8 or polypeptides encoded by the instant nucleic acids, e.g., SEQ ID Nos. 1, 3, 5, or 7, or a sequence complementary thereto, and corresponding full length genes can be used to screen peptide libraries to identify binding partners, such as receptors, from among the encoded polypeptides.

A library of peptides may be synthesized following the methods disclosed in U.S. Pat. No. 5,010,175, and in PCT WO 91/17823. As described below in brief, one prepares a mixture of peptides, which is then screened to identify the peptides exhibiting the desired signal transduction and receptor binding activity. In the '175 method, a suitable peptide synthesis support (e.g., a resin) is coupled to a mixture of appropriately protected, activated amino acids. The concentration of each amino acid in the reaction mixture is balanced or adjusted in inverse proportion to its coupling reaction rate so that the product is an equimolar mixture of amino acids coupled to the starting resin. The bound amino acids are then deprotected, and reacted with another balanced amino acid mixture to form an equimolar mixture of all possible dipeptides. This process is repeated until a mixture of peptides of the desired length (e.g., hexamers) is formed. Note that one need not include all amino acids in each step: one may include only one or two amino acids in some steps (e.g., where it is known that a particular amino acid is essential in a given position), thus reducing the complexity of the mixture. After the synthesis of the peptide library is completed, the mixture of peptides is screened for binding to the selected polypeptide. The peptides are then tested for their ability to inhibit or enhance activity. Peptides exhibiting the desired activity are then isolated and sequenced.

The method described in WO 91/17823 is similar. However, instead of reacting the synthesis resin with a mixture of activated amino acids, the resin is divided into twenty equal portions (or into a number of portions corresponding to the number of different amino acids to be added in that step), and each amino acid is coupled individually to its portion of resin. The resin portions are then combined, mixed, and again divided into a number of equal portions for reaction with the second amino acid. In this manner, each reaction may be easily driven to completion. Additionally, one may maintain separate "subpools" by treating portions in parallel, rather than combining all resins at each step. This simplifies the process of determining which peptides are responsible for any observed receptor binding or signal transduction activity.

In such cases, the subpools containing, e.g., 1–2,000 candidates each are exposed to one or more polypeptides of the invention. Each subpool that produces a positive result is then resynthesized as a group of smaller subpools (sub-subpools) containing, e.g., 20–100 candidates, and reassayed. Positive sub-subpools may be resynthesized as individual compounds, and assayed finally to determine the peptides that exhibit a high binding constant. These peptides can be tested for their ability to inhibit or enhance the native activity. The methods described in WO 91/7823 and U.S. Pat. No. 5,194,392 (herein incorporated by reference) enable the preparation of such pools and subpools by automated techniques in parallel, such that all synthesis and resynthesis may be performed in a matter of days.

Peptide agonists or antagonists are screened using any available method, such as signal transduction, antibody binding, receptor binding, mitogenic assays, chemotaxis assays, etc. The methods described herein are presently preferred. The assay conditions ideally should resemble the conditions under which the native activity is exhibited in vivo, that is, under physiologic pH, temperature, and ionic strength. Suitable agonists or antagonists will exhibit strong inhibition or enhancement of the native activity at concentrations that do not cause toxic side effects in the subject. Agonists or antagonists that compete for binding to the native polypeptide may require concentrations equal to or greater than the native concentration, while inhibitors capable of binding irreversibly to the polypeptide may be added in concentrations on the order of the native concentration.

The end results of such screening and experimentation will be at least one novel polypeptide binding partner, such as a receptor, encoded by a nucleic acid of the invention, and at least one peptide agonist or antagonist of the novel binding partner. Such agonists and antagonists can be used to modulate, enhance, or inhibit receptor function in cells to which the receptor is native, or in cells that possess the receptor as a result of genetic engineering. Further, if the novel receptor shares biologically important characteristics with a known receptor, information about agonist/antagonist binding may help in developing improved agonists/antagonists of the known receptor.

E. Pharmaceutical Compositions and Therapeutic Uses

Pharmaceutical compositions can comprise polypeptides, antibodies, or polynucleotides of the claimed invention. The pharmaceutical compositions will comprise a therapeutically effective amount of either polypeptides, antibodies, or polynucleotides of the claimed invention.

The term "therapeutically effective amount" as used herein refers to an amount of a therapeutic agent to treat, ameliorate, or prevent a desired disease or condition, or to exhibit a detectable therapeutic or preventative effect. The effect can be detected by, for example, chemical markers or antigen levels. Therapeutic effects also include reduction in physical symptoms, such as decreased body temperature. The precise effective amount for a subject will depend upon the subject's size and health, the nature and extent of the condition, and the therapeutics or combination of therapeutics selected for administration. Thus, it is not useful to specify an exact effective amount in advance. However, the effective amount for a given situation can be determined by routine experimentation and is within the judgment of the clinician.

For purposes of the present invention, an effective dose will be from about 0.01 mg/kg to 50 mg/kg or 0.05 mg/kg to about 10 mg/kg of the DNA constructs in the individual to which it is administered.

A pharmaceutical composition can also contain a pharmaceutically acceptable carrier. The term "pharmaceutically acceptable carrier" refers to a carrier for administration of a therapeutic agent, such as antibodies or a polypeptide, genes, and other therapeutic agents. The term refers to any pharmaceutical carrier that does not itself induce the production of antibodies harmful to the individual receiving the composition, and which may be administered without undue toxicity. Suitable carriers may be large, slowly metabolized macromolecules such as proteins, polysaccharides, polylactic acids, polyglycolic acids, polymeric amino acids, amino acid copolymers, and inactive virus particles. Such carriers are well known to those of ordinary skill in the art.

Pharmaceutically acceptable salts can be used therein, for example, mineral acid salts such as hydrochlorides, hydrobromides, phosphates, sulfates, and the like; and the salts of organic acids such as acetates, propionates, malonates, benzoates, and the like. A thorough discussion of pharmaceutically acceptable excipients is available in *Remington's Pharmaceutical Sciences* (Mack Pub. Co., N.J. 1991).

Pharmaceutically acceptable carriers in therapeutic compositions may contain liquids such as water, saline, glycerol and ethanol. Additionally, auxiliary substances, such as wetting or emulsifying agents, pH buffering substances, and the like, may be present in such vehicles. Typically, the therapeutic compositions are prepared as injectables, either as liquid solutions or suspensions; solid forms suitable for solution in, or suspension in, liquid vehicles prior to injection may also be prepared. Liposomes are included within the definition of a pharmaceutically acceptable carrier.

Delivery Methods

Once formulated, the nucleic acid compositions of the invention can be (I) administered directly to the subject; (2) delivered ex vivo, to cells derived from the subject or (3) delivered in vitro for expression of recombinant proteins.

Direct delivery of the compositions will generally be accomplished by injection, either subcutaneously, intraperitoneally, intravenously or intramuscularly, or delivered to the interstitial space of a tissue. The compositions can also be administered into a tumor or lesion. Other modes of administration include oral and pulmonary administration, suppositories, and transdermal applications, needles, and gene guns or hyposprays. Dosage treatment may be a single dose schedule or a multiple dose schedule.

Methods for the ex vivo delivery and reimplantation of transformed cells into a subject are known in the art and described in e.g., International Publication No. WO 93/14778. Examples of cells useful in ex vivo applications include, for example, stem cells, particularly hematopoetic, lymph cells, macrophages, dendritic cells, or tumor cells.

Generally, delivery of nucleic acids for both ex vivo and in vitro applications can be accomplished by, for example, dextran-mediated transfection, calcium phosphate precipitation, polybrene mediated transfection, protoplast fusion, electroporation, encapsulation of the polynucleotide(s) in liposomes, and direct microinjection of the DNA into nuclei, all well known in the art.

Once a subject gene has been found to correlate with a proliferative disorder, such as neoplasia, dysplasia, and hyperplasia, the disorder may be amenable to treatment by administration of a therapeutic agent based on the nucleic acid or corresponding polypeptide.

Preparation of antisense polypeptides is discussed above. Neoplasias that are treated with the antisense composition include, but are not limited to, cervical cancers, melanomas, colorectal adenocarcinomas, Wilms' tumor, retinoblastoma, sarcomas, myosarcomas, lung carcinomas, leukemias, such as chronic myelogenous leukemia, promyelocytic leukemia, monocytic leukemia, and myeloid leukemia, and lymphomas, such as histiocytic lymphoma. Proliferative disorders that are treated with the therapeutic composition include disorders such as anhydric hereditary ectodermal dysplasia, congenital alveolar dysplasia, epithelial dysplasia of the cervix, fibrous dysplasia of bone, and mammary dysplasia. Hyperplasias, for example, endometrial, adrenal, breast, prostate, or thyroid hyperplasias or pseudoepitheliomatous hyperplasia of the skin, are treated with antisense therapeutic compositions. Even in disorders in which mutations in the corresponding gene are not implicated, downregulation or inhibition of nucleic acid-related gene expression can have therapeutic application. For example, decreasing nucleic acid-related gene expression can help to suppress tumors in which enhanced expression of the gene is implicated.

Both the dose of the antisense composition and the means of administration are determined based on the specific qualities of the therapeutic composition, the condition, age, and weight of the patient, the progression of the disease, and other relevant factors. Administration of the therapeutic antisense agents of the invention includes local or systemic administration, including injection, oral administration, particle gun or catheterized administration, and topical administration. Preferably, the therapeutic antisense composition contains an expression construct comprising a promoter and a polynucleotide segment of at least about 12, 22, 25, 30, or 35 contiguous nucleotides of the antisense strand of a nucleic acid. Within the expression construct, the polynucleotide segment is located downstream from the promoter, and transcription of the polynucleotide segment initiates at the promoter.

Various methods are used to administer the therapeutic composition directly to a specific site in the body. For example, a small metastatic lesion is located and the therapeutic composition injected several times in several different locations within the body of tumor. Alternatively, arteries which serve a tumor are identified, and the therapeutic composition injected into such an artery, in order to deliver the composition directly into the tumor. A tumor that has a necrotic center is aspirated and the composition injected directly into the now empty center of the tumor. The antisense composition is directly administered to the surface of the tumor, for example, by topical application of the composition. X-ray imaging is used to assist in certain of the above delivery methods.

Receptor-mediated targeted delivery of therapeutic compositions containing an antisense polynucleotide, subgenomic polynucleotides, or antibodies to specific tissues is also used. Receptor-mediated DNA delivery techniques are described in, for example, Findeis et al., *Trends in Biotechnol.* (1993) 11:202–205; Chiou et al., (1994) Gene Therapeutics: Methods And Applications Of Direct Gene Transfer (J. A. Wolff, ed.); Wu & Wu, *J. Biol. Chem.* (1988) 263: 621–24; Wu et al., *J. Biol. Chem.* (1994) 269:542–46; Zenke et al., *Proc. Nail. Acad. Sci.* (*USA*) (1990) 87:3655–59; Wu et al., *J. Biol. Chem.* (1991) 266:338–42. Preferably, receptor-mediaated targeted delivery of therapeutic compositions containing antibodies of the invention is used to deliver the antibodies to specific tissue.

Therapeutic compositions containing antisense subgenomic polynucleotides are administered in a range of about 100 ng to about 200 mg of DNA for local administration in a gene therapy protocol. Concentration ranges of about 500 ng to about 50 mg, about 1 mg to about 2 mg, about 5 mg to about 500 mg, and about 20 mg to about 100 mg of DNA can also be used during a gene therapy protocol. Factors such as method of action and efficacy of transformation and expression are considerations which will affect the dosage required for ultimate efficacy of the antisense subgenomic nucleic acids. Where greater expression is desired over a larger area of tissue, larger amounts of antisense subgenomic nucleic acids or the same amounts readministered in a successive protocol of administrations, or several administrations to different adjacent or close tissue portions of, for example, a tumor site, may be required to effect a positive therapeutic outcome. In all cases, routine experimentation in clinical trials will determine specific ranges for optimal therapeutic effect. A more complete description of gene therapy vectors, especially retroviral vectors, is contained in U.S. Ser. No. 08/869,309, which is expressly incorporated herein, and in section F below.

For genes encoding polypeptides or proteins with anti-inflammatory activity, suitable use, doses, and administration are described in U.S. Pat. No. 5,654,173, incorporated herein by reference. Therapeutic agents also include antibodies to proteins and polypeptides encoded by the subject nucleic acids, as described in U.S. Pat. No. 5,654,173.

F. Gene Therapy

The therapeutic nucleic acids of the present invention may be utilized in gene delivery vehicles. The gene delivery vehicle may be of viral or non-viral origin (see generally, Jolly, *Cancer Gene Therapy* (1994) 1:51–64; Kimura, *Human Gene Therapy* (1994) 5:845–852; Connelly, *Human*

Gene Therapy (1995) 1:185–193; and Kaplitt, Nature Genetics (1994) 6:148–153). Gene therapy vehicles for delivery of constructs including a coding sequence of a therapeutic of the invention can be administered either locally or systemically. These constructs can utilize viral or non-viral vector approaches. Expression of such coding sequences can be induced using endogenous mammalian or heterologous promoters. Expression of the coding sequence can be either constitutive or regulated.

The present invention can employ recombinant retroviruses which are constructed to carry or express a selected nucleic acid molecule of interest. Retrovirus vectors that can be employed include those described in EP 0415 731; WO 90/07936; WO 94/03622; WO 93/25698; WO 93/25234; U.S. Pat. No. 5,219,740; WO 93/1 1230; WO 93/10218; Vile and Hart, Cancer Res. (1993) 53:3860–3864; Vile and Hart, Cancer Res. (1993) 53:962–967; Ram et al., Cancer Res. (1993) 53:83–88; Takamiya et el., J. Neurosci. Re.s. (1992) 33:493–503; Baba et al., J. Neurosurg. (1993) 79:729–735; U.S. Pat. No. 4,777,127; GB Patent No. 2,200,651; and EP 0 345 242. Preferred recombinant retroviruses include those described in WO 91/02805.

Packaging cell lines suitable for use with the above-described retroviral vector constructs may be readily prepared (see PCT publications WO 95/30763 and WO 92/05266), and used to create producer cell lines (also termed vector cell lines) for the production of recombinant vector particles. Within particularly preferred embodiments of the invention, packaging cell lines are made from human (such as HT1O8O cells) or mink parent cell lines, thereby allowing production of recombinant retroviruses that can survive inactivation in human serum.

The present invention also employs alphavirus-based vectors that can function as gene delivery vehicles. Such vectors can be constructed from a wide variety of alphaviruses, including, for example, Sindbis virus vectors, Semliki forest virus (ATCC VR-67; ATCC VR-1247), Ross River virus (ATCC VR-373; ATCC VR1246) and Venezuelan equine encephalitis virus (ATCC VR-923; ATCC VR-1250; ATCC VR 1249; ATCC VR-532). Representative examples of such vector systems include those described in U.S. Pat. Nos. 5,091,309; 5,217,879; and 5,185,440; and PCT Publication Nos. WO 92/10578; WO 94/21792; WO 95/27069; WO 95/27044; and WO 95/07994.

Gene delivery vehicles of the present invention can also employ parvovirus such as adeno-associated virus (AAV) vectors. Representative examples include the AAV vectors disclosed by Srivastava in WO 93/09239, Samulski et al., J. Vir. (1989) 63:3822–3828; Mendelson et al., Virol. (1988) 166:154–165; and Flotte et al., PNAS (1993) 90:10613–10617.

Representative examples of adenoviral vectors include those described by Berkner, Biotechniques (1988) 6:616–627; Rosenfeld et al., Science (1991) 252:431–434; WO 93/19191Kolls et al., PNAS (1994) 91:215–219; Kass-Eisler et al., PNAS (1993) 90:11498–11502; Guzman et al., Circulation (1993) 88:2838–2848; Guzman et at, Cir. Res. (1993) 73:1202–1207; Zabner et al., Cell (1993) 75:207–216; Li Ct et al., Hum. Gene Ther. (1993) 4:403–409; Cailaud et al., Eur. J Neurosci. (1993) 5:1287–1291; Vincent et al., Nat. Genet. (1993) 5:130–134; Jaffe et al., Nat. Genet. (1992) 1:372–378; and Levrero et al., Gene (1991) 101:195–202. Exemplary adenoviral gene therapy vectors employable in this invention also include those described in WO 94/12649, WO 93/03769; WO 93/19191; WO 94/28938; WO 95/11984 and WO 95/00655.

Administration of DNA linked to killed adenovirus as described in Curiel, Hum. Gene Ther. (1992) 3:147–154 may be employed.

Other gene delivery vehicles and methods may be employed, including polycationic condensed DNA linked or unlinked to killed adenovirus alone, for example Curiel, Hum. Gene Ther. (1992)3:147–154; ligand linked DNA, for example see Wu, J. Biol. Chem. (1989) 264:16985–16987; eukaryotic cell delivery vehicles cells, for example see U.S. Ser. No. 08/240,030, filed May 9, 1994, and U.S. Ser. No. 08/404,796; deposition of photopolymerized hydrogel materials; hand-held gene transfer particle gun, as described in U.S. Pat. No. 5,149,655; ionizing radiation as described in U.S. Pat. No. 5,206,152 and in W092111033; nucleic charge neutralization or fusion with cell membranes. Additional approaches are described in Philip, Mol. Cell Biol. (1994) 14:2411–2418, and in Woffendin, Proc. Natl. Acad. Sci. (1994) 91:1581–1585.

Naked DNA may also be employed. Exemplary naked DNA introduction methods are described in WO 90111092 and U.S. Pat. No. 5,580,859. Uptake efficiency may be improved using biodegradable latex beads. DNA coated latex beads are efficiently transported into cells after endocytosis initiation by the beads. The method may be improved further by treatment of the beads to increase hydrophobicity and thereby facilitate disruption of the endosome and release of the DNA into the cytoplasm. Liposomes that can act as gene delivery vehicles are described in U.S. Pat. No. 5,422,120, PCT Nos. WO 95/13796, WO 94/23697, and WO 91/14445, and EP No. 0524 968.

Further non-viral delivery suitable for use includes mechanical delivery systems such as the approach described in Woffendin et al., Proc. Natl. Acad. Sci. USA (1994) 91(24):11581–11585. Moreover, the coding sequence and the product of expression of such can be delivered through deposition of photopolymerized hydrogel materials. Other conventional methods for gene delivery that can be used for delivery of the coding sequence include, for example, use of hand-held gene transfer particle gun, as described in U.S. Pat. No. 5,149,655; use of ionizing radiation for activating transferred gene, as described in U.S. Pat. No. 5,206,152 and PCT No. WO 92/11033.

G. Transgenic Animals

One aspect of the present invention relates to transgenic non-human animals having germline and/or somatic cells in which the biological activity of one or more genes are altered by a chromosomally incorporated transgene.

In a preferred embodiments, the transgene encodes a mutant protein, such as dominant negative protein which antagonizes at least a portion of the biological function of a wild-type protein.

Yet another preferred transgenic animal includes a transgene encoding an antisense transcript which, when transcribed from the transgene, hybridizes with a gene or a mRNA transcript thereof, and inhibits expression of the gene.

In one embodiment, the present invention provides a desired non-human animal or an animal (including human) cell which contains a predefined, specific and desired alteration rendering the non-human animal or animal cell predisposed to cancer. Specifically, the invention pertains to a genetically altered non-human animal (most preferably, a mouse), or a cell (either non-human animal or human) in culture, that is defective in at least one of two alleles of a tumor-suppressor gene. The inactivation of at least one of these tumor suppressor alleles results in an animal with a higher susceptibility to tumor induction or other proliferative or differentiative disorders, or disorders marked by aberrant signal transduction, e.g., from a cytokine or growth factor. A genetically altered mouse of this type is able to serve as a useful model for hereditary cancers and as a test animal for carcinogen studies. The invention additionally pertains to the use of such non-human animals or animal cells, and their progeny in research and medicine.

Furthermore, it is contemplated that cells of the transgenic animals of the present invention can include other transgenes, e.g., which alter the biological activity of a second tumor suppressor gene or an oncogene. For instance, the second transgene can functionally disrupt the biological activity of a second tumor suppressor gene, such as p53, p73, DCC, $p21^{cip1}$, $p27^{kip1}$, Rb, Mad or E2F. Alternatively, the second transgene can cause overexpression or loss of regulation of an oncogene, such as ras, myc, a cdc25 phosphatase, Bcl-2, Bcl-6, a transforming growth factor, neu, int-3, polyoma virus middle T antigen, SV4O large T antigen, a papillomaviral E6 protein, a papillomaviral E7 protein, CDK4, or cyclin D1.

A preferred transgenic non-human animal of the present invention has germline and/or somatic cells in which one or more alleles of a gene are disrupted by a chromosomally incorporated transgene, wherein the transgene includes a marker sequence providing a detectable signal for identifying the presence of the transgene in cells of the transgenic animal, and replaces at least a portion of the gene or is inserted into the gene or disrupts expression of a wild-type protein.

Still another aspect of the present invention relates to methods for generating non-human animals and stem cells having a functionally disrupted endogenous gene. In a preferred embodiment, the method comprises the steps of:
  (i) constructing a transgene construct including (a) a recombination region having at least a portion of the gene, which recombination region directs recombination of the transgene with the gene, and (b) a marker sequence which provides a detectable signal for identifying the presence of the transgene in a cell;
  (ii) transferring the transgene into stem cells of a non-human animal;
  (iii) selecting stem cells having a correctly targeted homologous recombination between the transgene and the gene;
  (iv) transferring cells identified in step (iii) into a non-human blastocyst and implanting the resulting chimeric blastocyst into a non-human female; and
  (v) collecting offspring harboring an endogenous gene allele having the correctly targeted recombination.

Yet another aspect of the invention provides a method for evaluating the carcinogenic potential of an agent by (i) contacting a transgenic animal of the present invention with a test agent, and (ii) comparing the number of transformed cells in a sample from the treated animal with the number of transformed cells in a sample from an untreated transgenic animal or transgenic animal treated with a control agent. The difference in the number of transformed cells in the treated animal, relative to the number of transformed cells in the absence of treatment with a control agent, indicates the carcinogenic potential of the test compound.

Another aspect of the invention provides a method of evaluating an anti-proliferative activity of a test compound. In preferred embodiments, the method includes contacting a transgenic animal of the present invention, or a sample of cells from such animal, with a test agent, and determining the number of transformed cells in a specimen from the transgenic animal or in the sample of cells. A statistically significant decrease in the number of transformed cells, relative to the number of transformed cells in the absence of the test agent, indicates the test compound is a potential anti-proliferative agent.

The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, *Molecular Cloning A Laboratory Manual,* 2nd Ed., ed. by Sambrook, Fritsch and Maniatis (Cold Spring Harbor Laboratory Press:1989); *DNA Cloning,* Volumes I and II (D. N. Glover ed., 1985); *Oligonucleotide Synthesis* (M. J. Gait ed., 1984); Mullis et al. U.S. Pat. No. 4,683,195; *Nucleic Acid Hybridization* (B. D. Hames & S. J. Higgins eds. 1984); *Transcription And Translation* (B. D. Hames & S. J. Higgins eds. 1984); *Culture Of Animal Cells* (R. I. Freshney, Alan R. Liss, Inc., 1987); *Immobilized Cells And Enzymes* (IRL Press, 1986); B. Perbal, *A Practical Guide To Molecular Cloning* (1984); the treatise, *Methods in Enzymology* (Academic Press, Inc., N.Y.); *Gene Transfer Vectors For Mammalian Cells* (J. H. Miller and M. P. Calos eds., 1987, Cold Spring Harbor Laboratory); *Methods In Enzymology,* Vols. 154 and 155 (Wu et al. eds.), *Immunochemical Methods In Cell And Molecular Biology* (Mayer and Walker, eds., Academic Press, London, 1987); *Handbook Of Experimental Immunology,* Volumes I–IV (D. M. Weir and C. C. Blackwell, eds., 1986); *Manipulating the Mouse Embryo,* (Cold Spring Harbor Laboratory Press, Cold Spring Harbor, N.Y., 1986).

As mentioned above, the sequences described herein are believed to have particular utility in regards to colon cancer. However, they may also be useful with other types of cancers and other disease states.

The present invention will now be illustrated by reference to the following examples which set forth particularly advantageous embodiments. However, it should be noted that these embodiments are illustrative and are not to be construed as restricting the invention in any way.

XI. Examples

A. Identification of Differentially Expressed Sequences.

Description of the Libraries

SEQ ID Nos: 1, 3, 5, or 7 were derived from libraries designated as DE and PA as described below. The DE library is a normalized, colon cancer specific, subtracted cDNA library. The DE library is specific for sequences expressed in colon cancer [proximal and distal Dukes' B, microsatellite stable (MSS)] but not expressed in normal tissues, including normal colon tissue. The PA library is a normalized, colon specific, subtracted cDNA library. The PA library is specific for sequences expressed in normal colon tissue but not expressed in other normal tissues.

Construction of a Colon Cancer Specific Library

A subtracted colon cancer specific library was made by subtracting pooled proximal, stage B, MSS and distal, Stage B, MSS tumor tissue cDNA against a combination of pooled driver normal cDNA made from colon, peripheral blood leukocytes (PBL), liver, spleen, lung, kidney, heart, small intestine, skeletal muscle, and prostate tissue cDNAs. The following RNA samples were obtained from Origene Technologies, Inc., Rockville, Md., and were used to synthesize the pooled driver cDNA: #HT-1015 normal colon total RNA, #HT-1005 liver total RNA, #HT-1004 spleen total RNA, #HT-1009 lung total RNA, #HT-1003 kidney total RNA, #HT-1006 peripheral blood leukocyte total RNA, #HT-prostate total RNA, #HM-1002 heart muscle poly A+ RNA, #HM-1007 intestine poly A+ RNA, and #HM-1 008 skeletal muscle poly A+ RNA. First-strand cDNA was prepared for each using 1 microgram of RNA. A biased pool of first-strand cDNA was prepared containing 50% normal colon first-strand cDNA reaction and 5.56% of each of the remaining tissue first-strand cDNA reactions by volume. Eight individual amplification reactions, each containing 1 microliter of the biased first-strand cDNA reaction pool, were performed for 18 cycles. The double stranded cDNA product from all eight amplification reactions were pooled and purified for subsequent use in subtractive hybridization. The colon cancer specific subtracted library was called DE and individual clones derived from this library were referred to with a number prefixed by DE.

Normalized subtracted DE colon cancer specific and pooled normal human tissue specific cDNA libraries (same as components of driver cDNA above) were generated according published procedures (Daitchenko et al., 1996 PNAS 93:6025–6030, Gurskaya et al., 1996 Analytical Biochemistry 240:90–97) using Clontech Laboratories, Inc., PCR-Select cDNA subtraction kit, PT1117-1. A forty-five fold mass excess of driver cDNA (450 nanograms) was used for each subtraction experiment. Subtractive hybridization of tester with driver cDNAs was performed twice, each time for about 8–12 hours. Subtracted cancer specific DE cDNA was ligated into the pCR2.1-TOPO plasmid vector (Invitrogen Corporation, Carlsbad Calif.) and chemically transformed into ultracompetent Epicurian E. coli XL1O-Gold cells (Stratagene, La Jolla, Calif.). A reverse library was also constructed wherein the tester and driver samples were switched; this library was designated as MD.

Construction of a Normal Colon Specific Library

This normal colon tissue specific library was made using Clontech Laboratories Inc PCR-Select kit, K1804-1, following instructions from the users manual (PT1117-1).

Four, 100⊠1, SMART PCR cDNA amplification reactions for each normal, non-cancerous, patient sample, were performed, starting with 1⊠1 from their respective first strand cDNA reactions. Each sample was amplified for only 18 cycles using the following PCR conditions; 95 C-b sec, 68 C 5 mm. using a 9600 Perkin Elmer instrument. The following are Bayer Diagnostic sample identification numbers for the cDNA samples that were amplified: NPB(-) 27347, NPB(-)27859, NPB(-)28 147, NPB(-)28 162, NDB (-)28800, NDB(-)29243, NDB(-)29244 and NDB(-) 42472. These are normal colon tissue samples obtained from the same patients providing the proximal stage B MSS and distal stage B MSS cancer samples, which were used to prepare the DE library described above. Equal volumes of the eight normal colon cDNAs were pooled. A subtracted normal colon tissue specific library was made by subtracting the normal colon cDNA pool against a combination of pooled driver normal cDNA made from peripheral blood leukocytes (PBL), liver, spleen, lung, kidney, heart, small intestine, skeletal muscle, and prostate tissue cDNAs. The following are the RNA samples that were used to synthesize the pooled driver cDNA: #HT-1005 liver total RNA, #HT-b 004 spleen total RNA, #HT1009 lung total RNA, #HT-1003 kidney total RNA, #HT-1 006 peripheral blood leukocyte total RNA, #HT-prostate total RNA, #HM-1 002 heart muscle poly A+ RNA, #HM-1007 intestine poly A+ RNA, and #HM-b008 skeletal muscle poly A+ RNA. First-strand cDNA was prepared for each using 1 microgram of RNA. A pool of first strand cDNA reactions was then made consisting of equal volumes of the nine driver tissue first-strand cDNA reactions. Eight individual amplification reactions, each containing 1 microliter of the first-strand cDNA reaction pool, were performed for 18 cycles. The double stranded cDNA product from all eight amplification reactions was pooled and purified for subsequent use in subtractive hybridization. The normal colon tissue specific subtracted library was called PA and individual clones derived from this library were referred to with a number prefixed by PA.

The normalized subtracted PA normal colon specific cDNA library and a subtracted normal human tissue specific cDNA library, consisting of the human tissues listed above were generated according published procedures (Daitchenko et al., 1996 PNAS 93:6025–6030, Gurskaya et al., 1996 Analytical Biochemistry 240:90–97) using Clontech Laboratories, Inc., PCR-Select cDNA subtraction kit, P11117-1. Library construction and cloning were carried out as described above for the colon cancer specific library. Out of the 1152 clones that were analyzed for differential expression, approximately 69% were differentially expressed, as described in the co-pending application U.S. Ser. No. 09/385,982.

Each EST isolated from each of the above libraries represents a sequence from a partial mRNA transcript, since the cDNA used for making the subtracted library was restricted with RsaI, a four base cutter restriction endonuclease that generates fragments with an average size of about 600 base pairs.

Validation of Differential Expression in Colon Cancer

To validate that the differentially expressed sequences found in this library were specific to colon cancer, the clones were screened with cDNAs prepared from a colon cancer specific library, Delaware (DE), and a normal tissue specific library Maryland (MD).

cDNA clones were analyzed for differential expression following the procedure developed by von Stein et al., 1997, Nucleic Acids Research 25(13):2598–2602 and using probes synthesized according to a published method (Jin et al., 1997, Biotechniques 23:1083–1086). Out of the 1248 clones that were analyzed for differential expression approximately 83% were differentially expressed, as described in the co-pending application U.S. Ser. No. 09/385,982.

Sequencing and Analysis of Differentially Expressed Clones

The nucleotide sequence of the inserts from clones shown to be differentially expressed was determined by single-pass sequencing from either the T7 or M13 promoter sites using fluorescently labeled dideoxynucleotides via the Sanger sequencing method. Sequences were analyzed according to methods described in the text (XI., Examples; B. Results of Public Database Search).

Each nucleic acid represents sequence from at least a partial mRNA transcript.

The nucleic acids of the invention were assigned a sequence identification number (see attachments). The nucleic acid sequences are provided in the attached Sequence Listing.

An example of an experiment to identify differentially expressed clones is shown in the Figure, "Differential Expression Analysis". The inserts from subtracted clones were amplified, electrophoresed, and blotted on to membranes as described above. The gel was hybridized with RSA1 cut DE and MD cDNA probes as described above.

In the Figure, individual clones are designated by a number at the top of each lane; the blots are aligned so that the same clone is represented in the same vertical lane in both the upper ("Cancer Probe") and lower ("Normal Probe") blot. Lanes labeled "O" indicate clones that are overexpressed, i.e., show a darker, more prominent band in the upper blot ("Cancer Probe") relative to that observed, in the same lane, in the lower blot ("Normal Probe"). The Lane labeled "U" indicates a clone that is underexpressed, i.e., shows a darker, more prominent band in the lower blot ("Normal Probe") relative to that observed, in the same lane, in the upper blot ("Cancer Probe"). The lane labeled "M", indicates a clone that is marginally overexpressed in cancer and normal cells.

B. Results of Public Database Searches

The full length cDNA sequence of SEQ ID Nos. 1, 3, 5, or 7 were obtained through a BLAST2 search of GenBank using the partial sequence described in the co-pending application U.S. Ser. No. 09/385,982.

A total of 5 sequences were analyzed. The sequences were first masked to identify vector-derived sequences, which were subsequently removed. The remaining sequence information was used to create the Sequence Listing (SEQ ID Nos. 1, 3, 5, or 7). Each of these sequences was used as the query sequence to perform a BLAST 2 search against the databases listed above. The BLAST 2 search differs from the traditional Blast search in that it allows for the introduction of gaps in order to produce an optimal alignment of two sequences. The GenBank record of each full length sequence identified in the BLAST2 search was also utilized to obtain the amino acid sequence encoded by each cDNA.

Those skilled in the art will recognize, or be able to ascertain, using not more than routine experimentation, many equivalents to the specific embodiments of the invention described herein. Such specific embodiments and equivalents are intended to be encompassed by the following claims.

All patents, published patent applications, and publications cited herein are incorporated by reference as if set forth fully herein.

We claim:

1. A method for determining the presence or absence of a polypeptide encoded by a nucleic acid comprising SEQ ID No. 7, or a sequence complementary thereto in a patient sample comprising contacting the sample with an antibody immunoreactive with a polypeptide comprising the sequence of SEQ ID NO: 8, and detecting the reaction of the antibody with the polypeptide, wherein the presence or amount of the polypeptide detected is indicative of the presence of cancer.

2. A method for detecting cancer in a patient sample comprising contacting an antibody to a polypeptide having an amino acid sequence comprising at least a portion of SEQ ID No. 8 with the sample and detecting the reaction of the antibody with the polypeptide, wherein the presence or amount of the polypeptide detected is indicative of the presence of cancer.

3. The method of claim 2 wherein the cancer is colon cancer.

* * * * *